(12) United States Patent
Cocks et al.

(10) Patent No.: US 11,478,391 B2
(45) Date of Patent: Oct. 25, 2022

(54) SINGLE-USE EXPANDABLE LIQUID CONTAINER AND BLANK

(71) Applicant: HYGIENIUS INTELLECTUAL PROPERTY B.V., Breukelen (NL)

(72) Inventors: David Cocks, London (GB); Ian Alexander Webb, London (GB)

(73) Assignee: HYGIENIUS INTELLECTUAL PROPERTY B.V., Breukelen (NL)

( * ) Notice: Subject to any disclaimer, the term of this patent is extended or adjusted under 35 U.S.C. 154(b) by 13 days.

(21) Appl. No.: 16/479,417

(22) PCT Filed: Jan. 18, 2018

(86) PCT No.: PCT/NL2018/050039
§ 371 (c)(1),
(2) Date: Jul. 19, 2019

(87) PCT Pub. No.: WO2018/135945
PCT Pub. Date: Jul. 26, 2018

(65) Prior Publication Data
US 2019/0358108 A1    Nov. 28, 2019

(30) Foreign Application Priority Data

Jan. 20, 2017   (NL) ...................................... 2018201
Jan. 23, 2017   (NL) ...................................... 2018213

(51) Int. Cl.
*A61G 9/00*     (2006.01)
*A61F 5/453*    (2006.01)
(Continued)

(52) U.S. Cl.
CPC .............. *A61G 9/006* (2013.01); *A61F 5/453* (2013.01); *A61F 5/4556* (2013.01); *A61J 19/00* (2013.01);
(Continued)

(58) Field of Classification Search
CPC .... A61F 5/453–4556; A61G 9/00–003; A61G 9/006; A61J 9/00; B65D 5/3614; B65D 5/3621; B65D 5/3628; B65D 5/40
See application file for complete search history.

(56) References Cited

U.S. PATENT DOCUMENTS 2,315,390 A * 3/1943 Billeb ...................... A61G 9/00
                                                    4/484
4,309,779 A * 1/1982 Knight ................... A61G 9/006
                                                    4/144.1
(Continued)

FOREIGN PATENT DOCUMENTS

GB          898903 A       6/1962
GB         1092274 A      11/1967
(Continued)

OTHER PUBLICATIONS

The Korean Notice of Allowance dated Dec. 12, 2019; Appln. No. 10-2019-7024248.
(Continued)

*Primary Examiner* — David P Angwin
*Assistant Examiner* — Nicholas A Ros

(57) ABSTRACT

The present invention relates to a single-use container manufactured from sheet material, the single-use container comprising: a base, wherein the base is flat and forms a surface on which the single-use container can stand, —a front wall, a right wall, a left wall and a rear wall which extend upward from the base, wherein the front wall and the rear wall are convex, and wherein the right wall and left wall are concave, an upper end which connects the front wall, right wall, left wall and rear wall.

14 Claims, 40 Drawing Sheets

(51) Int. Cl.
    *A61F 5/455*    (2006.01)
    *A61J 19/00*    (2006.01)
    *B65D 5/36*     (2006.01)
    *B65D 5/40*     (2006.01)
    *B65D 5/54*     (2006.01)
    *A61F 5/44*     (2006.01)

(52) U.S. Cl.
    CPC ............ *B65D 5/3628* (2013.01); *B65D 5/40* (2013.01); *B65D 5/542* (2013.01); *A61F 2005/4402* (2013.01)

(56) References Cited

U.S. PATENT DOCUMENTS

| | | | |
|---|---|---|---|
| 6,170,739 B1 | 1/2001 | Hansen | |
| 7,604,155 B2* | 10/2009 | Bossel | B65D 77/02 |
| | | | 229/117.32 |
| 10,258,206 B2* | 4/2019 | Nelson | A61G 9/006 |
| 10,961,014 B2* | 3/2021 | Tart | B65D 5/3628 |
| 2011/0226763 A1 | 9/2011 | Valencia | |
| 2014/0270592 A1* | 9/2014 | Walsh | B65D 33/02 |
| | | | 383/105 |
| 2015/0083789 A1* | 3/2015 | Fitzwater | B65D 5/3628 |
| | | | 229/117.3 |
| 2016/0262583 A1 | 9/2016 | Nelson et al. | |

FOREIGN PATENT DOCUMENTS

| | | | | |
|---|---|---|---|---|
| GB | 2410939 | * | 8/2005 | ........... B65D 5/3628 |
| GB | 2410939 A | | 8/2005 | |
| JP | 2007-159797 A | | 6/2007 | |
| JP | 2007159797 A | | 6/2007 | |
| TW | M378197 U | | 4/2010 | |
| WO | 2009/027982 A2 | | 3/2009 | |

OTHER PUBLICATIONS

The International Search Report and Written Opinion dated May 30, 2018; PCT/NL2018/050039.
Priority Search Report NL00 P32861NL00/WHA.
Priority Search Report NL01 P32861NL01/WHA.
International Application Status Report PCT/NL2018/050039.

* cited by examiner

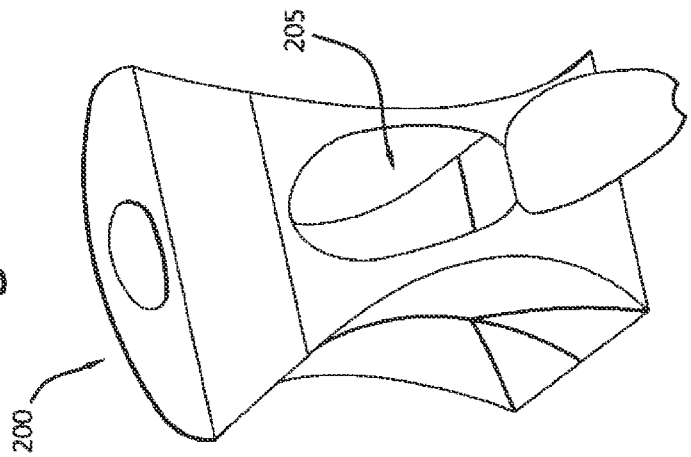
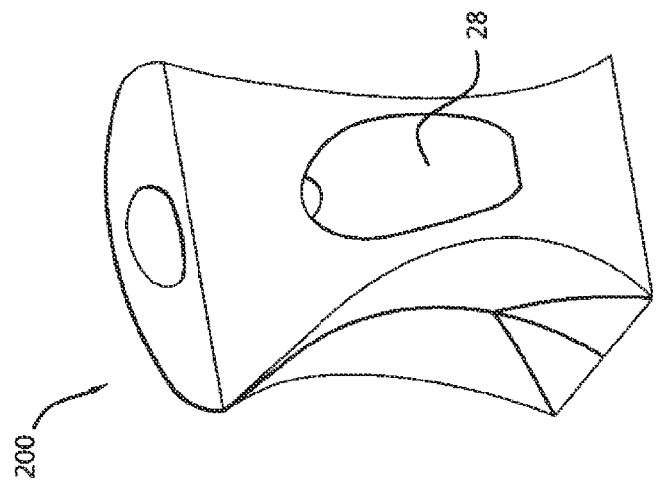
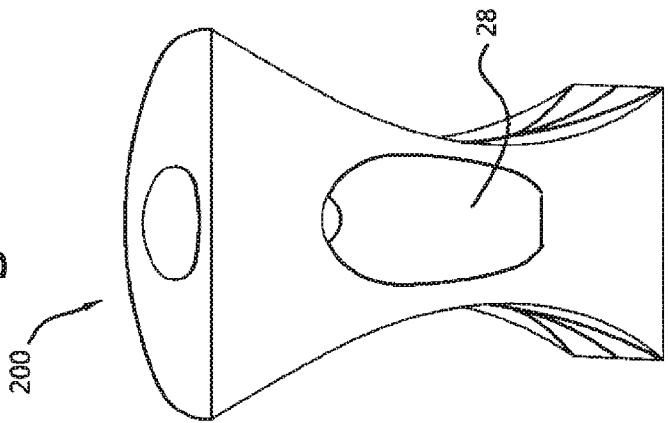

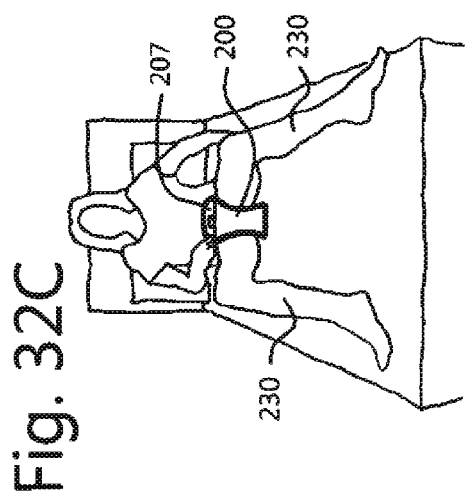
Fig. 32A  Fig. 32B  Fig. 32C
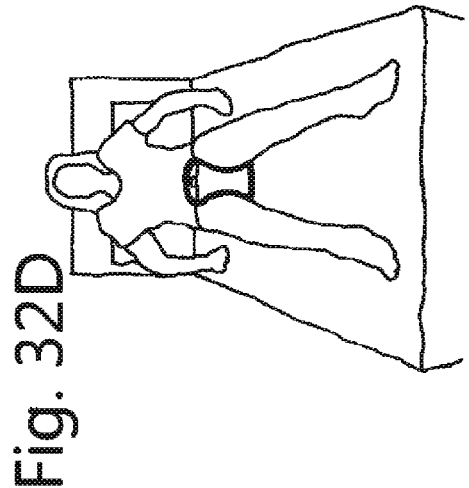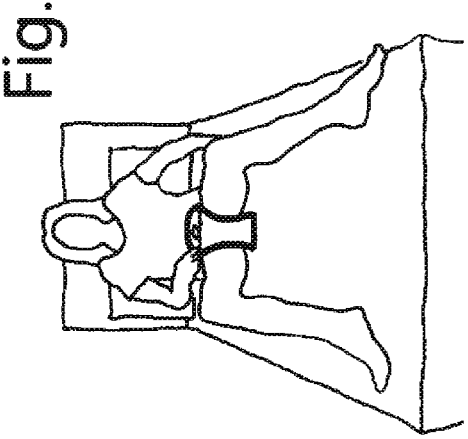
Fig. 32D  Fig. 32E

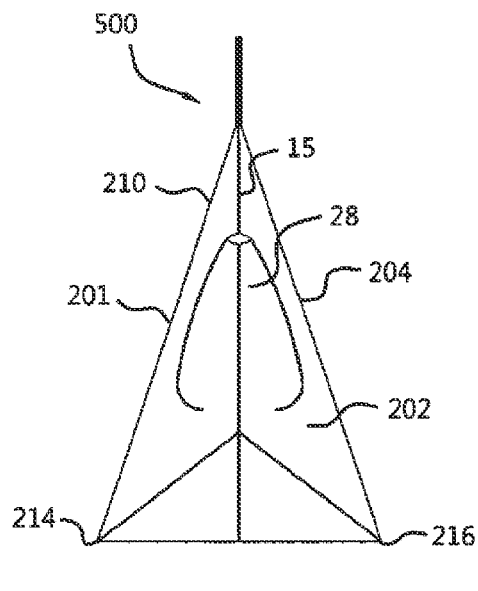
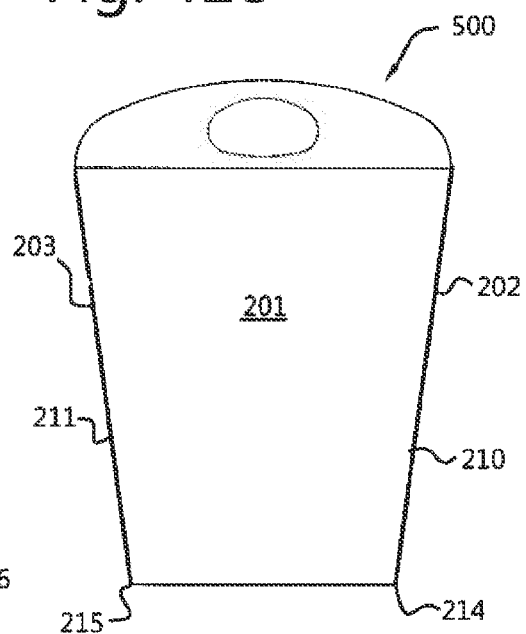
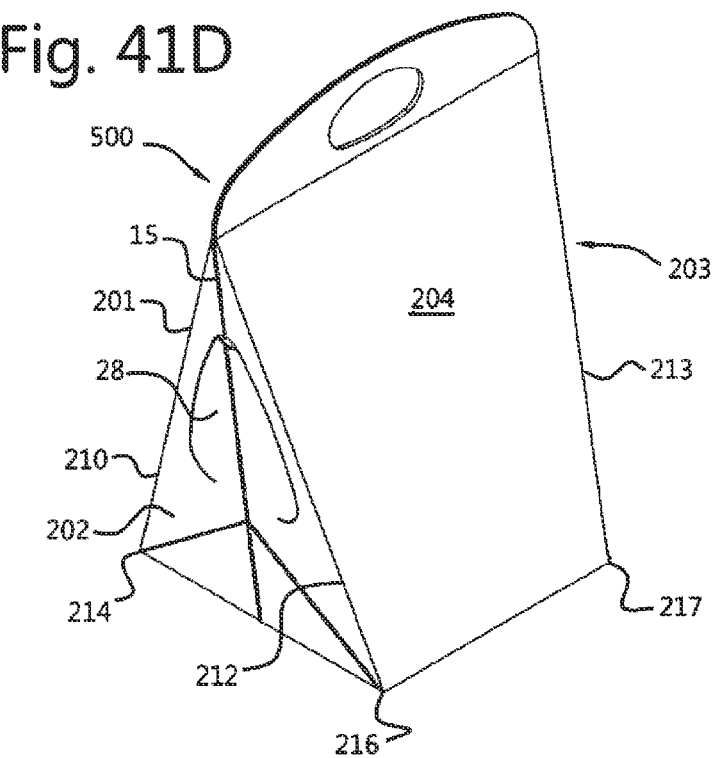

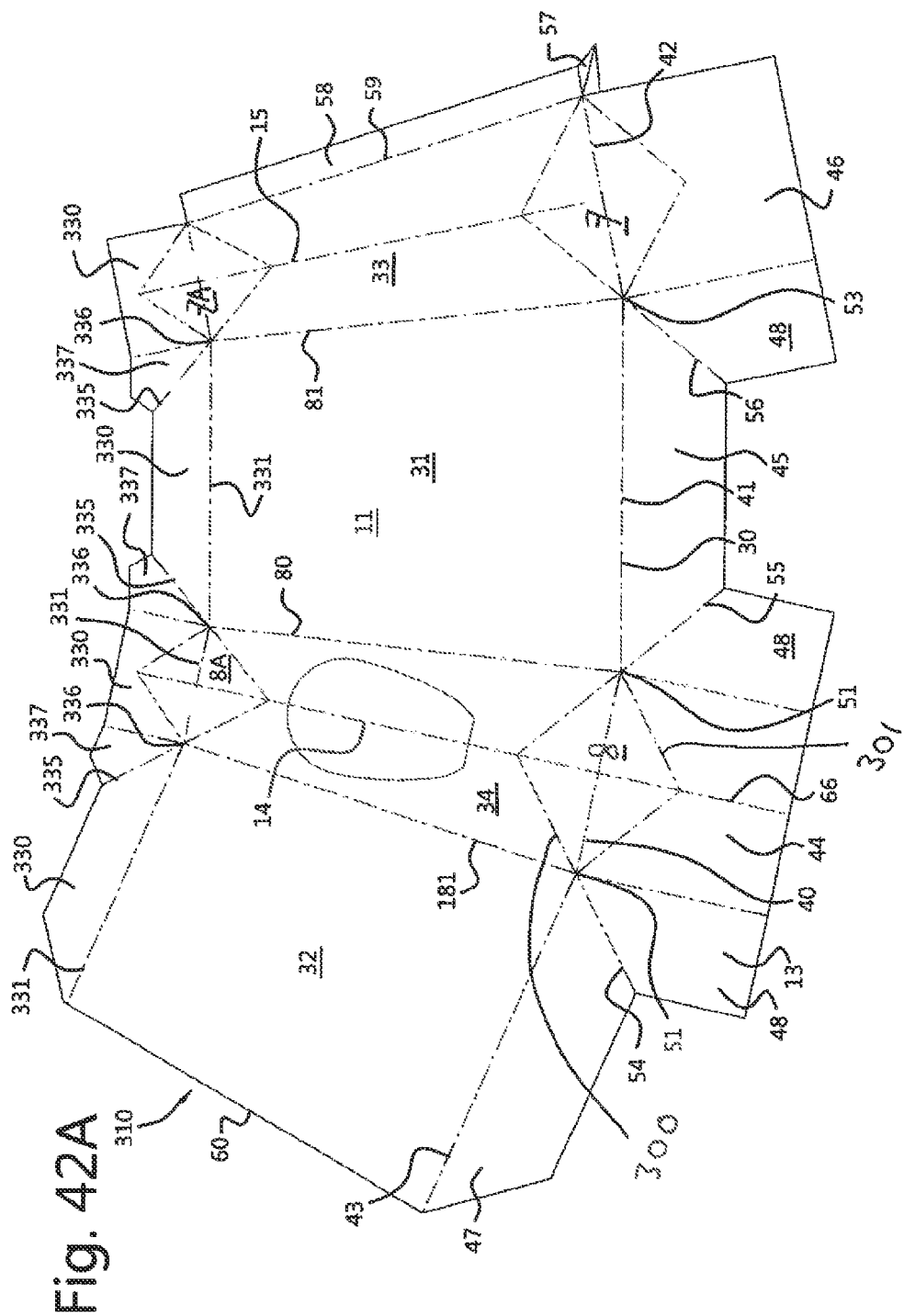

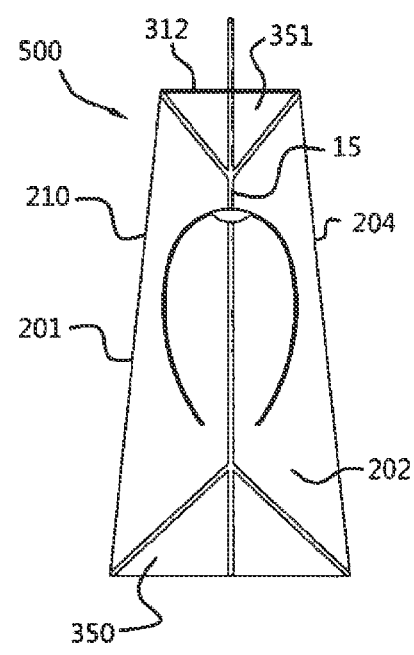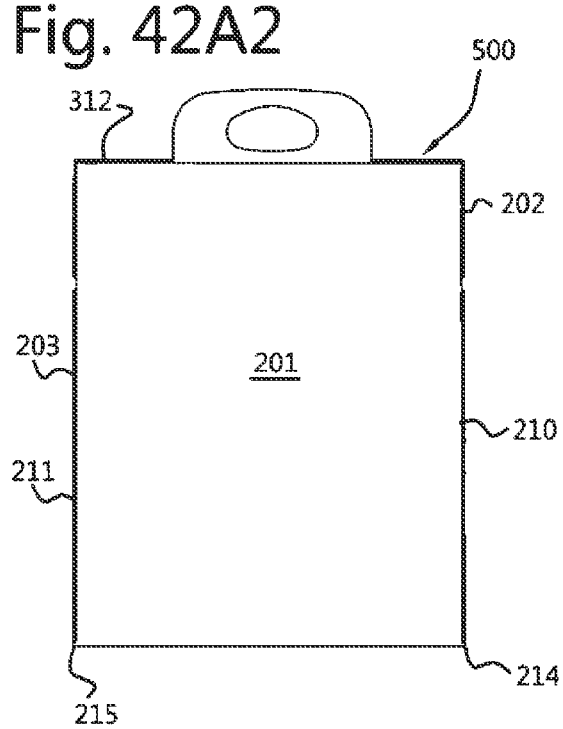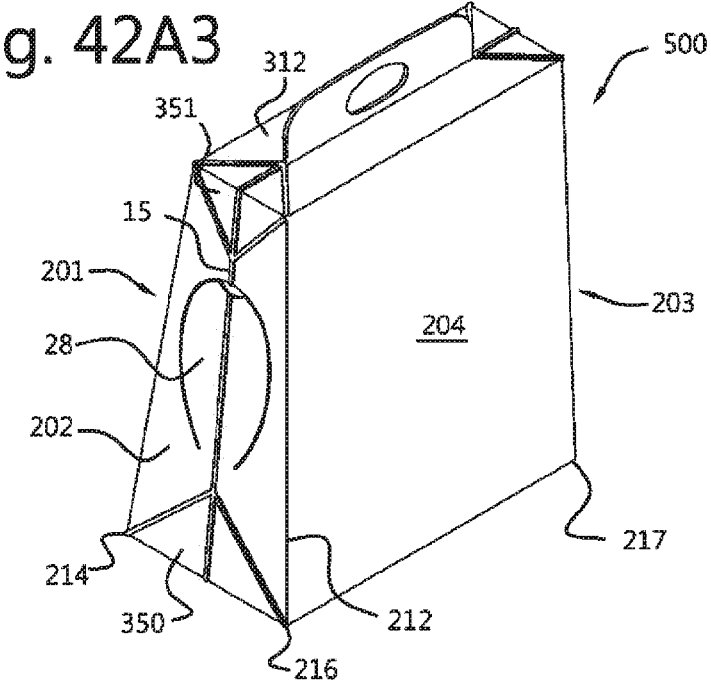

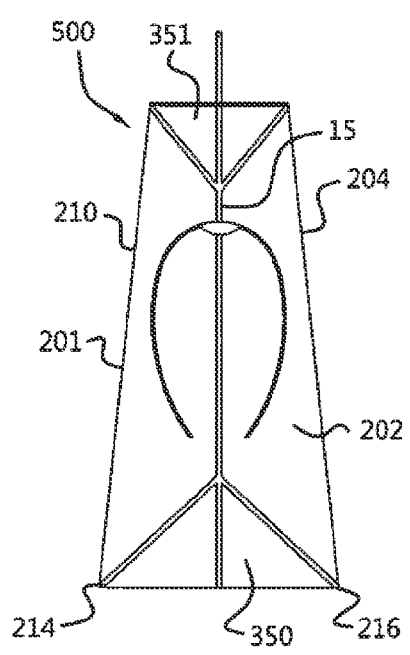
Fig. 42B1
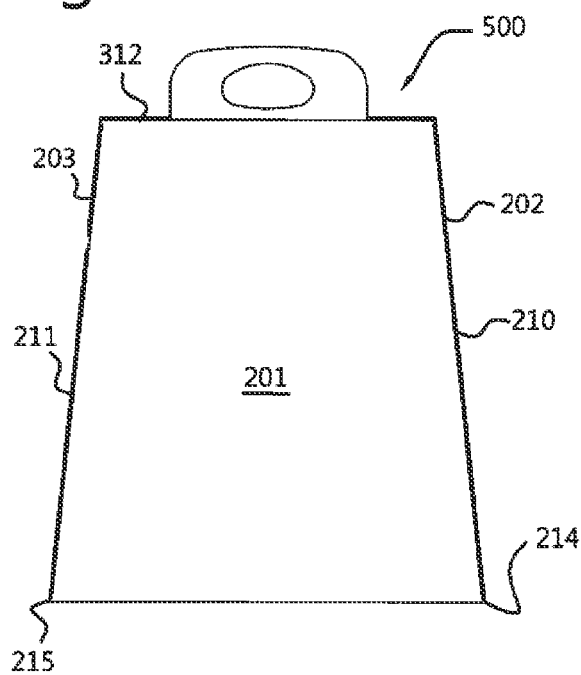
Fig. 42B2
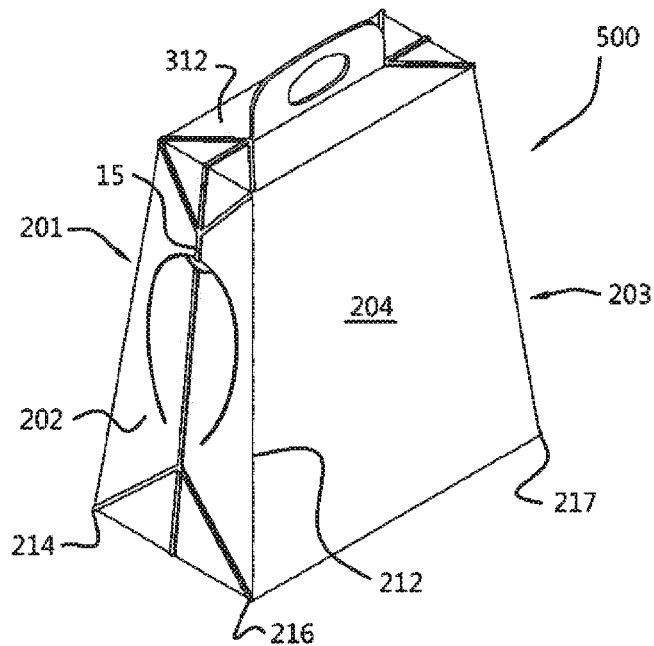
Fig. 42B3

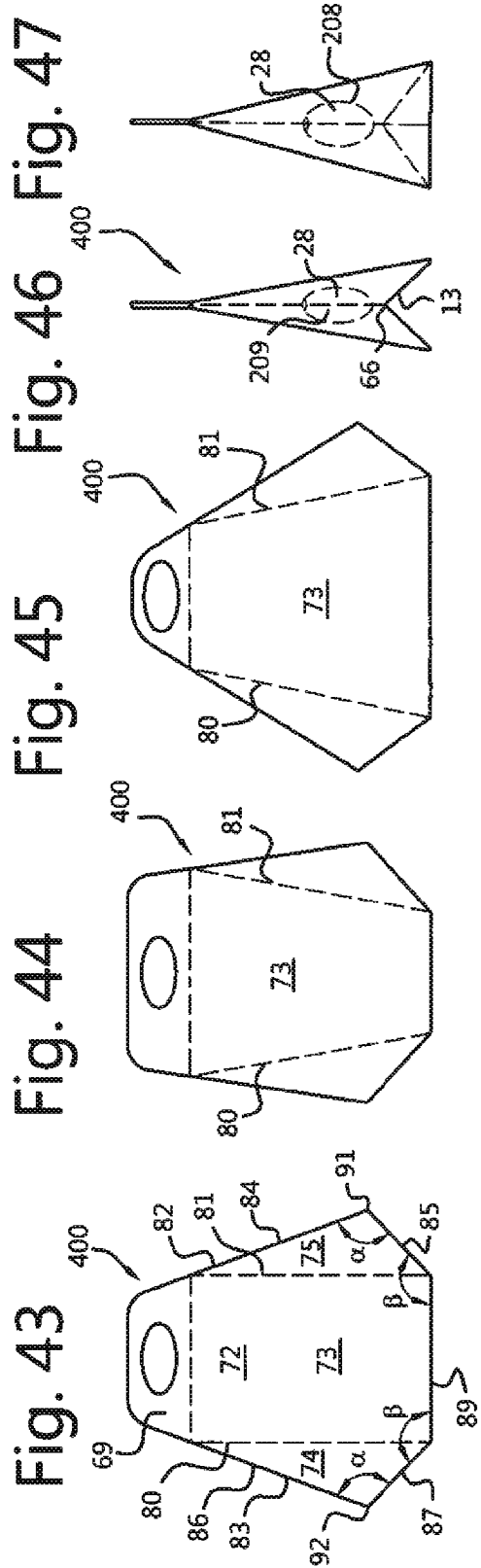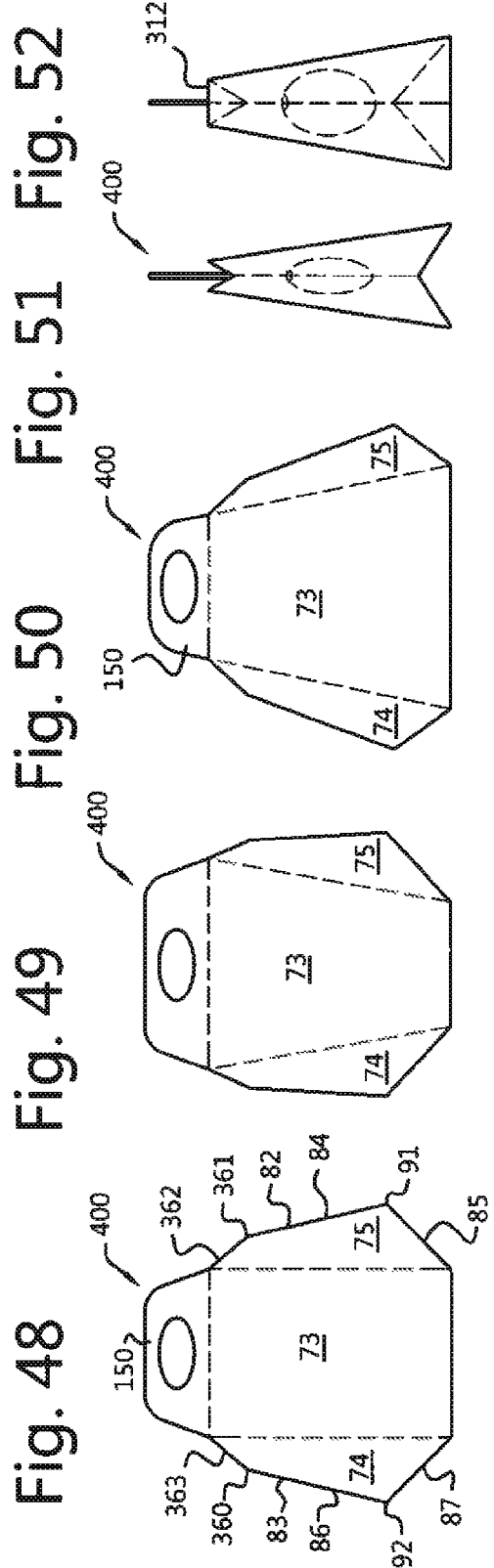

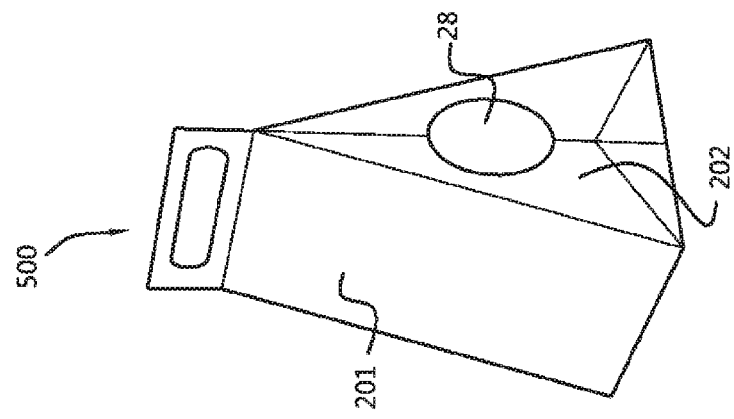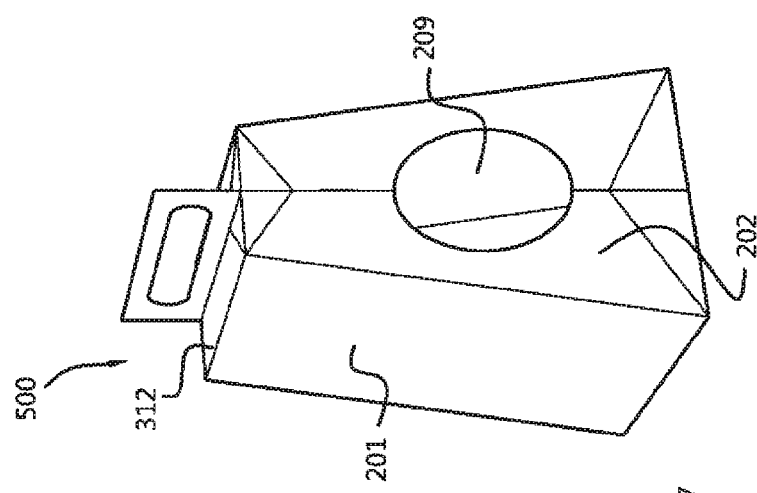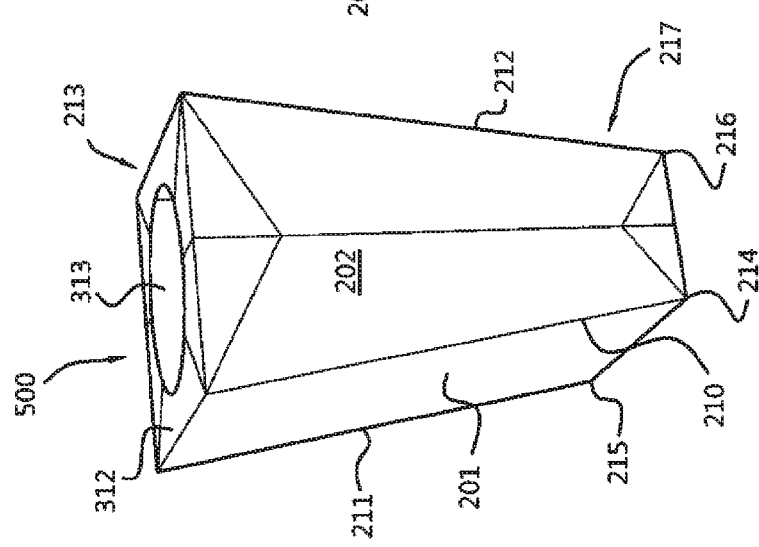

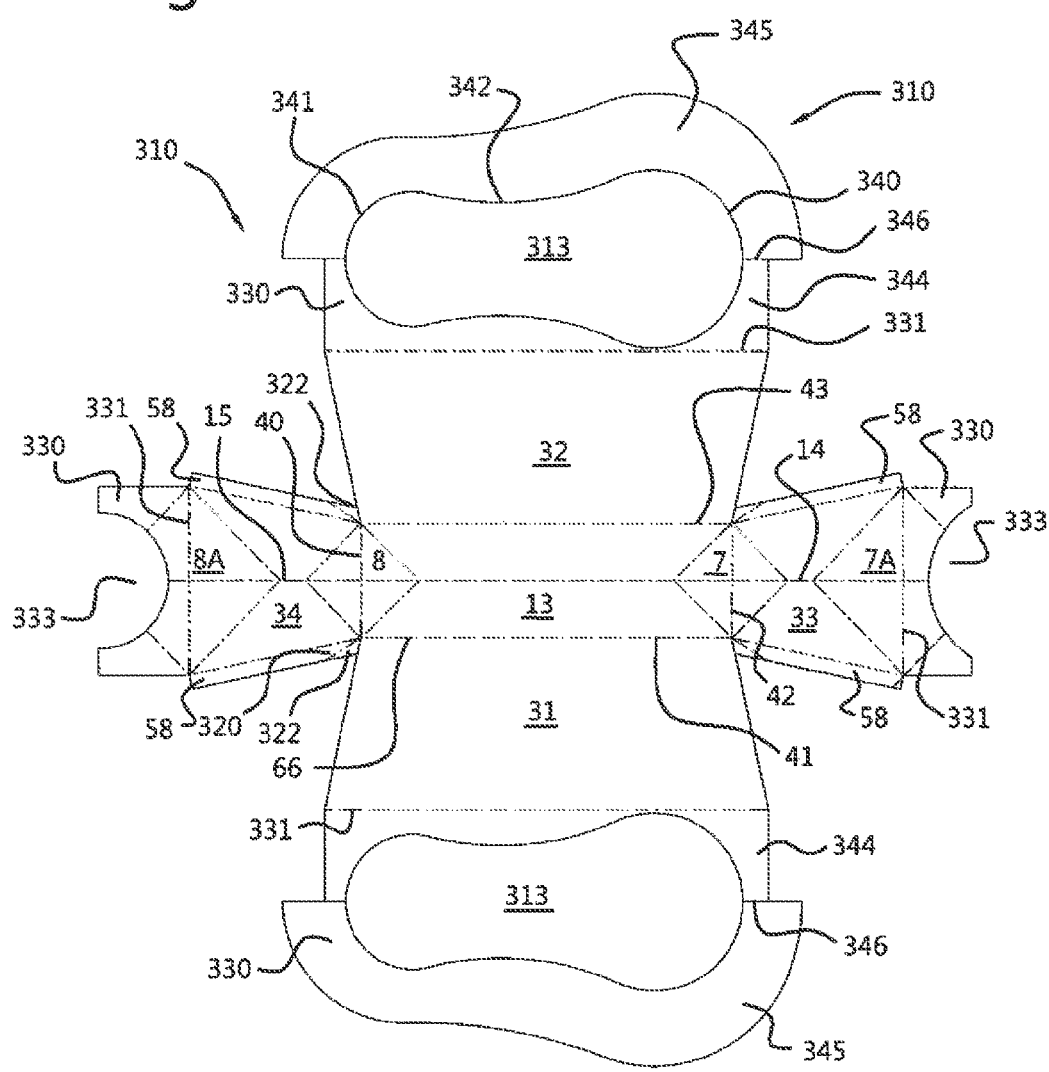

SINGLE-USE EXPANDABLE LIQUID CONTAINER AND BLANK

FIELD OF THE INVENTION

The present invention relates to a single-use liquid container which is made from sheet material in particular for holding body fluids in a medical environment, and which can be expanded with a simple movement. The present invention further relates to a collapsed single-use container and to a blank. The single-use, expandable container may in particular be used as a urinal or as a sick bag.

BACKGROUND OF THE INVENTION

Single-use containers which are made from sheet material have been known for quite some time. Single-use containers may be used as urinals and in that case have an advantage over reusable urinals in that they significantly reduce the risk of Hospital Acquired Infections, because reusable urinals are often not cleaned very well in practice and become a source of infections. This type of infection does not occur with single use urinals.

An example of a single-use, collapsible container is disclosed in GB2529713A. This document discloses a collapsible container, in particular a collapsible male urinal. A disadvantage of this container is that the shape is not very well suited for a human body. The container has a rather angular shape which feels rather inconvenient for a user when the container is placed between the legs of the user. Furthermore the container cannot be expanded ("popped-up") by a simple movement.

Another example of a single-use liquid container is disclosed in US2016/0262583A1. The containers disclosed in this document are in particular made from carton and are formed from a pre-cut blank.

GB2410939 (D1) discloses a container having a convex front wall. However, this carton is not a urinal. The container of D1 is only open at the top. Furthermore, D1 does not disclose that the container is liquid tight. D1 also does not comprise any pointer towards using this container as a urinal or towards making this container liquid tight.

FIG. 4 of D1 shows the blank from which the container is made. At least one of the corner locations which form the corners of the base of the container is located along an edge of the blank and for this reason will result in leakage of the container when the container would be filled with a liquid. The container of D1 also has a less economical shape.

This container has a similar drawback in that the three-dimensional shape is not well suited to be used as a urinal. The container does not fit very well between the legs of a user when the user is lying in bed. Moreover, the shape of the entry opening is not very suitable for various positions which a user may have when lying in a bed. This holds in particular when the user has a supine position. Furthermore, the container cannot be expanded in full form by a simple movement. Moreover, when the container contains liquid, it tips over quite easily at a typical 10-15° mattress angle and spills the liquid quite easily.

The challenge of providing a user friendly and sturdy shape is particularly difficult because single-use containers need to be able to be transformed between a collapsed state and an expanded use state. In the collapsed state, the single-use container should be rather flat in order to save storage space. The background of this requirement is that in a typical medical environment such as a hospital, many of these single-use containers are used on any given day.

Therefore, many single-use containers need to be kept in storage, often close to patients. If all these single-use containers would be stored in their expanded use state, a very large storage space would be required. Therefore, it is generally desirable that such single-use containers can be collapsed and stored in a collapsed or nestable form.

At the time of usage, it should further be easy to transform the single-use container from the collapsed state into the expanded and structurally strong use state. This requirement makes the challenge of providing a user friendly form extra challenging.

OBJECT OF THE INVENTION

It is an object of the present invention to provide a single-use container, in particular for holding body fluids, wherein the single-use container can be stored in a collapsed state and can be expanded to a use state with ease, wherein the single-use container provides increased comfort to a user through ergonomic shape of the container.

Furthermore, it is an object that the expanded container is strong and sturdy enough to be easily handled and fulfil the role of urinal or body fluid container. Providing such relatively high structural strength with an easy to expand container from the flat state is a specific objective of this invention.

It is an object of the present invention to provide a single-use urinal which can be stored in a collapsed state and can be expanded to a use state with ease and which provides increased comfort to a user, in particular when lying in a bed, more in particular when lying in a supine position.

It is an object of the present invention to provide a single-use container for body fluids which can be manufactured with less material than single-use containers of the prior art.

It is an object of the present invention to provide for a single-use container that can be produced from a flat blank at high manufacturing speeds and low production costs.

It is an object of the present invention to provide for an easy to expand, single-use container that provides for high structural strength.

It is an object of the present invention to provide a single-use container for body fluids which does not require any oil-based wax water-proofing treatment.

It is an object of the present invention to provide a single-use container which is a suitable alternative for the prior art.

SUMMARY OF THE INVENTION

In order to achieve at least one object, the invention provides a single-use container manufactured from sheet material, the single-use container comprising:
  a base on which the single-use container can stand,
  a front wall, a right wall, a left wall and a rear wall which extend upward from the base,
  an upper end,
  wherein the right wall and left wall are connected to the front wall and rear wall via fold lines which extend upwardly from the base and wherein side wall fold lines extend over the right and left wall upwardly from the base,
  wherein a central base fold line extends along the base,
  wherein the single-use container is configured to be transformed from a collapsed state to an expanded state by unfolding the side wall fold lines and folding the fold lines, and unfolding the base about the central base fold line, thereby forming the right and left wall and expanding the collapsed single-use container into an expanded state.

The single-use container has a number of advantages: it prevents pathogen transmission in healthcare settings, it is easy and cost-effective to manufacture, easy to store, easy to use, structurally strong in its expanded state.

In an embodiment, the front wall and the rear wall are convex, and wherein the right wall and left wall are concave. Due to its shape it provides improved comfort to the user In an embodiment, the right wall and left wall are curved substantially in a single plane. It will be noted that in this respect the right wall and left wall of the container of the present invention are quite different than the right wall and left wall of the container of D1. The right wall and left wall of the container of D1 are curved in two planes of curvature.

In an embodiment, the curved front right edge and the curved right rear edge define a right plane, and wherein the right wall of the container lies either on the right plane, or outside of the right plane, and the curved front left edge and the curved left rear edge of the container define a left plane, wherein the left wall of the container lies either on this left plane or outside of this left plane. This results in a more ergonomic shape, and is quite different from the right wall and left wall of D1, which lie inwards with respect to this right plane and left plane, resulting in a less ergonomic shape, because the legs of the user will be pushed against the edges of the front wall and rear wall, in particular at the upper portion thereof.

In an embodiment in front view the single-use container may have a waist section, the waist section having a front width W1 which is smaller than a front width W2 at the base and smaller than a front width W3 at the upper end, wherein in particular the front width gradually decreases from the base to the waist section and gradually increases from the waist section to the upper end.

In an embodiment in side view the single-use container may have a side width W4 which reaches a maximum at the level of the waist section, the side width at the waist section being greater than the side width W5 at the base and greater than the side width W6 at the upper end, wherein the side width in particular gradually increases from the base to the waist section and gradually decreases from the waist section to the upper end.

In an embodiment the front wall and rear wall meet at the upper end and wherein the left wall and the right wall do not meet at the upper end.

In an embodiment the base may have a square or rectangular shape. The base may be flat and form a surface on which the container can stand.

In an embodiment the single-use container may comprise a curved front right edge which extends upward from a front right corner of the base, a curved front left edge which extends upward from a front left corner of the base, a curved right rear edge which extends upward from a rear right corner of the base and a curved left rear edge which extends upward from a rear left corner of the base, wherein the curved right front edge and the curved right rear edge meet at the upper end and wherein the curved left front edge and the curved left rear edge meet at the upper end.

In an embodiment the single-use container may form a single-use urinal, wherein the front wall or at least one side wall comprises:
 a pee opening, or
 a pee opening area having a perimeter which is frangible and at least partially weakened and is configured to be broken to remove the pee opening area or to fold the pee opening area inward or outward in order to form the pee opening.

There may be a small finger hole opening which allows air into the container as the sides are squeezed and the container pops from the collapsed state into it's expanded, in-use shape.

In an embodiment the pee opening or pee opening area may be provided at the level of the waist section.

In an embodiment the single-use container may comprise:
 a first pee opening or pee opening area in the front wall and
 a second pee opening or pee opening area in the rear wall, wherein the second pee opening or second pee opening area has a different size or shape than the first pee opening or pee opening area.

In an embodiment the sheet material may be cardboard, multi-layered 'cupstock', or Bagasse sheet carton.

The base may be four sided, in particular square, rectangular or trapezoid.

In an embodiment the upper end is openable, allowing the single-use container to be used as a body fluid container, medical container or sick bag.

In an embodiment, the base is formed by a plurality of base portions folded over one another and connected to one another via an adhesive connection, each base portion being integrally connected via a respective base fold line to one of the walls extending upwardly from the base.

In an embodiment the base may comprise:
 a left base portion connected to the left wall via a left base fold line,
 a front base portion connected to the front wall via a front base fold line,
 a right base portion connected to the right wall via a right base fold line,
 a rear base portion connected to the rear wall via a rear base fold line,
 wherein the base has four corners wherein a diagonal base fold line extends from each corner, wherein the diagonal base fold lines interconnect the left base portion, the front base portion, the right base portion and the rear base portion, wherein the left base portion, the front base portion, the right base portion and the rear base portion are folded onto one another.

In an embodiment the left base portion and the right base portion may comprise overlap portions which are glued against an inner side of the front and rear base portion, and wherein the front and rear base portion including the overlap portions and the diagonal base fold lines are folded over and glued against an outer side of the left and right base portion.

Collapsed Single-Use Container

The present invention further relates to a collapsed single-use container being configured to be expanded into the single-use container according to any of the preceding claims, the collapsed single-use container being manufactured from sheet material and comprising:
 a base section folded onto itself along a central base fold line,
 a front part comprising:
  a central front part which defines the front wall of the single-use container which is to be formed,
  a left front part, which defines a forward part of the left wall of the single-use container which is to be formed, a right front part, which defines a forward part of the right wall of the single-use container which is to be formed, a rear part comprising:
  a central rear part which defines the rear wall of the single-use container which is to be formed,
  a left rear section which defines a rearward part of the left wall of the single-use container which is to be formed,
  a right rear section which defines a rearward part of the right wall of the single-use container which is to be formed, an upper end, wherein the central front part is connected to the left front part and right front part via fold lines, and wherein the central rear part is connected to the left rear part and right rear part via fold lines, wherein side wall fold lines extend over the right and left wall and form a right edge and a left edge of the collapsed single-use container, wherein a central base fold line extends along the base section, wherein the collapsed single-use container is configured to be transformed from the collapsed state to an expanded state by pushing the right edge and the left edge of the collapsed single-use container inward, thereby unfolding the side wall fold lines, forming the right and left wall and unfolding the base section into a base.

The collapsed single-use container can be expanded into the (expanded) single-use container according to the invention and provides the advantages associated with the single-use container.

In an embodiment the left front part may be delimited from the central front part by a left front folding line, and wherein the right front part is delimited from the central front part by a right front folding line, wherein the left and right front folding lines are curved and define a waste section in the central front part, the waste section having a smaller width W3 than a width W4, W5 at a lower portion of the central front part and at an upper portion of the central front part, wherein the left rear part is delimited from the central rear part by a left rear folding line, wherein the right rear part is delimited from the central rear part by a right rear folding line, wherein the left and right rear folding lines are curved and define a waste section in the central rear part, the waste section having a smaller width than a lower portion of the central rear part and an upper portion of the central rear part
  wherein the left front part and left rear part together are deformable into the left wall of the single-use container by pushing a left edge of the collapsed single-use container inward, and wherein the right front part and right rear part together are deformable into the right wall of the single-use container by pushing a right edge of the collapsed single-use container inward, thereby expanding the collapsed single-use container into an expanded state.

In an embodiment, in front view:
  the right edge comprises an upper right edge and a lower right edge, and
  the left edge comprises an upper left edge and a lower left edge,
  wherein due to the fact that the base section is folded onto itself:
    the lower right edge comprises a front lower right edge part and a rear lower right edge part and
    the lower left edge comprises a front lower left edge part and a rear lower left edge part,
  wherein the upper right edge, the front lower right edge part and the rear lower right edge part form folding lines which can be pushed inwards, thereby forming the right wall during the expanding of the collapsible container, and
  wherein the upper left edge, the front lower left edge part and the rear lower left edge part form folding lines which can be pushed inwards, thereby forming the left wall during the expanding of the collapsible container.

In an embodiment, the upper right edge and the lower right edge may extend at an angle α of 120-160 degrees relative to one another and define a right side corner, wherein the upper left edge and the lower left edge extend at an angle α of 120-160 degrees relative to one another and define a left side corner.

This shape is quite different from the shape of the collapsed container of D1 as shown in FIG. 5E of D1. The bottom parts of the sidewalls which are to be pushed inwards have a different shape than in the present invention. The sidewalls in FIG. 5E have a bottom edge which is parallel with the bottom edge of the base and which extends outwardly away from the bottom edge of the base. In the present invention, this is different because in the collapsed container the lower edges 85 of the sidewalls extend outwardly and upwardly away from the corners of the base. See for instance FIG. 12 of the present application.

In an embodiment, in front view the lower right edge and the lower left edge may extend at an angle β of 120-160 degrees relative to a lower base edge of the collapsed single-use container.

In an embodiment, the base section may comprise:
  a left base portion connected to the left wall via a left base fold line,
  a front base portion connected to the front wall via a front base fold line,
  a right base portion connected to the right wall via a right base fold line,
  a rear base portion connected to the rear wall via a rear base fold line,
  wherein the base has four corners wherein a diagonal base fold line extends from each corner, wherein the diagonal base fold lines interconnect the left base portion, the front base portion, the right base portion and the rear base portion.

In an embodiment, the left base portion and the right base portion may comprise overlap portions which are glued against an inner side of the front and rear base portion, and wherein the front and rear base portion including the overlap portions and the diagonal base fold lines are folded over and glued against an outer side of the left and right base portion.

Blank

The present invention further relates to a blank for manufacturing the collapsed single-use container according to the invention, the blank comprising:
  a base section,
  a wall section, and
  an upper end section,
  wherein the base section is delimited from the wall section by a base perimeter fold line,
  wherein the wall section comprises a front wall zone, a rear wall zone, a right wall zone and a left wall zone,
  wherein side wall fold lines extend over the right and left wall zone.

With the blank the single-use container according to the invention can be made.

In an embodiment, the base perimeter fold line may extend across the blank from a left side of the blank to a right side of the blank, wherein the base perimeter fold line comprises a left base fold line, a front base fold line, a right base fold line, and a rear base fold line, wherein the base section comprises:
a left base portion connected to the left wall zone via the left base fold line,
a front base portion connected to the front wall zone via the front base fold line,
a right base portion connected to the right wall zone via the right base fold line,
a rear base portion connected to the rear wall zone via the rear base fold line, wherein the blank has four corner locations configured to form the four corners of the single-use container, wherein a diagonal base fold line extends from each corner location, wherein the diagonal base fold lines interconnect the left base portion, the front base portion, the right base portion and the rear base portion.

In an embodiment, the left base portion and the right base portion may comprise overlap portions configured to be glued against an inner side of the front and rear base portion, and wherein the front and rear base portion including the overlap portions and the diagonal fold lines are configured to be folded over and glued against an outer side of the left and right base portion.

In an embodiment, the blank may comprise a side connection flap extending along a curved left edge or right edge of the wall section, the side connection flap being configured to be connected to an opposite side wall region for forming a circumferential side wall of the single-use container.

In an embodiment, the front wall zone and the rear wall zone may have straight upper ends and straight lower ends.

In an embodiment, the overlap portions are elongated and extend at substantially right angles to the base perimeter fold line.

The present invention further relates to a method of manufacturing the collapsed single-use container according to the invention, the method comprising:
interconnecting the front wall zone, the rear wall zone, the right wall zone and the left wall zone by an adhesive connection into a circumferential wall,
folding the left base portion, the front base portion, the right base portion and the rear base portion onto one another to form the base section,
wherein the overlap portions of the right and left base portion are attached to the inner sides of the front and rear base portions by adhesive connections, and
wherein the front and rear base portions including the overlap portions and the diagonal fold lines are folded over the outer sides of the right and left base portions and attached thereto by adhesive connections.

The method provides the same advantages as the collapsed single-use container and the expanded single-use container.

The present invention further relates to a method of manufacturing the collapsed single-use container according to the invention from the blank according to the invention, the method comprising interconnecting the front wall zone, the rear wall zone, the right wall zone and the left wall zone into a circumferential wall by an adhesive connection.

The method may comprise folding a plurality of base portions over one another and connecting the base portions to one another via an adhesive connection.

The method may comprise folding the left base portion, the front base portion, the right base portion and the rear base portion onto one another to form the base section, wherein the overlap portions of the right and left base portion are attached to the inner sides of the front and rear base portions by adhesive connections, wherein the front and rear base portions including the overlap portions and the diagonal fold lines are folded over the outer sides of the right and left base portions and attached thereto by adhesive connections.

The method may comprise folding the front wall zone, the rear wall zone, the right wall zone and the left wall zone over the fold lines via which they are connected to the base and forming adhesive connections between the front wall zone, the rear wall zone, the right wall zone and the left wall zone, in particular via the adhesive flaps.

The method may comprise pushing a left edge and a right edge of the collapsed single-use container inward, and forming the concave right and left wall and the convex front and rear wall.

Uniquely, with a very simple action from a user, the single-use container can be formed from the collapsed single-use container.

Second Invention

A second invention relates to a single use container having a straight walls. The single use container has several similarities with the first invention and is also made from sheet material. The single use container is also configured for holding body fluids in a medical environment, and can also be expanded from a collapsed state by a simple movement. The single-use, expandable container may also be used as a urinal or as a sick bag.

The straight wall have a disadvantage that the shape of the single use container is less ergonomic, but it has an advantage in that the single use-container is easier to manufacture. Because the fold lines in the blank are all straight, an automated manufacturing process is easier.

Furthermore, the volume of body liquid which this single use-container can hold can be increased relatively easy by increasing the length of the base. Different to the container with two convex and two concave walls, the length of the base can be increased independent from the width of the base.

In order to achieve this objective, the second invention provides a single-use container manufactured from sheet material, the single-use container comprising:
a base on which the single-use container can stand,
a front wall, a right wall, a left wall and a rear wall which extend upward from the base,
wherein the front wall, the right wall, the left wall and the rear wall are straight.

Further, a collapsed single-use container configured to be expanded into the single-use container according to the invention is provided, the collapsed single-use container being manufactured from sheet material and comprising:
a base section folded onto itself along a central base fold line,
a front part comprising:
a central front part which defines the front wall of the single-use container which is to be formed, a left front part, which defines a forward part of the left wall of the single-use container which is to be formed, a right front part, which defines a forward part of the right wall of the single-use container which is to be formed, a rear part comprising:
a central rear part which defines the rear wall of the single-use container which is to be formed,
a left rear section which defines a rearward part of the left wall of the single-use container which is to be formed,
a right rear section which defines a rearward part of the right wall of the single-use container which is to be formed, an upper end where the front part and rear part meet,
wherein the left front part is delimited from the central front part by a left front folding line, and wherein the right front part is delimited from the central front part by a right front folding line, wherein the left and right front folding lines are straight,
wherein the left rear part is delimited from the central rear part by a left rear folding line, wherein the right rear part is delimited from the central rear part by a right rear folding line, wherein the left and right rear folding lines are straight.

The second invention further relates to a blank for manufacturing a collapsed single-use container according to the invention, the blank comprising:
a base section,
a wall section, and
an upper end section,
wherein the base section is delimited from the wall section by a base perimeter fold line,
wherein the wall section comprises a front wall zone, a rear wall zone, a right wall zone and a left wall zone, wherein sides of the wall zones are straight.

Further features of the single-use container, the collapsed single-use container and the blank are disclosed in the description and in the dependent claims.

SHORT DESCRIPTION OF THE FIGURES

The previous and other features and advantages of the present invention will be more fully understood from the following detailed description of exemplary embodiments with reference to the attached drawings. Like reference numerals refer to like parts. The following detailed descriptions and drawings are to be considered exemplary embodiments and should not be limiting the scope of the current invention.

FIGS. 20A to 20C show perspective views of a container of a preferred embodiment configured for use by a male patient.

FIGS. 21, 22, 23 and 24 respectively show a blank, a top view, a front view and a side view of another embodiment of the invention.

FIGS. 25, 26, 27 and 28 respectively show a blank, a top view, a side view and a front view of yet another embodiment of the invention.

Figure 29:
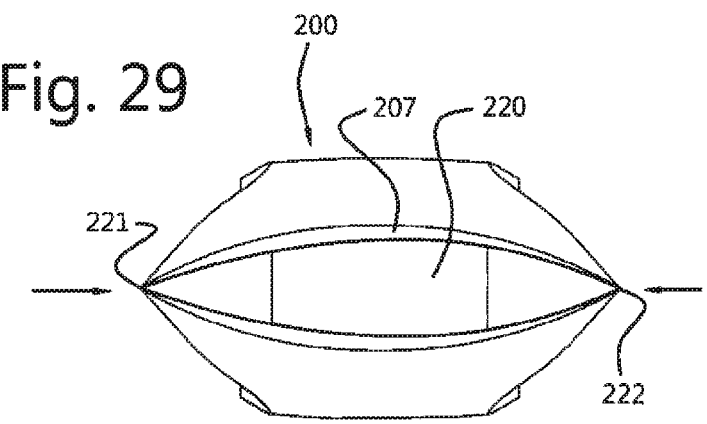
Figure 30:
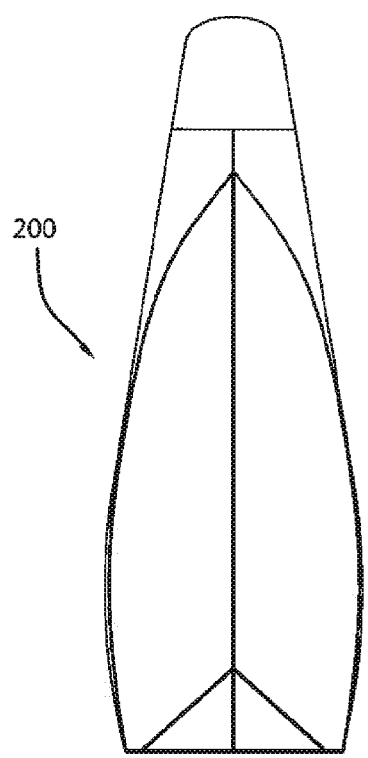
Figure 31:
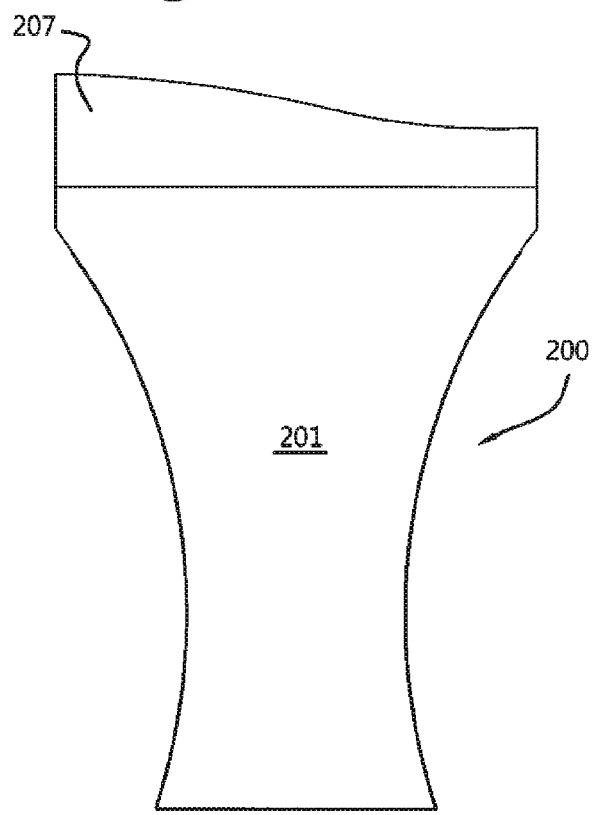

FIGS. 29, 30, 31 show respectively a top view, a side view and a front view of this embodiment in an opened state.

FIGS. 32A-32E shows stages in the use of the single-use expandable container of a preferred embodiment by a male or female.

Figure 33:
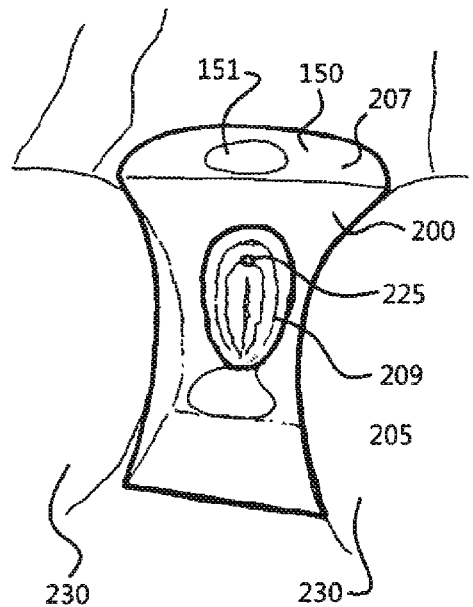

FIG. 33 shows a close-up of the single-use expandable container of a preferred embodiment in use.

Figure 34:
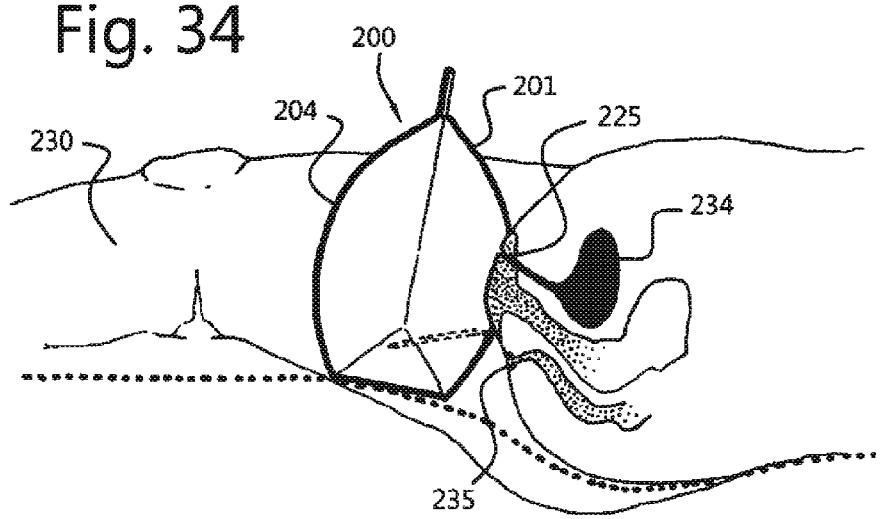

FIG. 34 shows a sectional side view of the use of the single-use expandable container of a preferred embodiment by a female.

Figure 35:
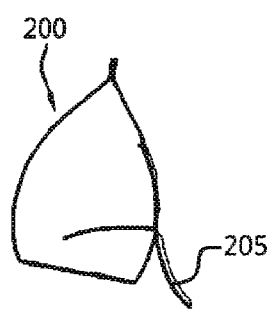

FIG. 35 shows a detail of the single-use container of a preferred embodiment in side view.

Figure 36:
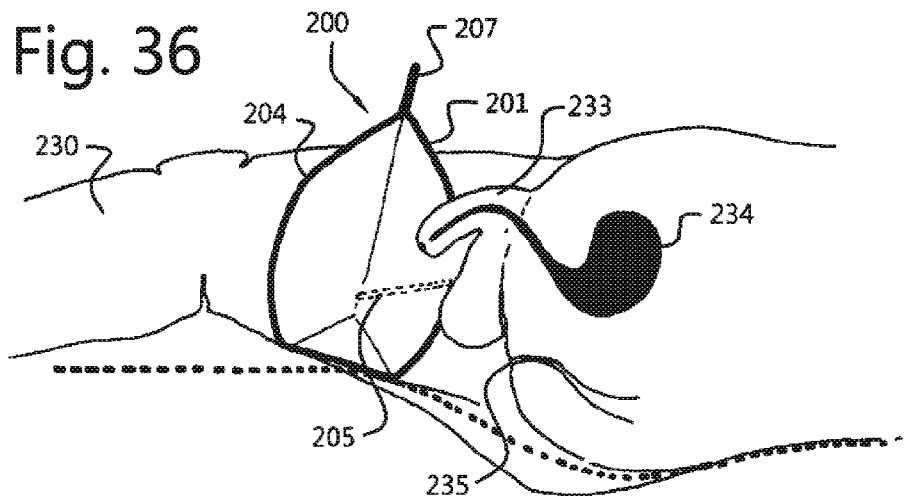

FIG. 36 shows a sectional side view of the use of the single-use container of a preferred embodiment by a male.

Figure 37:
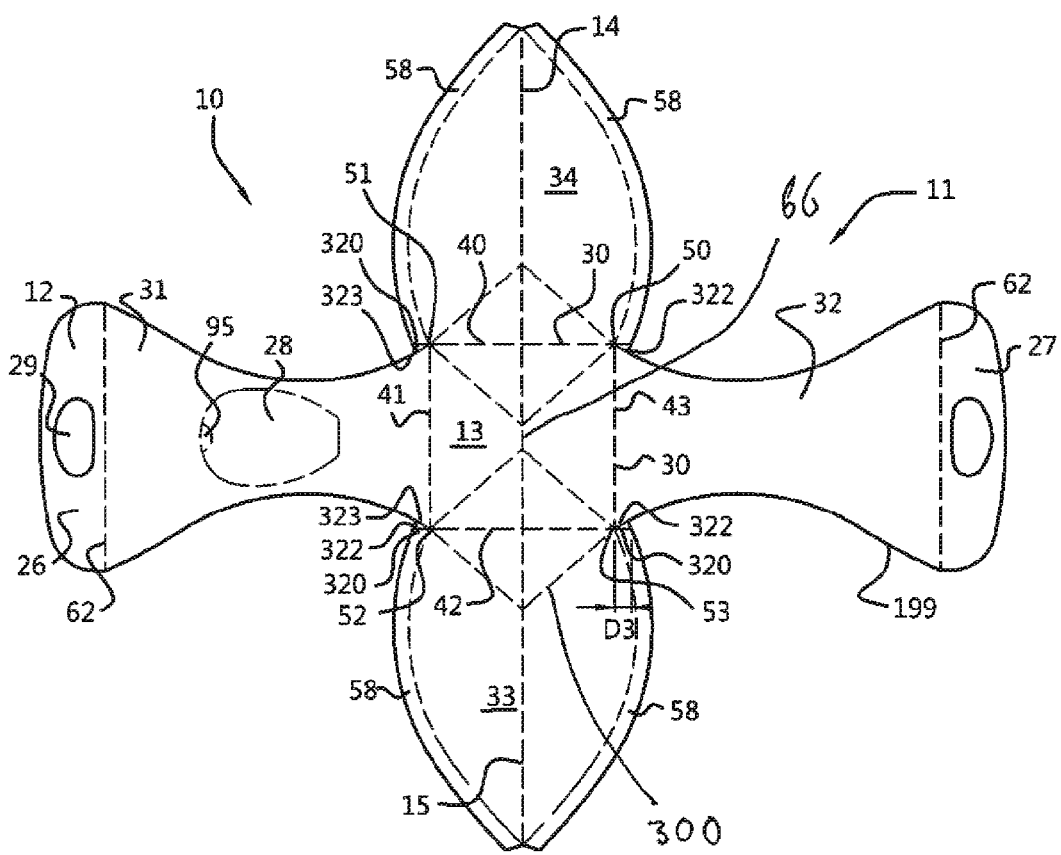

FIG. 37 shows a top view of a blanc according to another embodiment of the invention.

Figure 38:
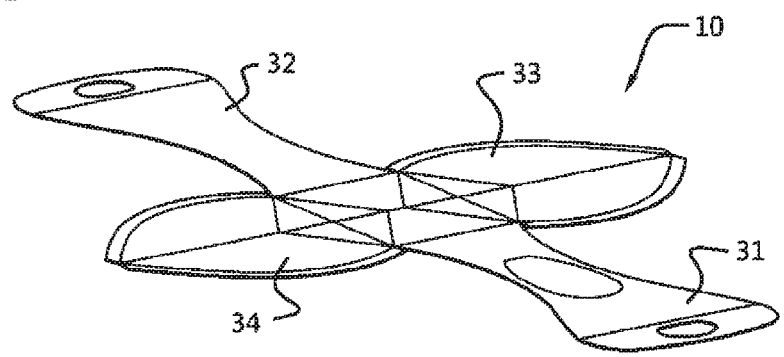
Figure 39:
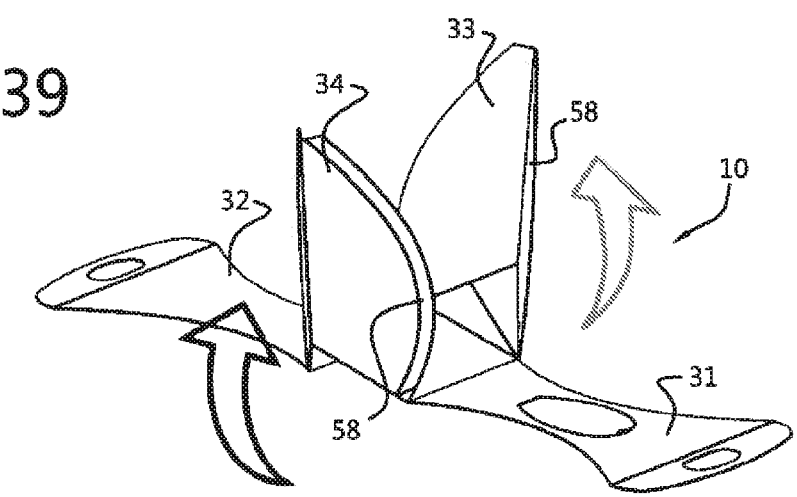
Figure 40:
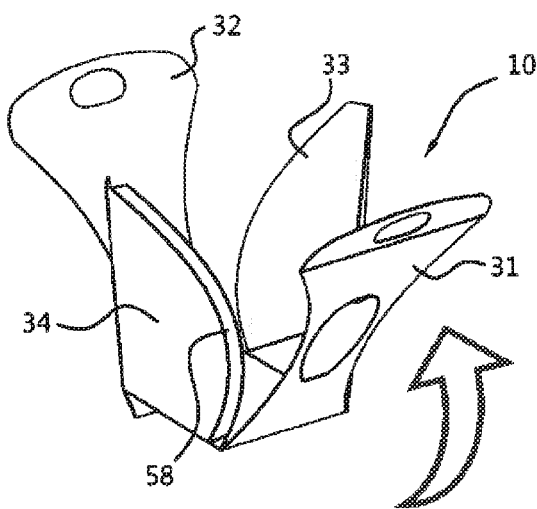

FIGS. 38, 39 and 40 shows isometric views of the folding of the blanc according to FIG. 37.

Figure 41A:
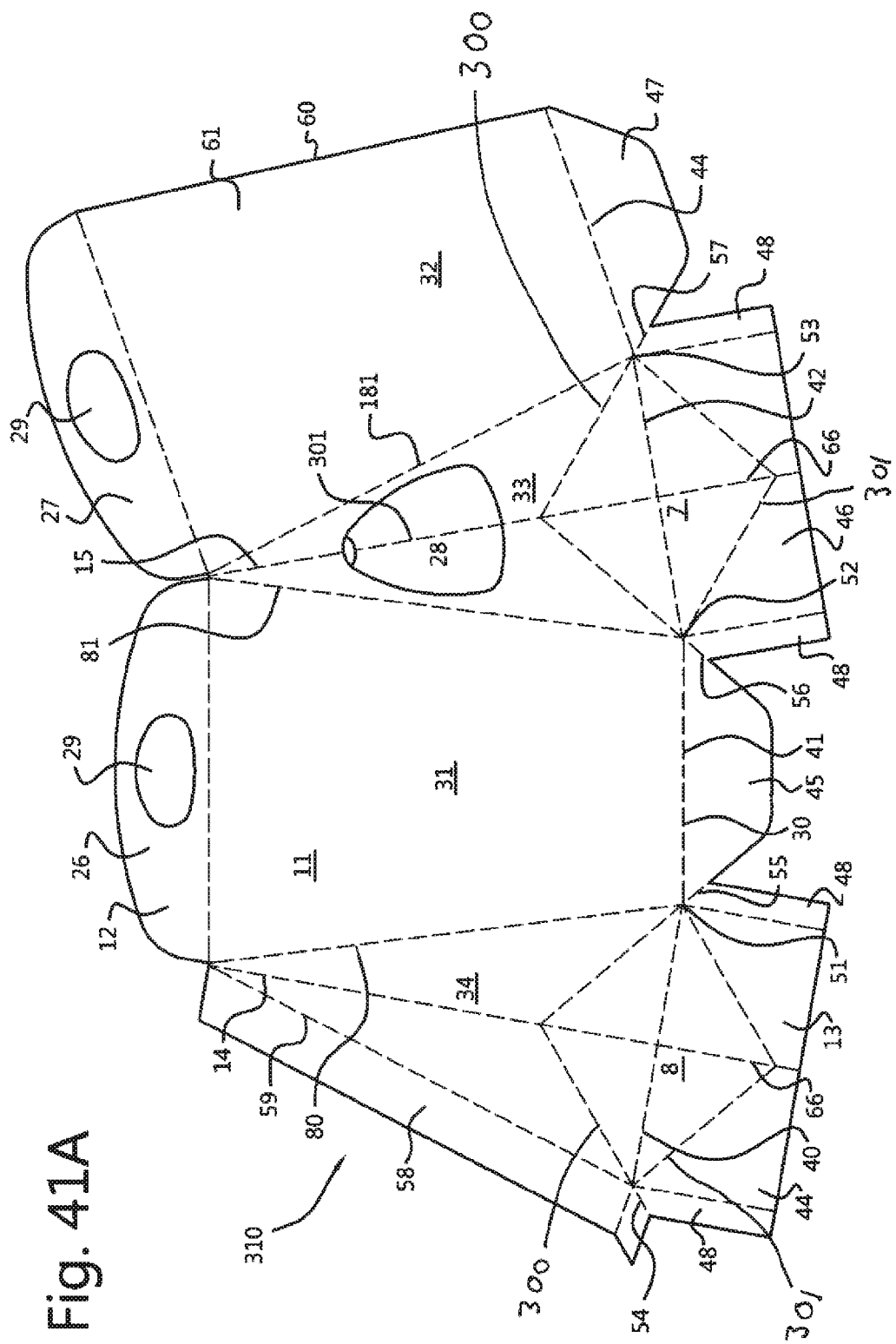
Figure 42B:
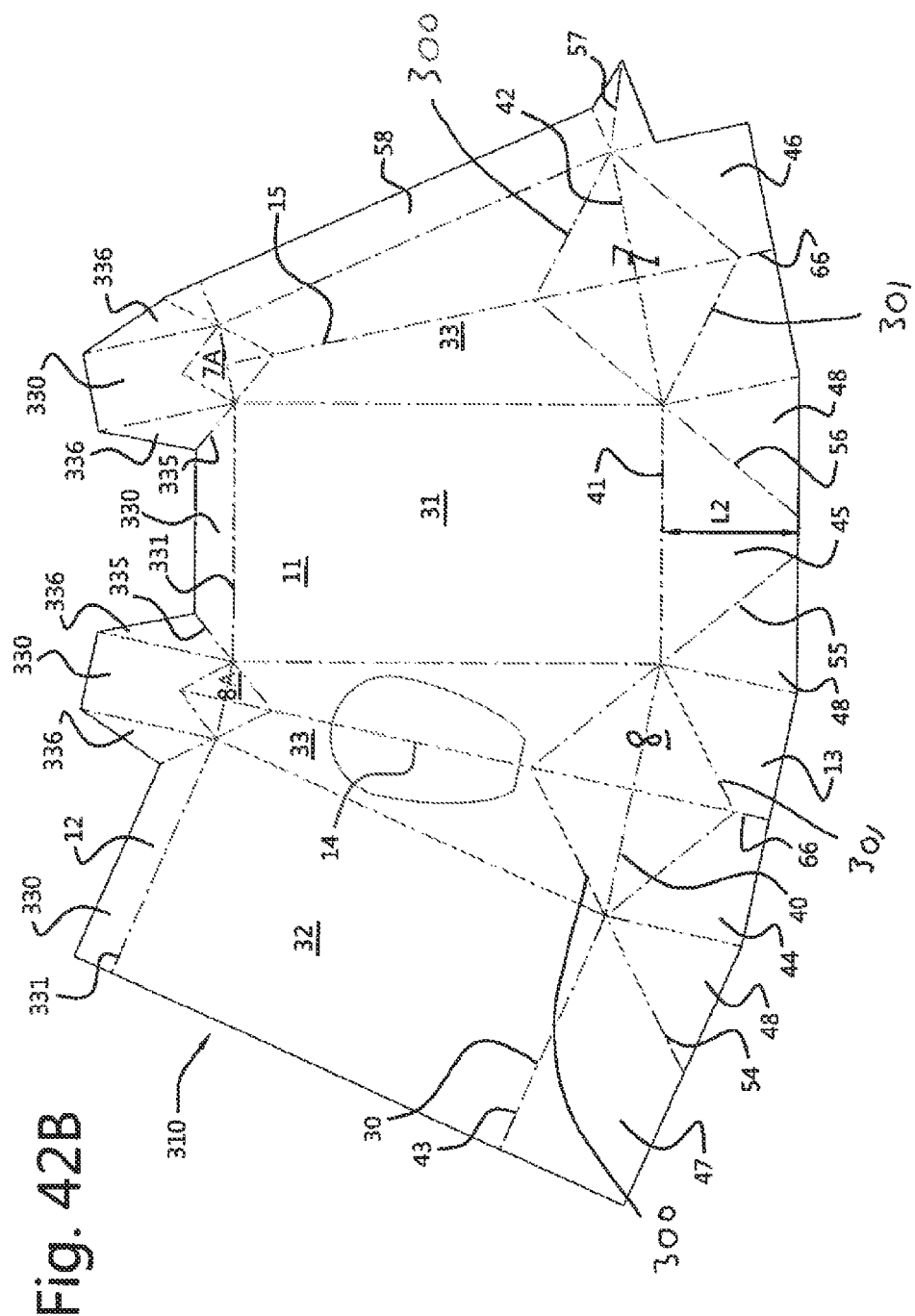

FIGS. 41A, 42A and 42B show blanks of embodiments of a collapsed single-use container according to a second invention.

FIGS. 41B, 41C, 41D show a side view, front view and isometric view of the single use container of the blank of FIG. 41A.

FIGS. 42A1, 42A2, 42A3 show a side view, front view and isometric view of the single use container of the blank of FIG. 42A.

FIGS. 42B1, 42B2, 42B3 show a side view, front view and isometric view of the single use container of the blank of FIG. 42B.

FIGS. 43, 44, 45 show front views of embodiments of a collapsed single-use container according to the second invention.

FIG. 46 shows a side view of the embodiments of FIGS. 43, 44, 45.

FIG. 47 shows a side view of the expanded container of the embodiments of FIGS. 43, 44, 45.

FIGS. 48, 49, 50 show front views of further embodiments of a collapsed single-use container according to the second invention.

FIG. 51 shows a side view of the embodiments of FIGS. 48, 49, 50.

FIG. 52 shows a side view of the expanded container of the embodiments of FIGS. 48, 49, 50.

Figure 55:
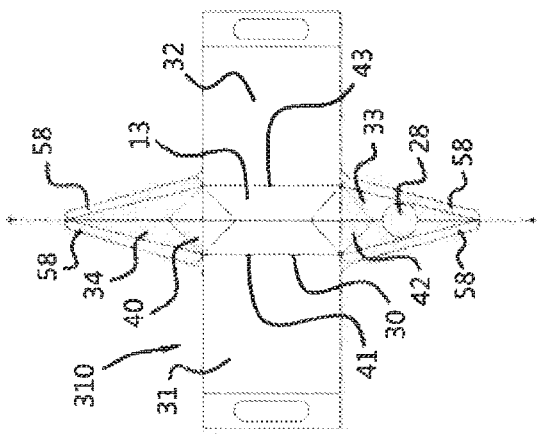
Figure 54:
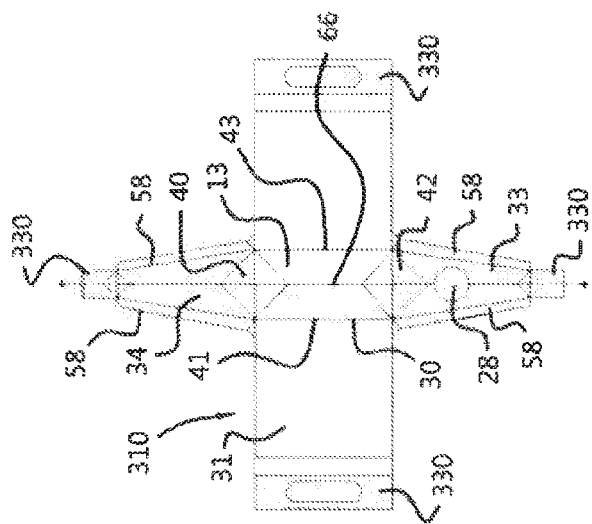
Figure 53:
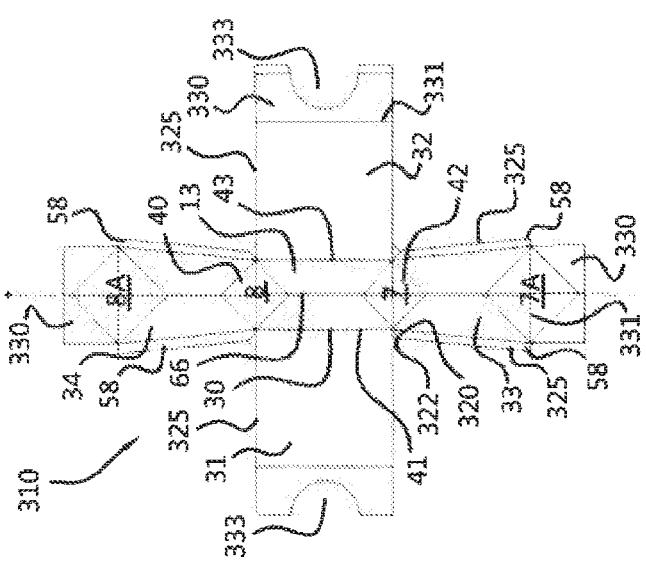

FIGS. 53, 54, 55 show blanks of further embodiments of the second invention.

FIGS. 53A, 54A, 55A show containers of further embodiments of the second invention.

FIG. 56 shows a blank of another embodiment of the second invention

Figure 57:
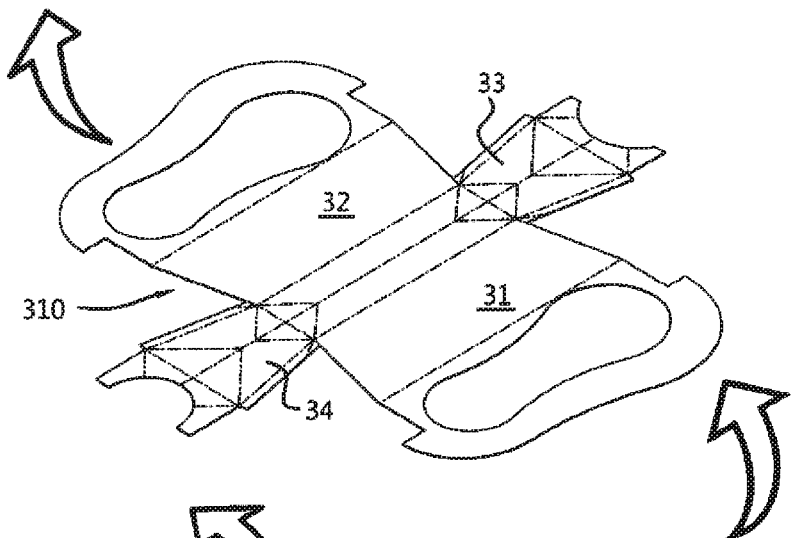

FIGS. 57, 58, 59 ,60 shows steps in forming a collapsed container from the blank of FIG. 57 and forming the expanded container from the collapsed container.

Figure 61:
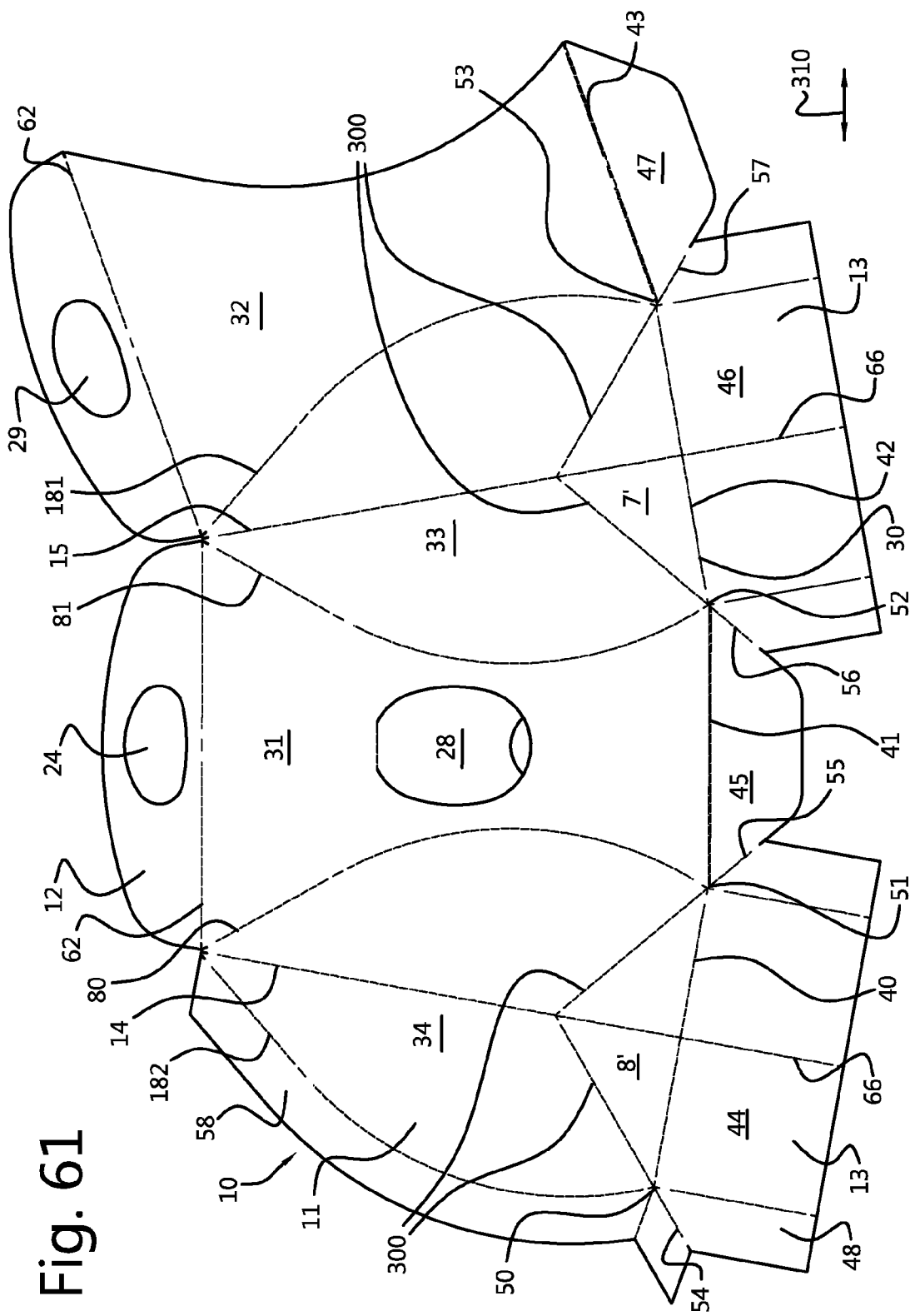

FIG. 61 shows another embodiment of a blank according to the invention.

Figure 62:
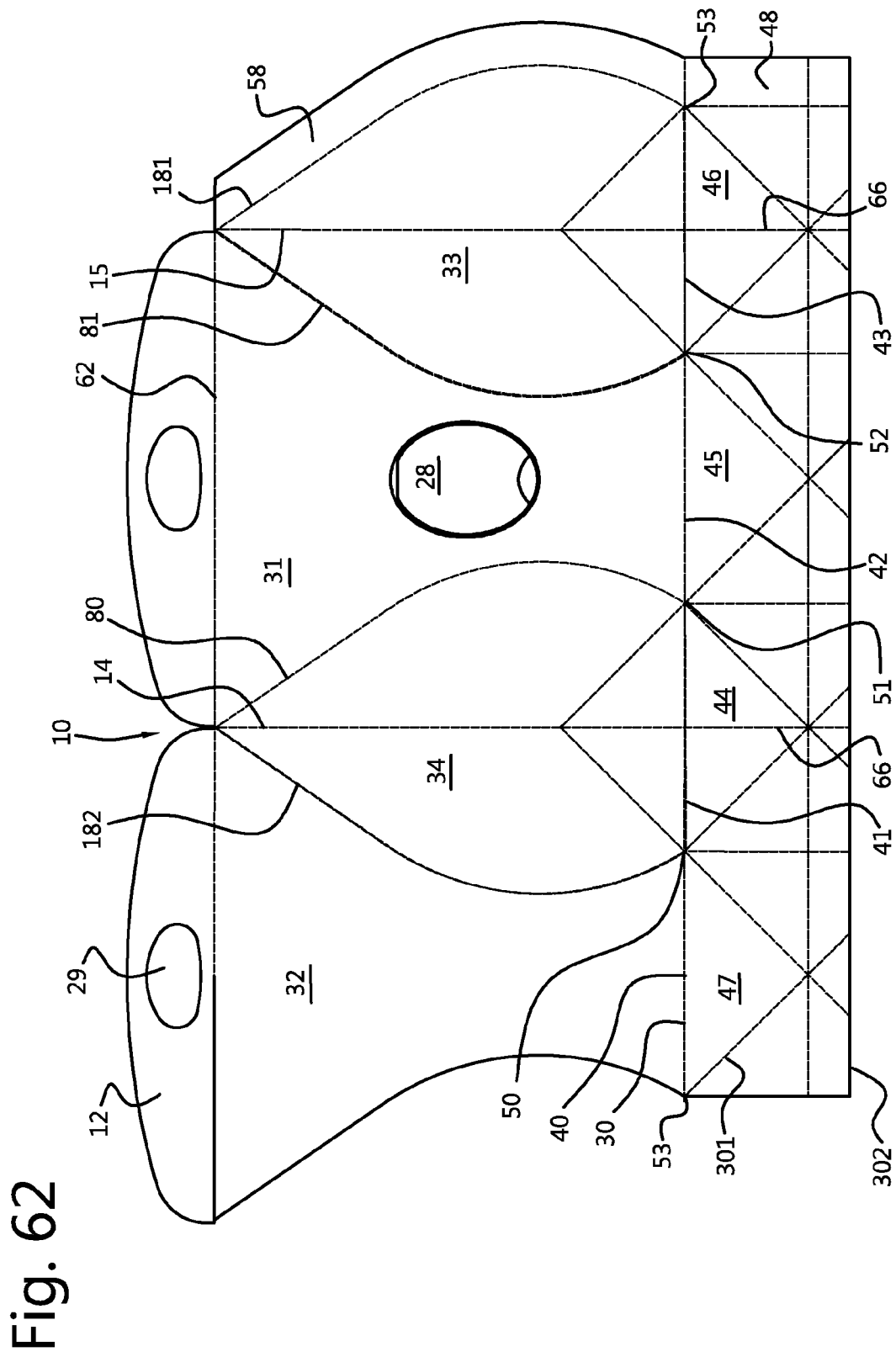

FIG. 62 shows a further embodiment of a blank according to the invention.

Figure 63:
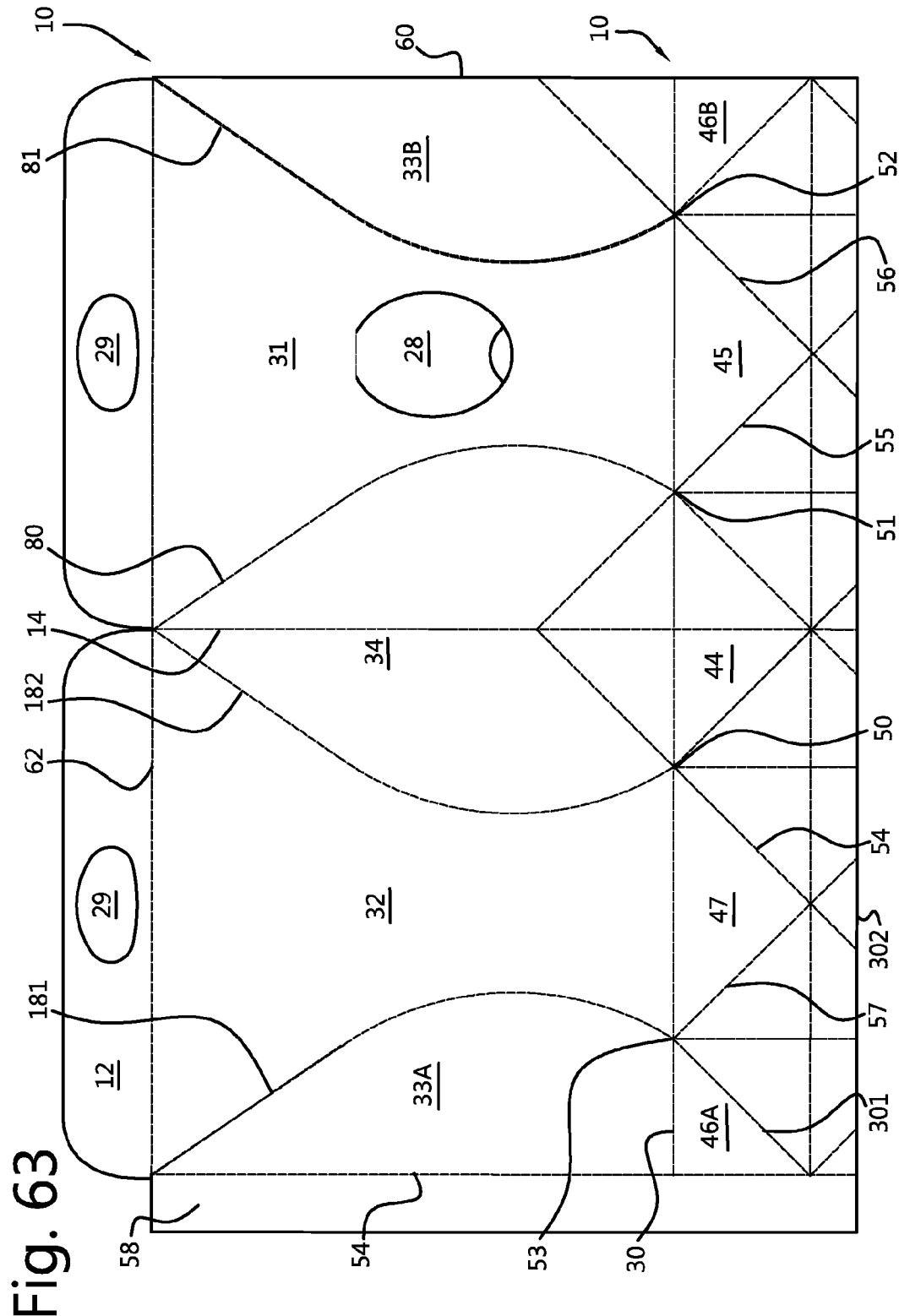

FIG. 63 shows yet another embodiment of a blank according to the invention.

Figure 64:
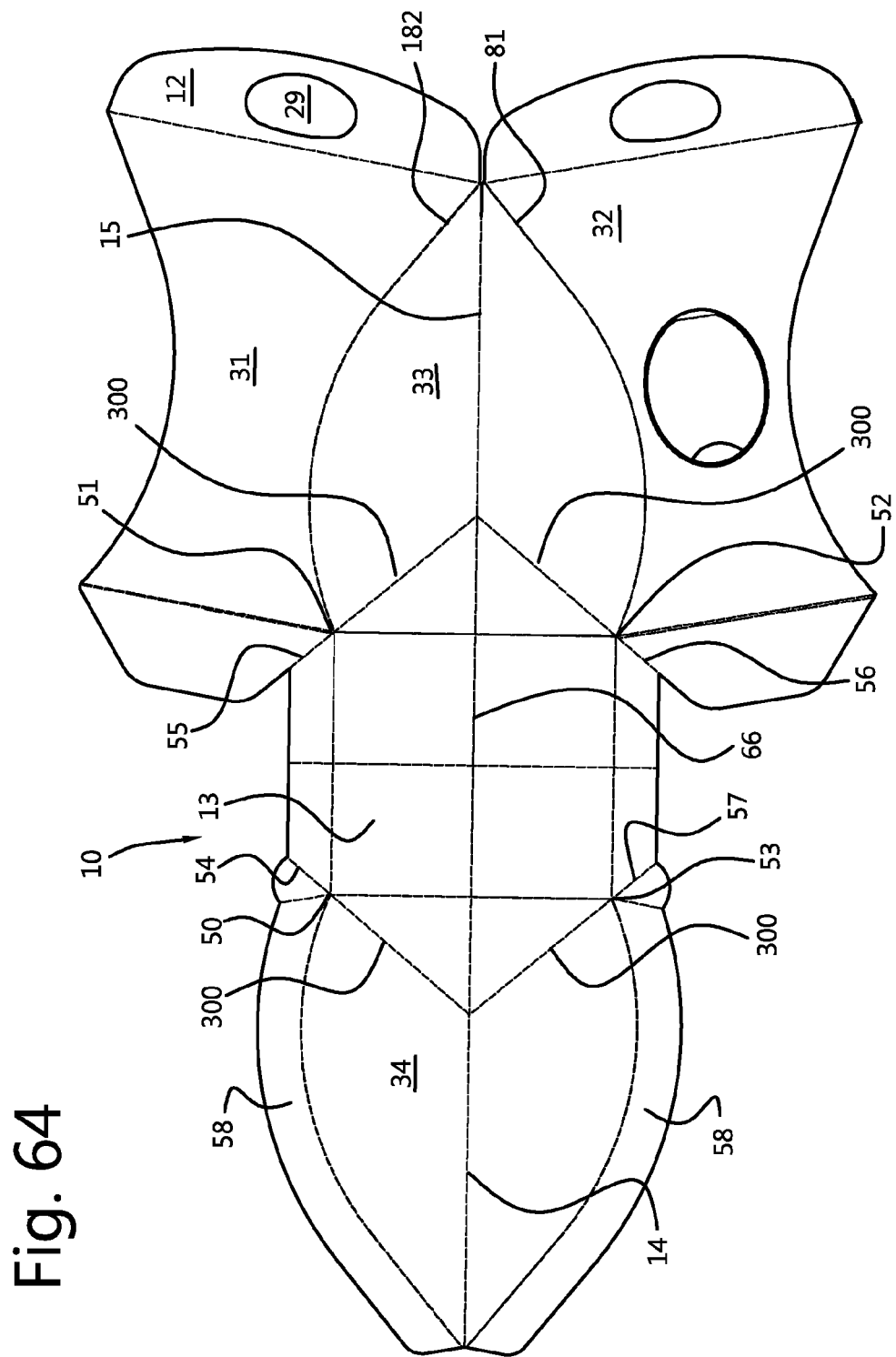

FIG. 64 shows yet a further embodiment of a blank according to the invention.

Figure 65:
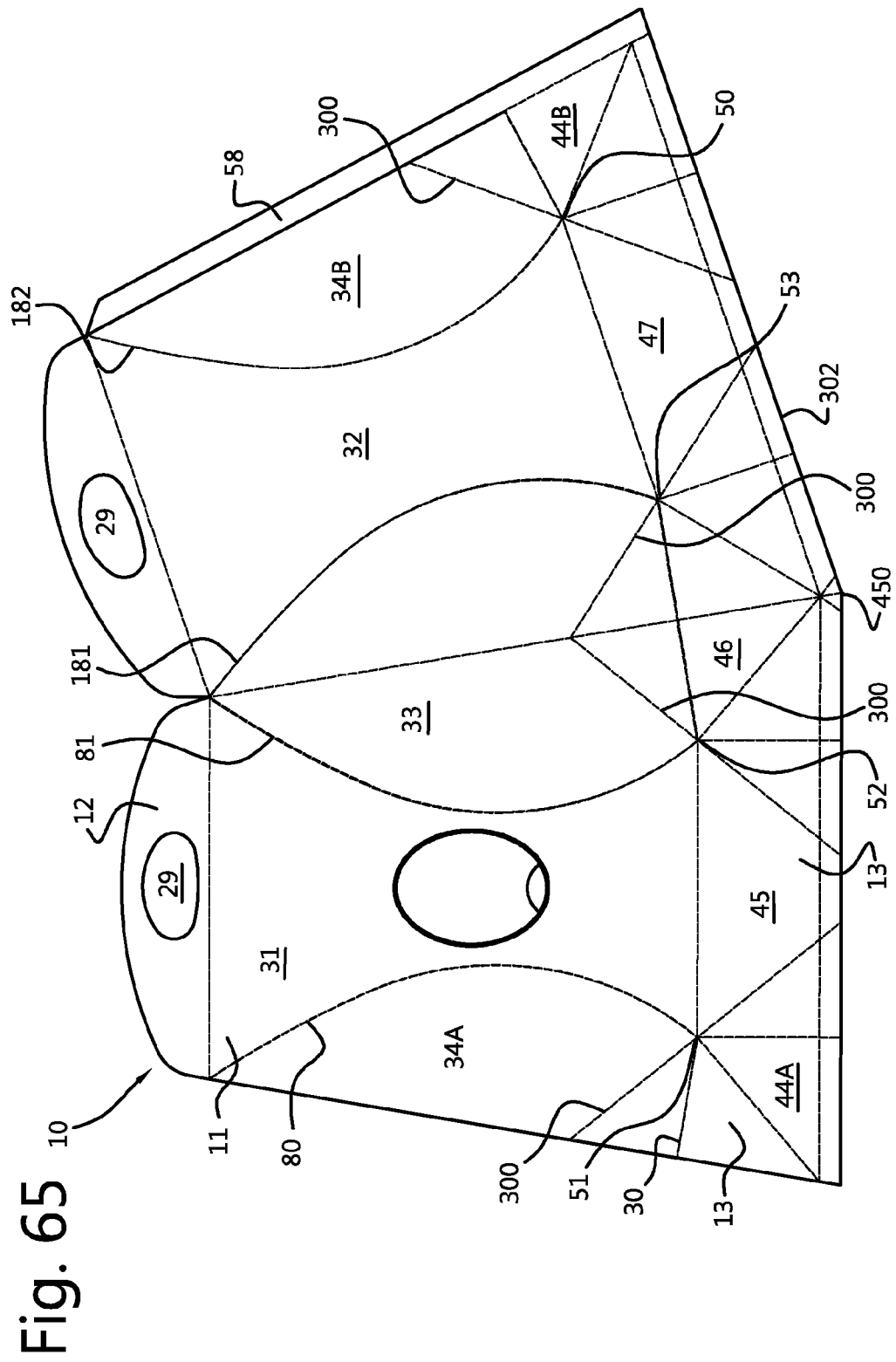

FIG. 65 shows another embodiment of a blank according to the invention.

Figure 66:
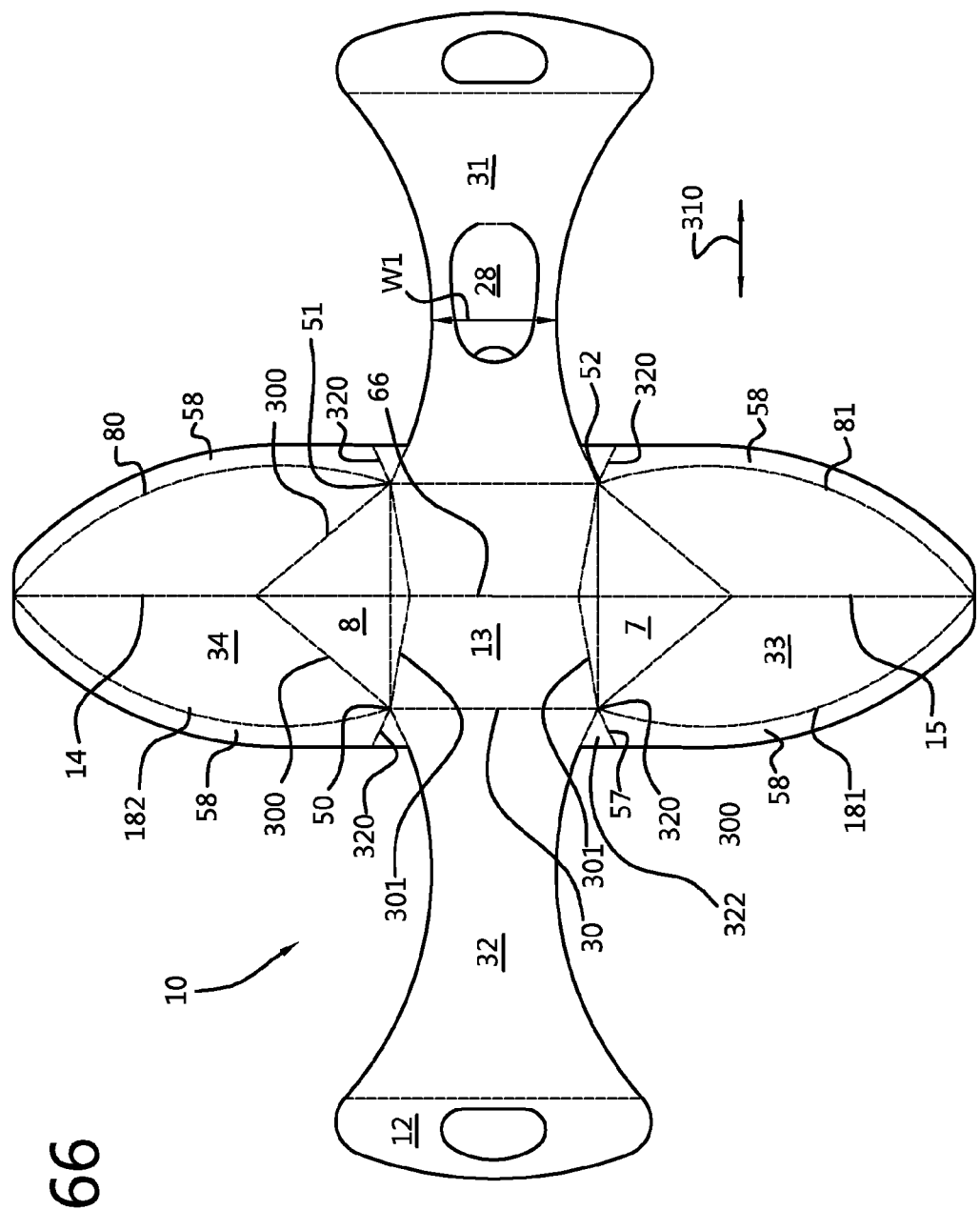

FIG. 66 shows another embodiment of a blank according to the invention.

Figure 67:
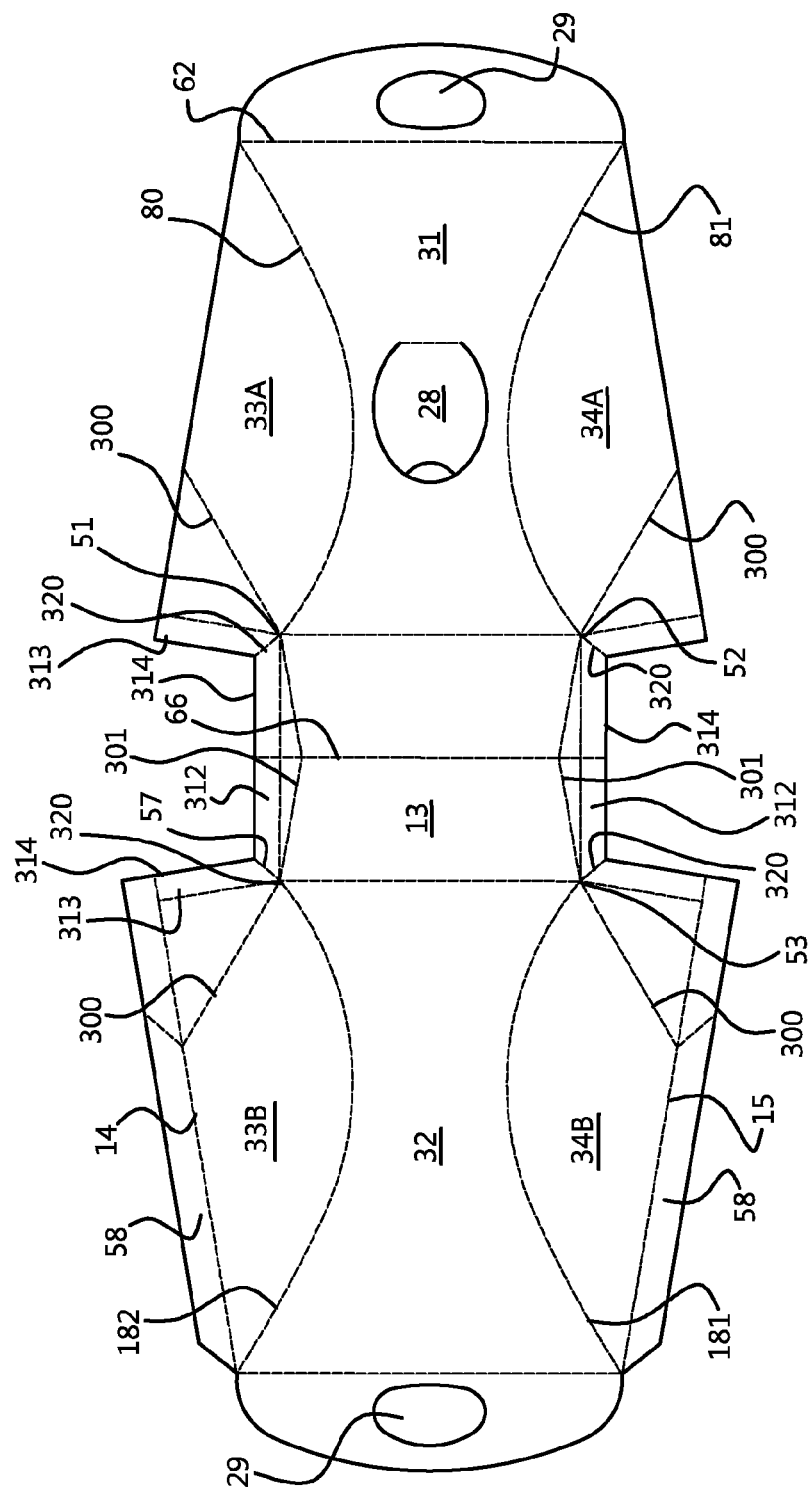

FIG. 67 shows another embodiment of a blank according to the invention.

Figure 68:
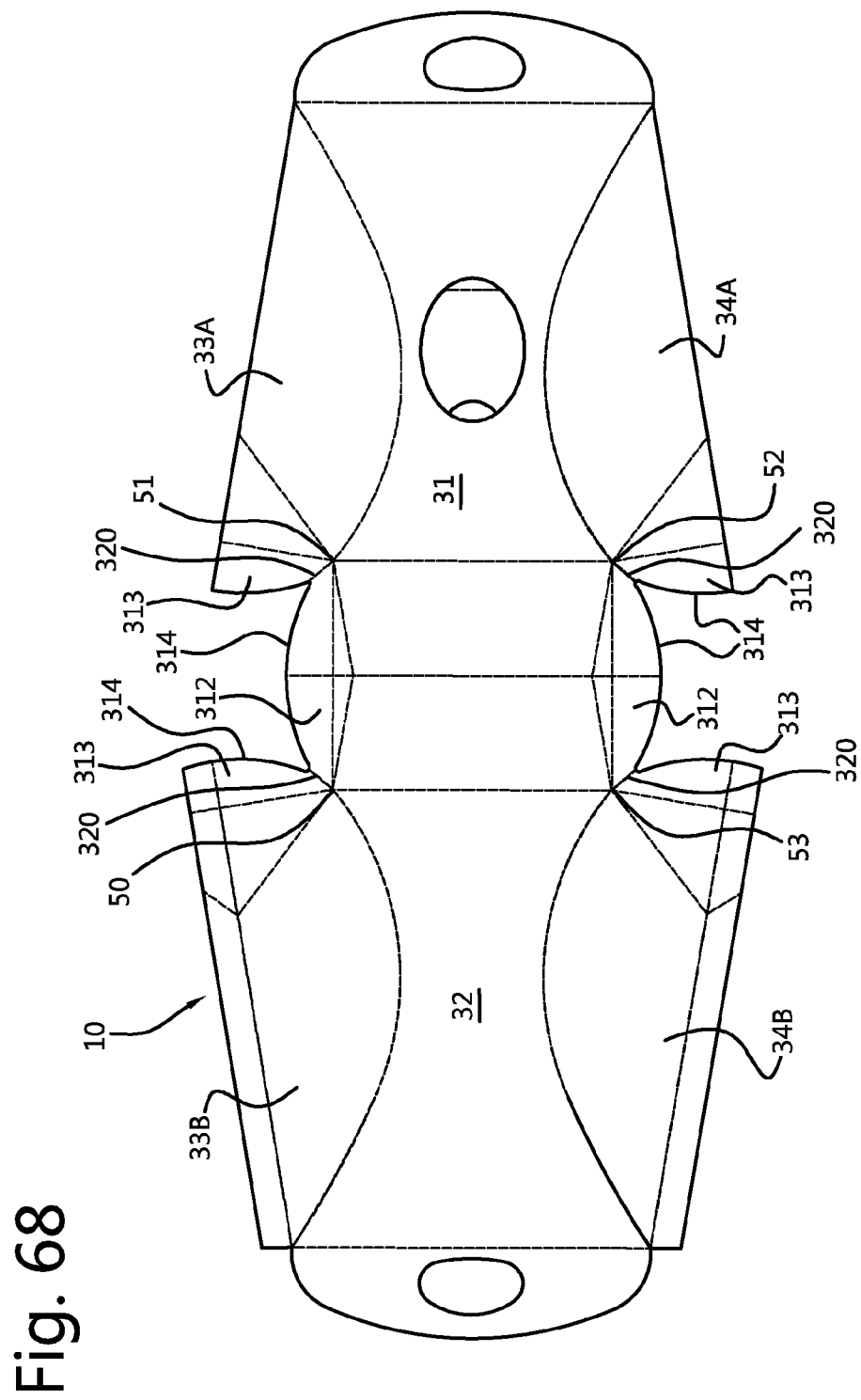

FIG. 68 shows yet another embodiment of a blank according to the invention.

Figure 69:
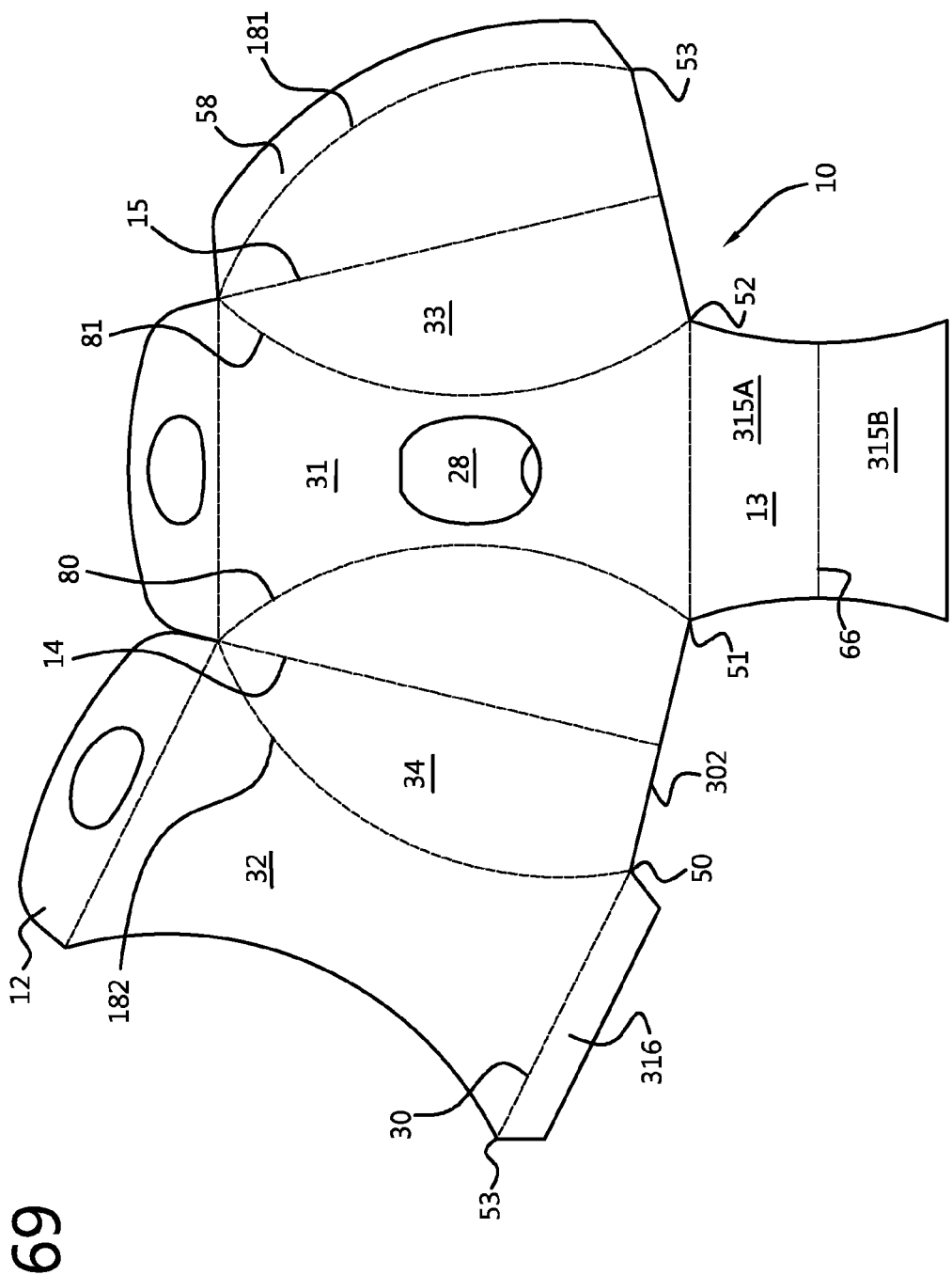

FIG. 69 shows another embodiment of a blank according to the invention.

Figure 70:
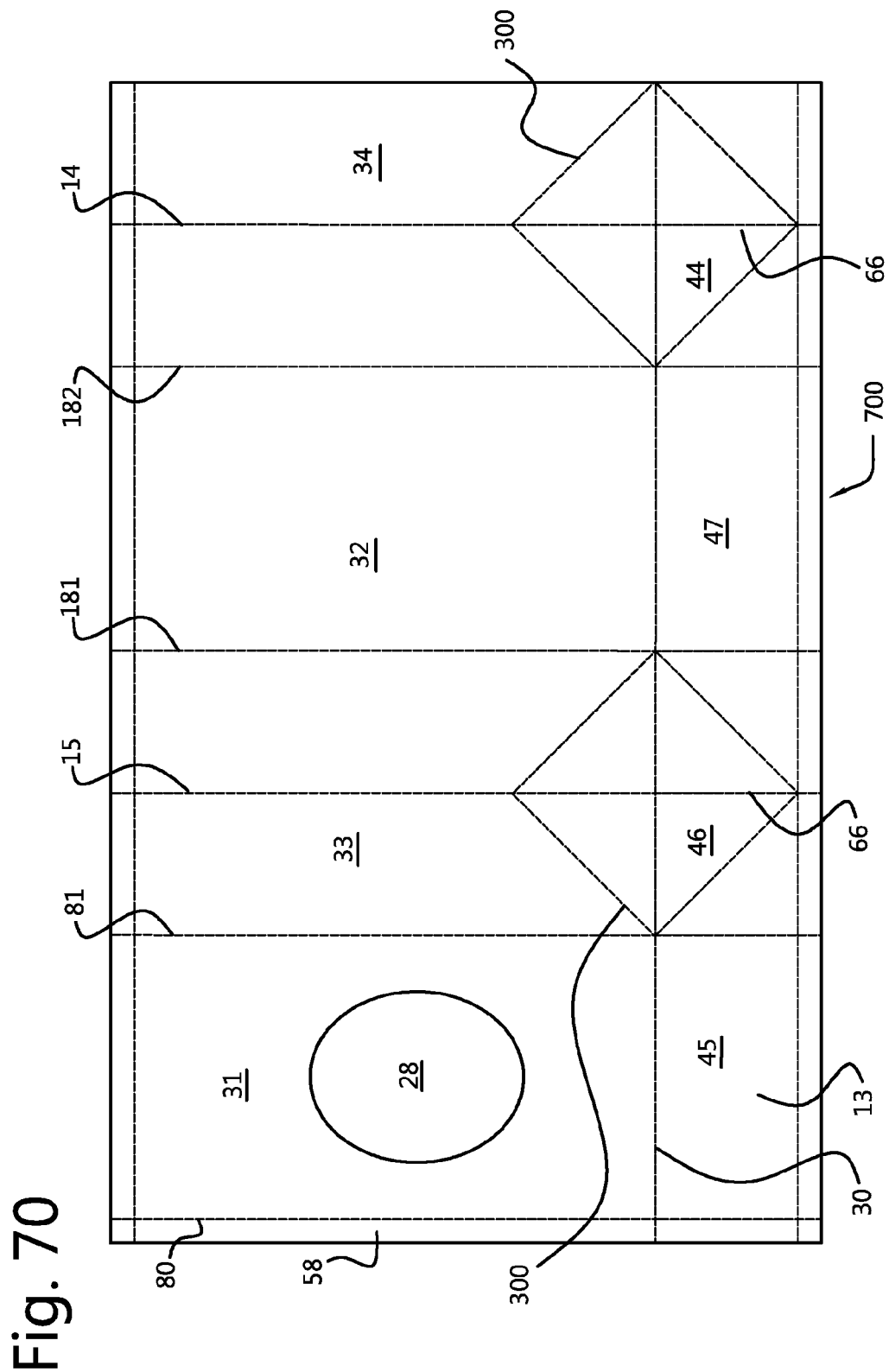

FIG. 70 shows an embodiment of a liner bag according to the invention.

Figure 71:
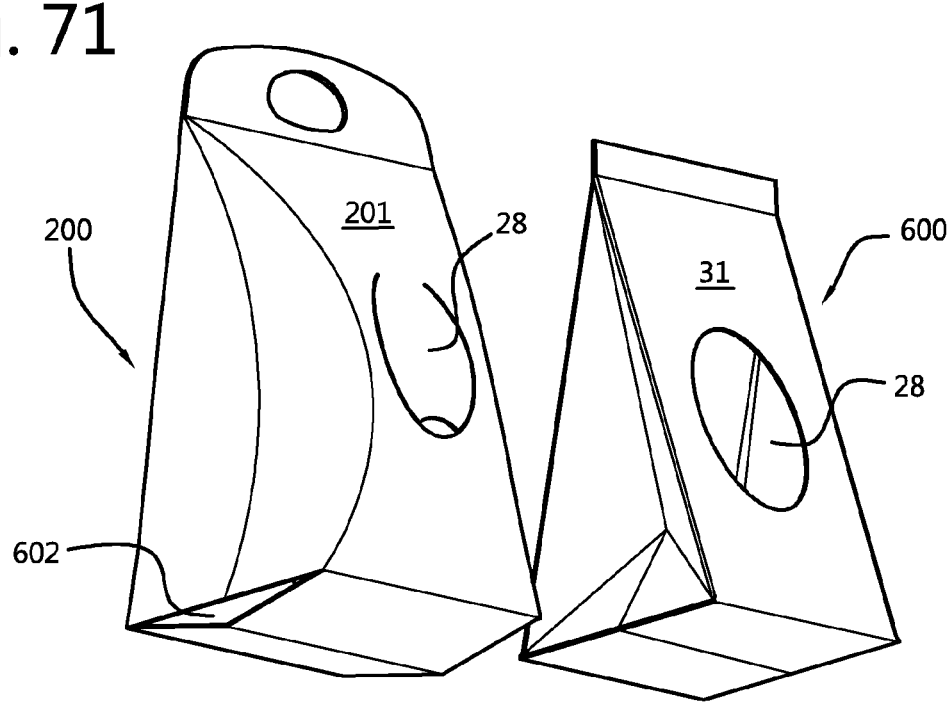

FIG. 71 shows an isometric view of a combination of a container and a liner bag.

Figure 72:
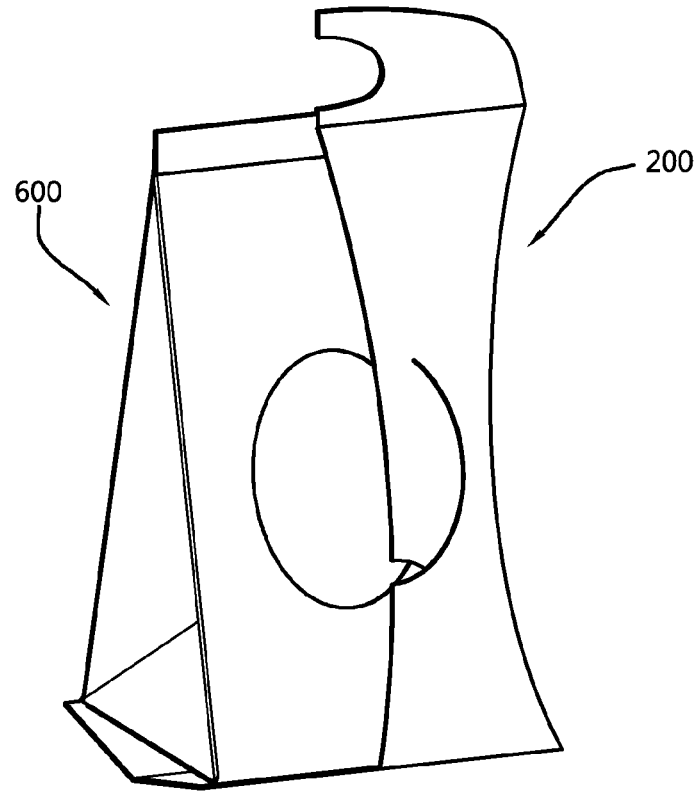

FIG. 72 shows an isometric view with a cut-out section of an assembly of a container and a liner bag.

DETAILED DESCRIPTION OF THE FIGURES

Figure 1:
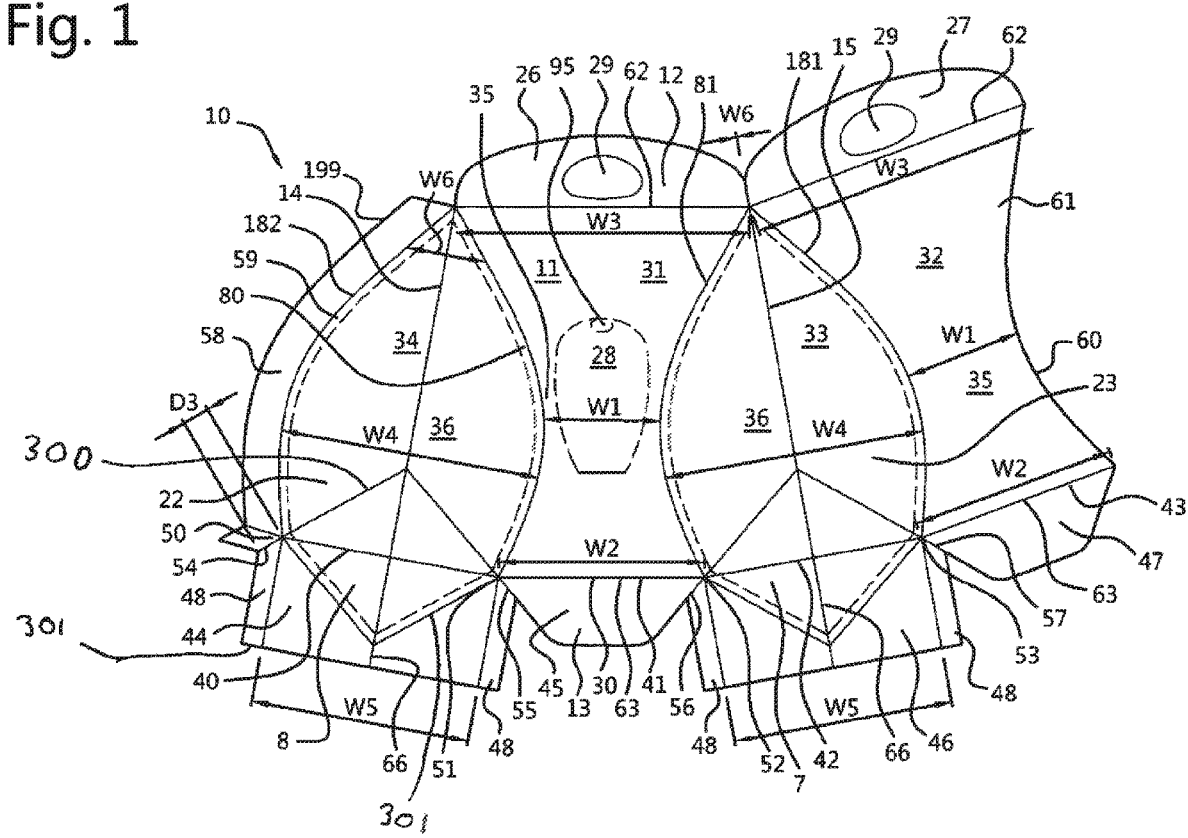
FIG. 1 shows a plan view of a blank in accordance with a preferred embodiment.

With reference to FIG. 1, a blank 10 according to the invention is shown for manufacturing a collapsed single-use container according to the invention. The blank is made from sheet material, in particular cardboard, multi-layered 'cupstock', or Bagasse sheet. The blank comprises an outer edge 199.

The blank comprises a wall section 11, an upper end section 12 and a base section 13. The base section 13 is delimited from the wall section 11 by a base perimeter fold line 30. The wall section 11 comprises a front wall zone 31, a rear wall zone 32, a right wall zone 33 and a left wall zone 34. The front wall zone 31, the right wall zone 33, the left wall zone 34 and the rear wall zone 32 are integrally connected to one another via three fold lines 80, 81,181. The fold line 80 is also referred to as the left front folding line 80. The fold line 81 is also referred to as the right front folding line 81. The side edge 59 forms a fourth fold line 182.

The front wall zone comprises a pee opening area 28. A small finger hole opening 95 may be provided which allows air into the container as the sides are squeezed and the container pops from the collapsed state into it's expanded, in-use shape. The finger hole opening 95 also makes it easy to tear open the pee opening area 28.

The front wall zone 31 and the rear wall zone 32 have a waist section 35 having a width W1 which is smaller than a width W2 at a bottom of the front wall zone and the rear wall zone and smaller than a width W3 at a top of the front wall zone and the rear wall zone. The right wall zone 33 and the left wall zone 34 have a belly section 36 having a width W4 which is greater than a width W5 at a bottom of the right wall zone and left wall zone and greater than a width W6 at the top of the right wall zone and the left wall zone. The width W6 at the top of the right wall zone and the left wall zone may be zero.

The base perimeter fold line 30 extends across the blank from a left side of the blank to a right side of the blank. The base perimeter fold line 30 comprises a left base fold line 40, a front base fold line 41, a right base fold line 42, and a rear base fold line 43. These may extend may extend at an angle of 5-15 degrees to one another, resulting in a curved base perimeter fold line 30. Side wall fold lines 14, 15 extend from the base section 13 to the upper end section 12 over the right wall zone 33 and left wall zone 34 and divide these in two portions Diamond shaped folding sections 7, 8 are provided at a lower portion of the right wall zone 33 and left wall zone 34. The diamond shaped sections are defined by fold lines 300, 301. Fold lines 300 extend from the corner locations 50, 51, 52, 53 over the wall section 11 to the side wall fold lines 14, 15. Fold lines 301 extend from the corner locations 50, 51, 52, 53 over the base section 13 to the central base fold line 66. The fold lines 300, 301 define the diamond shaped sections 7, 8 together.

The blank 10 has a base section edge 302 which forms part of the perimeter of the blank.

The diamond shaped folding sections 7, 8 straddle the base perimeter fold line 30, more in particular the right base fold line 42 and the left front base fold line 41.

The base section 13 comprises a left base portion 44 connected to the left wall zone 34 via the left base fold line 40, a front base portion 45 connected to the front wall zone 31 via the front base fold line 41, a right base portion 46 connected to the right wall zone 33 via the right base fold line 42, and a rear base portion 47 connected to the rear wall zone 32 via the rear base fold line 43.

A central base fold line 66 extends over each of the front base portion and rear base portion.

The blank 10 has four corner locations 50, 51, 52, 53 configured to form the four corners of the single-use container. A diagonal base fold line 54, 55, 56, 57 extends from each corner location. The diagonal base fold lines 54, 55, 56, 57 interconnect the left base portion 44, the front base portion 45, the right base portion 46 and the rear base portion 47.

The corners 50, 51, 52, 53 are located inward at a distance D3 from the outer edge 199 of the blank. The distance D3 is defined by the length of the diagonal base fold lines 54, 55, 56, 57. This results in liquid tightness, because when the base is folded, openings at the corners are avoided.

The left base portion 44 and the right base portion 46 comprise overlap portions 48 which are configured to be glued against an inner side of the front and rear base portion 45, 47, and the front and rear base portion 45, 47, including the overlap portions 48 and the diagonal base fold lines 54, 55, 56, 57 are configured to be folded over and glued against an outer side of the left and right base portion. This configuration allows a liquid tight end single-use container because the corners are closed.

The overlap portions 48 are elongate and extend at substantially right angles to the base perimeter fold line 30.

The blank comprises an adhesive flap 58 extending along a curved left edge 59 or right edge 60 of the wall section 11. The side connection flap is configured to be connected to an opposite side wall region 61 for forming a circumferential side wall of the single-use container.

The front wall zone 31 and the rear wall zone 32 have straight upper ends 62 and straight lower ends 63. The left wall zone and the right wall zone have straight lower ends and a pointy upper end.

The blank 10 comprises upper flaps 26, 27 which have an opening 29.

Figure 2:
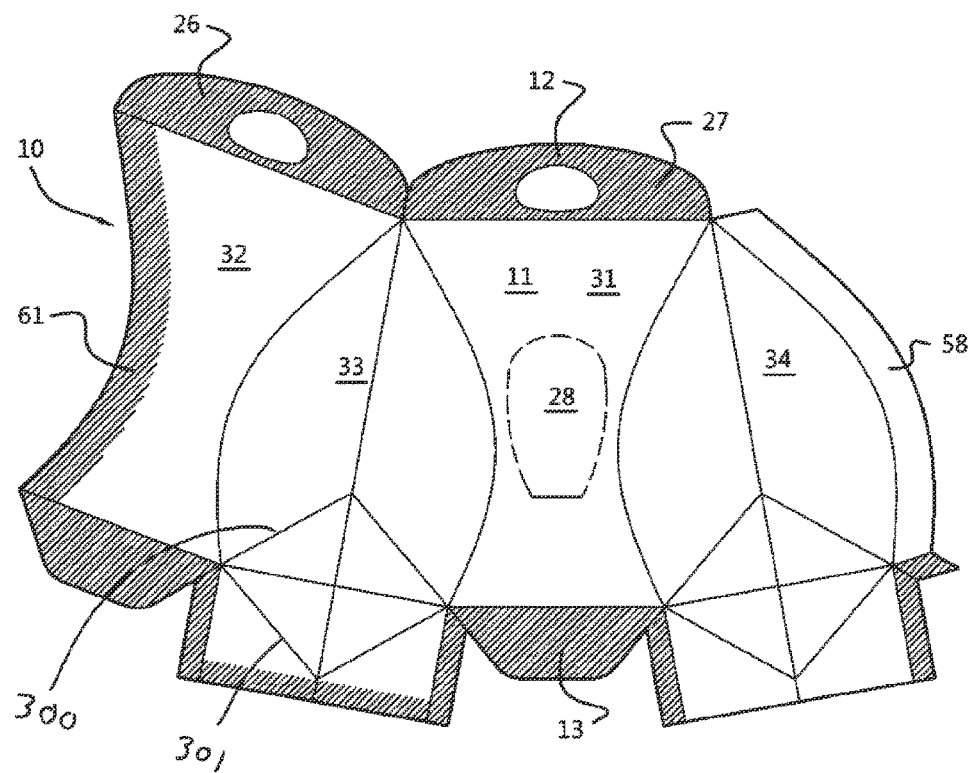
FIG. 2 shows a plan view of this blank with adhesive applied
Figure 3:
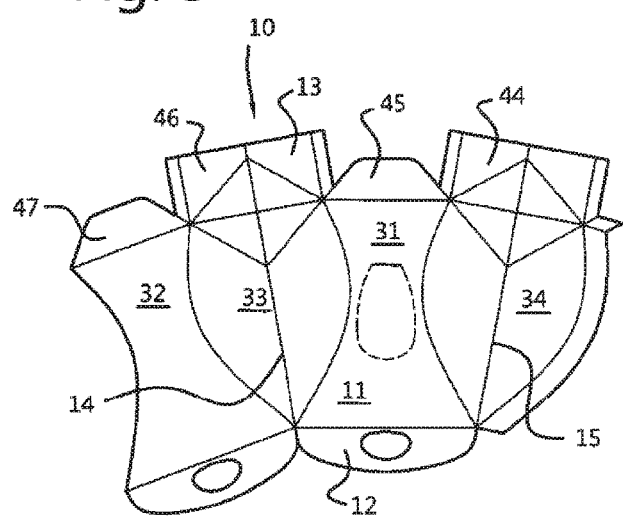
FIG. 3 shows a plan view of a blank prior to assembly into a collapsed container.
Figure 4:
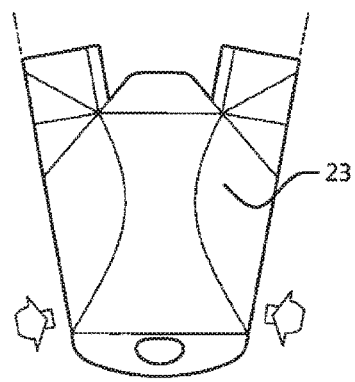
FIGS. 4 to 7 show steps of assembly of a blank into a collapsed container in accordance with a first embodiment.

Turning to FIGS. 2, 3 and 4, the method of forming a collapsed single-use container from the blank 10 comprises applying adhesive to form adhesive connections and folding the blank along the fold lines. FIG. 2 shows the inside of the blank.

Adhesive is also applied on upper flaps 26, 27 and along portions of the base section as indicated by hatching in FIG. 2.

With reference to FIG. 4, a circumferential wall is formed by interconnecting the front wall zone 31, the rear wall zone 32, the right wall zone 32 and the left wall zone 34 by an adhesive connection between the adhesive flap 58 and an opposite side wall region 61. The circumferential wall forms a tapered sleeve.

Figure 5:
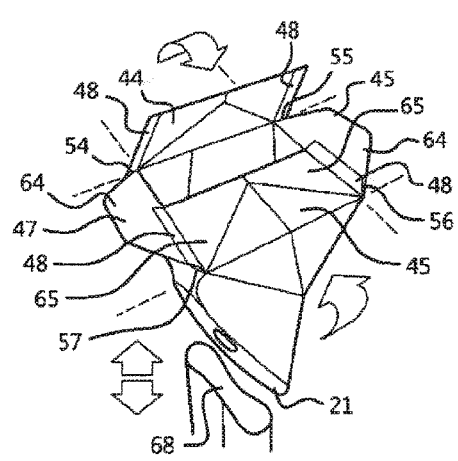
Figure 6:
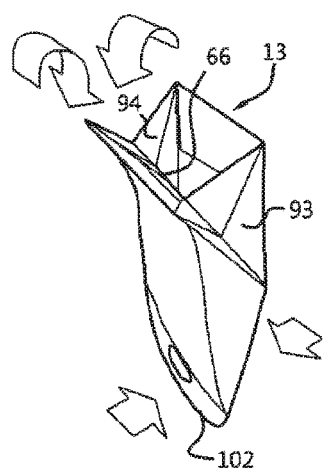
Figure 7:
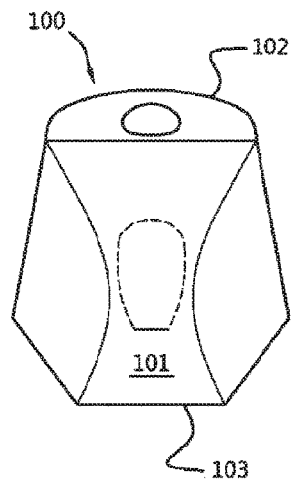
Figure 8:
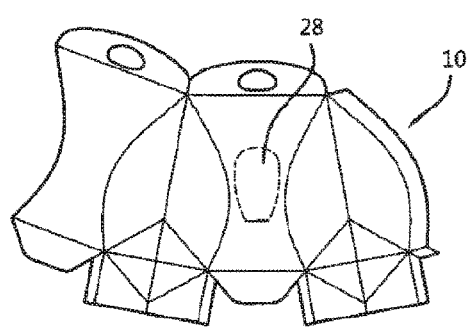
FIGS. 8 to 11 show steps of assembly of a blank into a collapsed container in accordance with a second embodiment.
Figure 9:
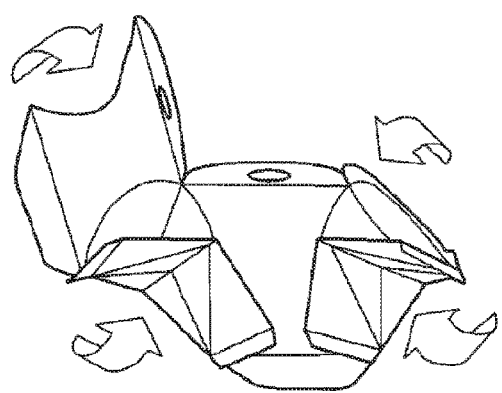

Turning to FIGS. 5, 6 and 7, the left base portion 44 and the right base portion 46 are folded inward. The overlap portions 48 of the right and left base portion are attached to the inner sides 64 of the front and rear base portions 45, 47 by adhesive connections.

A support 68 may be inserted through the upper end when it is still open to support the forming of the base section 13.

Subsequently, the front and rear base portions 45, 47 including the overlap portions 48 and the diagonal base fold lines 54, 55, 56, 57 are folded over the outer sides 65 of the right and left base portions 44,46 and attached thereto by adhesive connections.

Together, the left base portion 44, front base portion 45, the right base portion 46 and the rear base portion 47 form the base section.

With reference to FIG. 6, the base section 13 is then folded onto itself over a central base fold line 66. The result is a collapsed single-use container 100 as shown in FIG. 7. The collapsed single-use container 100 has an upper flap 102.

Turning to FIGS. 8-11, in an alternative way of making the collapsed single-use container 100 from the blank, the circumferential wall and the base section may be formed in one operation. The adhesive is applied in the same regions, but the left base portion 44, front base portion 45, the right base portion 46 and the rear base portion 47 are folded and attached at the same time as the circumferential wall.

Collapsed Single-Use Container

Figure 11:
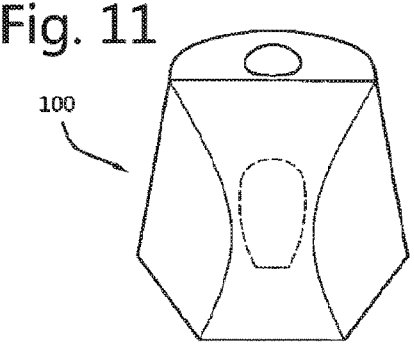
Figure 12:
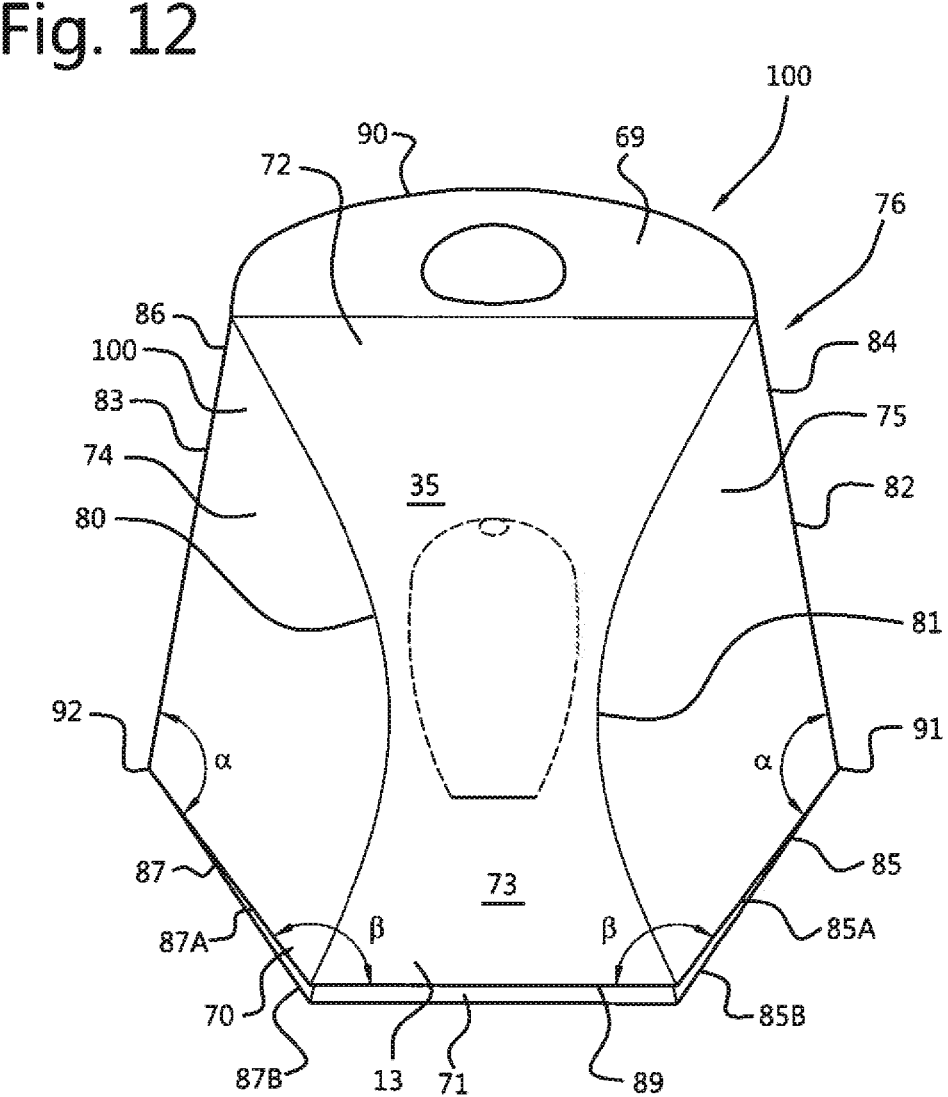
FIG. 12 shows a front view of a collapsed container in accordance with a preferred embodiment.

With reference to FIGS. 7, 11 and 12, the collapsed single-use container 100 is configured to be expanded into a single-use container. The collapsed single-use container 100 comprises a base section 13 folded onto itself along a central base fold line 66. The base section comprises a front base portion 70 and a rear base portion 71.

The collapsed single-use container 100 comprises a front part 72 comprising:
 a central front part 73 which defines the front wall of the single-use container which is to be formed,
 a left front part 74, which defines a forward part of the left wall of the single-use container which is to be formed,
 a right front part 75, which defines a forward part of the right wall of the single-use container which is to be formed, It will be clear to the skilled person that a rear part 76 of the collapsed single-use container 100 is formed in the same way as the front part 72 and comprises
 a central rear part which defines the rear wall of the single-use container which is to be formed,
 a left rear section which defines a rearward part of the left wall of the single-use container which is to be formed,
 a right rear section which defines a rearward part of the right wall of the single-use container which is to be formed.

Left and right in this paragraph are defined as left and right when the collapsed single-use container 100 is seen in front view.

The collapsed single-use container 100 comprises an upper end 69 where the front part and rear part meet. The upper end is formed by the flaps 26, 27 which in the case of a urinal are attached to one another.

The left front part 74 is delimited from the central front part 73 by a left front folding line 80. The right front part 75 is delimited from the central front part 73 by a right front folding line 81. The left and right front folding lines 80, 81 are curved and define a waste section 35 in the central front part 73, the waste section having a smaller width than a lower portion of the central front part 73 and an upper portion of the central front part.

The right front part and the right rear part are formed from the right wall zone 33 of the blank which right wall zone 33 is folded about its side wall fold line 15. The left front part and left rear part are formed from the left wall zone 34 of the blank, wherein the left wall zone is folded about its side wall fold line 14.

Except for the pee opening or pee opening area, the collapsed single-use container may be the same when viewed from the rear as when viewed from the front. For this reason the rear side is not shown separately. Therefore, the left rear part is delimited from the central rear part by a left rear folding line, and the right rear part is delimited from the central rear part by a right rear folding line. The left and right rear folding lines are curved and define a waste section in the central rear part, the waste section having a smaller width than a lower portion of the central rear part and an upper portion of the central rear part.

The collapsed single-use container 100 comprises a right edge 82 and a left edge 83. In front view the right edge 82 comprises an upper right edge 84 and a lower right edge 85, and the left edge 83 comprises an upper left edge 86 and a lower left edge 87. The collapsed single-use container 100 also has a lower base edge 89 and a curved upper edge 90.

Due to the fact that the base section 13 is folded onto itself:
 the lower right edge 85 comprises a front lower right edge part 85A and a rear lower right edge part 85B, and
 the lower left edge 87 comprises a front lower left edge part 87A and a rear lower left edge part 87B.

The upper right edge 84, the front lower right edge part 85A and the rear lower right edge part 85B form folding lines which can be pushed inwards, thereby forming the concave right wall during the expanding of the collapsible container. The upper left edge 86, the front lower left edge part 87A and the rear lower left edge part 87B form folding lines which can be pushed inwards, thereby forming the concave left wall during the expanding of the collapsible container.

The upper right edge 84 and the lower right edge 85 extend at an angle $\alpha$ of 120-160 degrees relative to one another and define a right side corner 91. The upper left edge 86 and the lower left edge 87 extend at an angle α of 120-160 degrees relative to one another and define a left side corner 92.

In front view the lower right edge 85 and the lower left edge 87 extend at an angle β of 120-160 degrees relative to the lower base edge 89 of the collapsed single-use container 100.

Figure 13A:
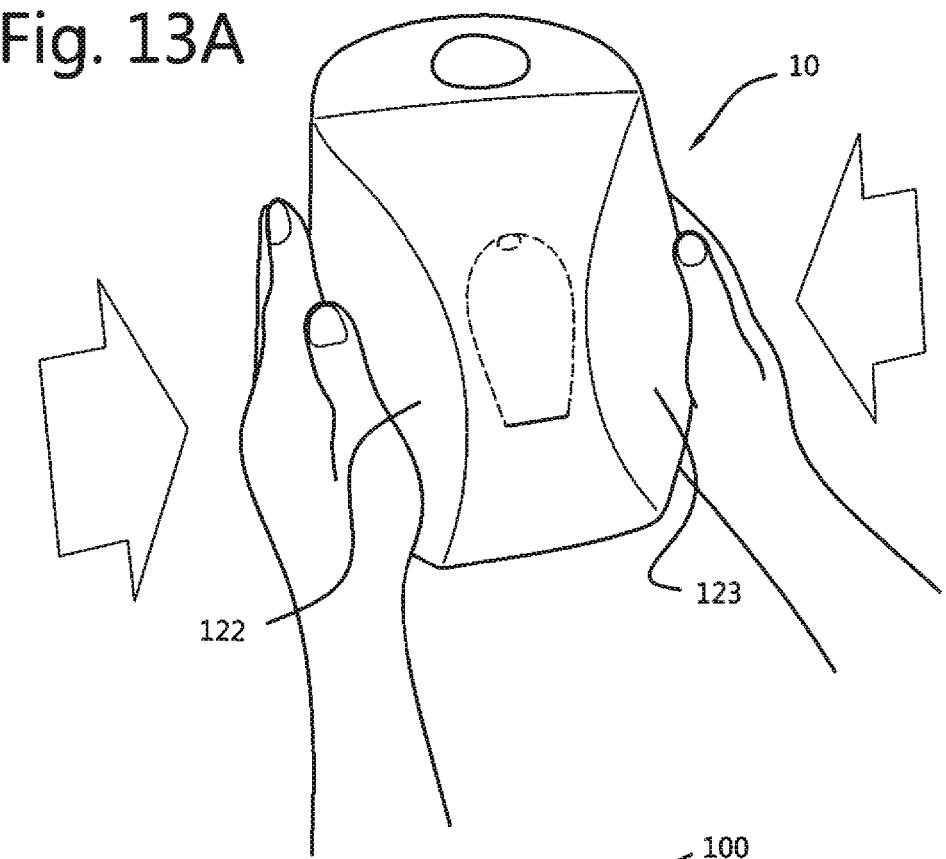
FIGS. 13A and 13B show perspective views of steps of easily expanding a collapsed container into a container of a preferred embodiment.
Figure 13B:
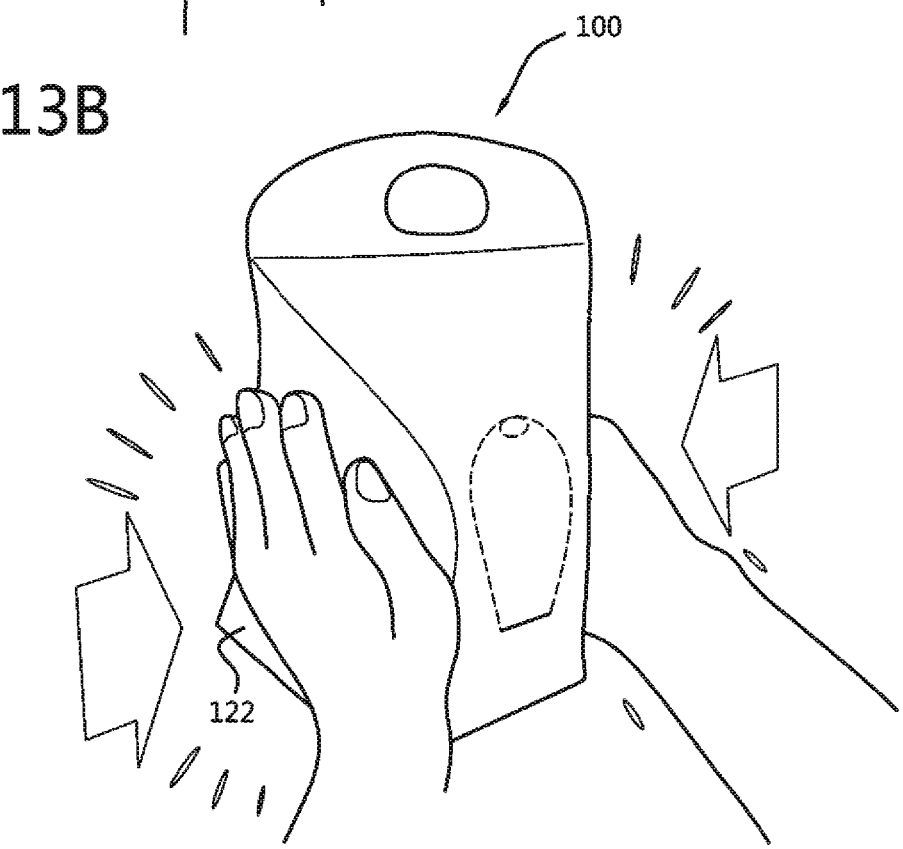

With reference to FIGS. 13A and 13B, the right front part 75 and right rear part together are deformable into the right wall of the single-use container by pushing the right edge 82 of the collapsed single-use container inward, thereby expanding the collapsed single-use container into an expanded state. The left front part 74 and the left rear part together are deformable into the left wall of the single-use container by pushing the left edge 83 of the collapsed single-use container inward.

Figure 10:
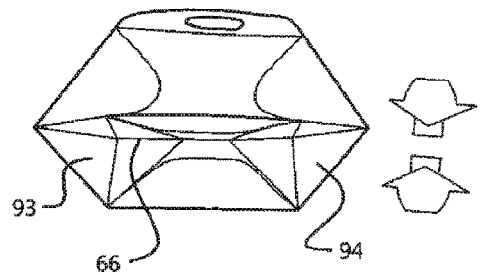

It is noted that on each side of the base section 13 which is folded onto itself, triangular areas 93, 94 are present which are also folded onto themselves. The triangular areas 93, 94 form part of the diamond sections 7,8 of the blank. When the collapsed single-use container is expanded, these triangular areas also become part of the right wall respectively left wall. The triangular areas are indicated in FIGS. 6 and 10. Each triangular area 93, 94 is itself composed of two triangular areas.

Expanded Single-Use Container

Figure 14:
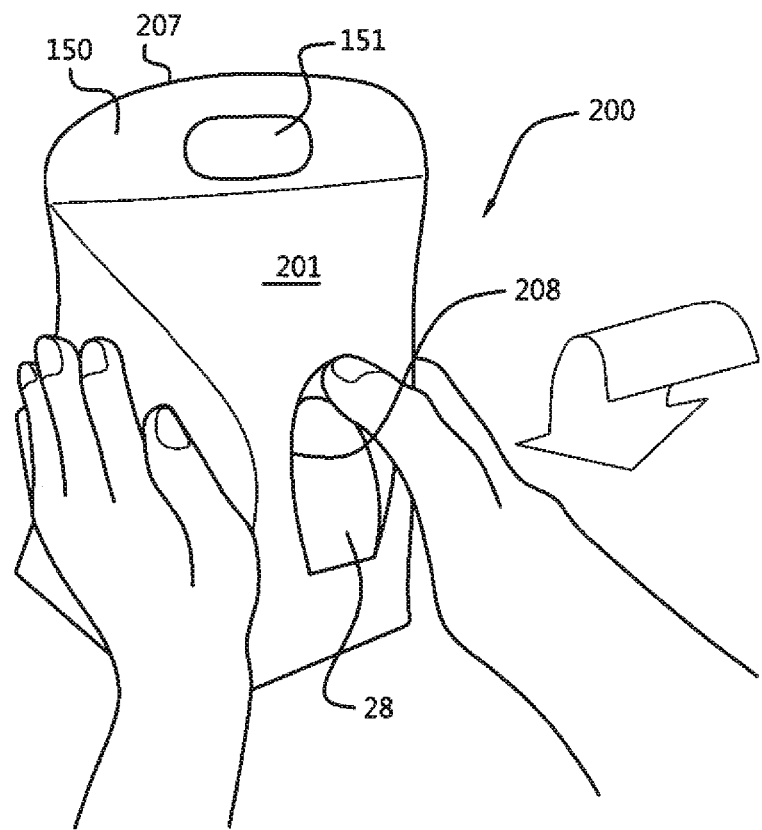
FIGS. 14 and 15 show perspective views of steps of detaching or folding down a detachable tongue from a side wall of a container of a preferred embodiment.
Figure 15:
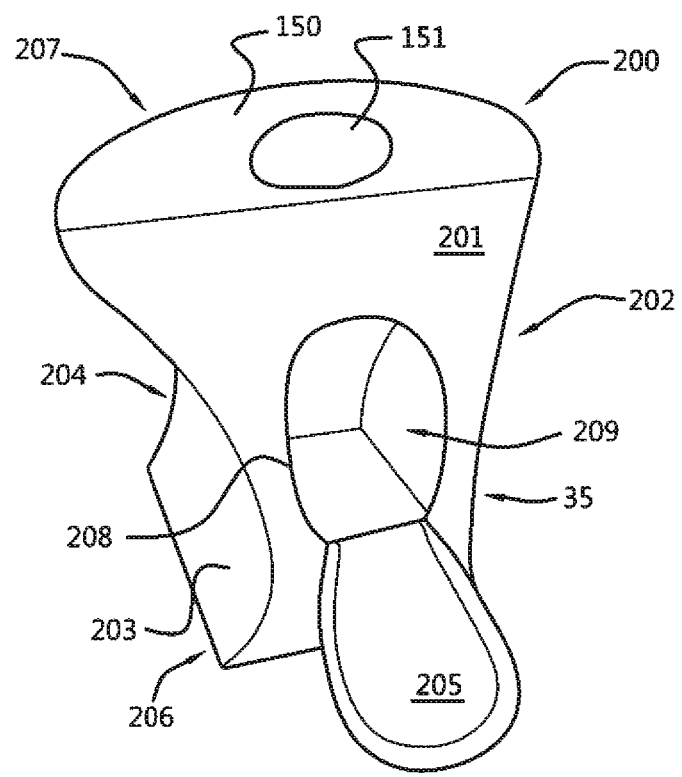
Figure 16:
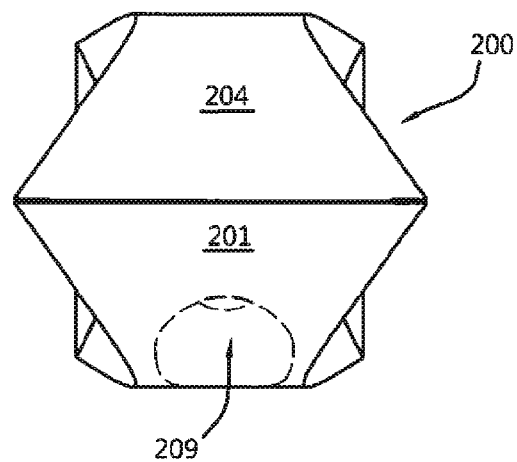
FIG. 16 shows a view from above of a container of a preferred embodiment.

Turning to FIGS. 14, 15, the single-use container 200 is shown. In the explanation of the various parts of the single-use container 200, fresh reference numerals are used for parts which are only present in the expanded use state. For parts which are also present in the collapsed state or present even in the blank, the same reference numerals are used as for the collapsed container or for the blank.

The single-use container 200 is manufactured from sheet material in particular cardboard. Due to the way the single-use container 200 is folded, there is no need for any oil-based wax water-proofing treatment.

The single-use container 200 comprises a front wall 201, a right wall 202, a left wall 203 and a rear wall 204. The single-use container 200 comprises a base 206. The base is flat and forms a surface on which the single-use container can stand. The base 206 has a square or rectangular shape.

The walls 201, 202, 203, 204 which extend upward from the base 206. The front wall 201 and the rear wall 204 are convex. The right wall 202 and left wall 203 are concave. The single-use container 200 comprises an upper end 207 which connects the front wall, right wall, left wall and rear wall.

The single-use container 200 comprises a pee opening area 28 having a perimeter 208 which is at least partially weakened. The perimeter can be broken, resulting in a flap 205 which can be folded outward and a pee opening 209 via which urine may enter the single-use container. The flap may be covered with moisture absorbing material. The fold line where the flap is attached to the front wall is relatively soft, further improving the comfort of the user and preventing paper cuts in delicate body parts.

In another embodiment, the flap may be folded inward. In yet another embodiment, the flap may be torn of completely. In again another embodiment, the flap may not be present and the pee opening already exists in the blank 10.

The pee opening 209 or pee opening area 28 is provided at the level of the waist section.

The single-use container may also comprise a second pee opening or pee opening area in the rear wall. The second pee opening or second pee opening area may have a different size or shape than the first pee opening or pee opening area.

The single-use container comprises a vertical flap 150 at the upper end, wherein the vertical flap comprises in particular a through hole 151.

The single-use container may have a volume below a lower rim of the pee opening 209 of between 0.5 and 1.5 litre.

Figure 17:
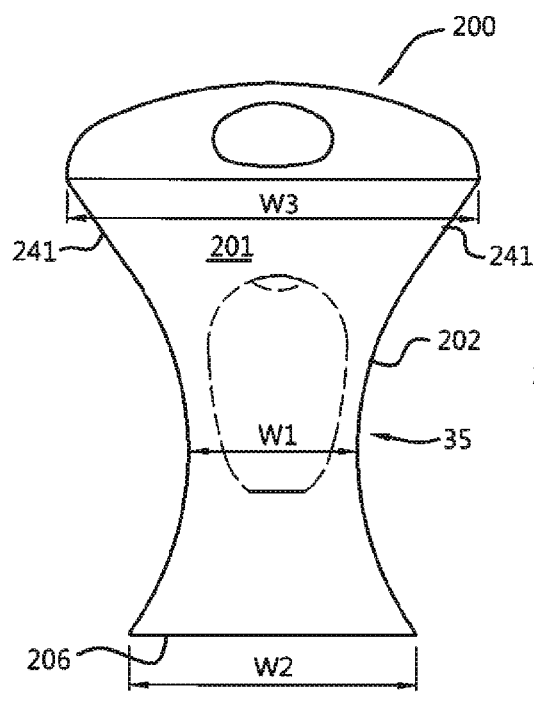
FIG. 17 shows a view from the front of a container of a preferred embodiment.

Turning to FIG. 17, in front view the single-use container has a waist section 35, the waist section having a front width W1 which is smaller than a front width W2 at the base and smaller than a front width W3 at the upper end (widths are indicated in FIG. 1). In particular the front width gradually decreases from the base 206 to the waist section and gradually increases from the waist section to the upper end 207. It is further noted that the very upper part 241 of the right wall 202 and the left wall 203 may be convex or straight instead of concave, but the overall shape of the right wall 202 and the left wall 203 is convex.

Figure 18:
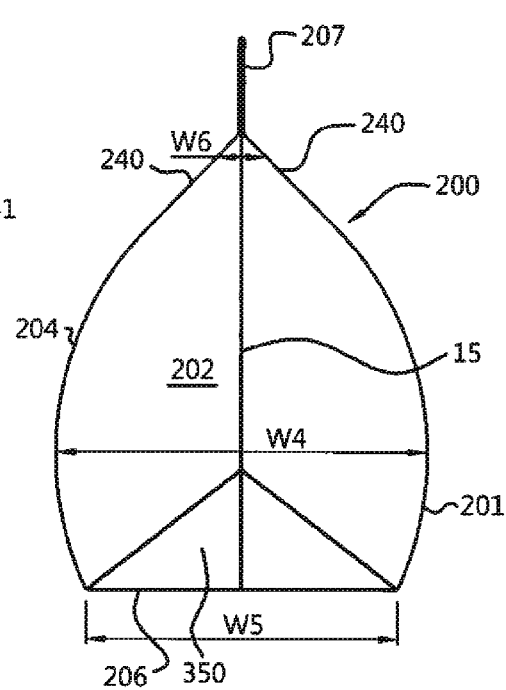
FIG. 18 shows a cross-section view from the side of a container of a preferred embodiment.

Turning to FIG. 18, in side view the single-use container has a side width W4 which reaches a maximum at the level of the waist section, the side width at the waist section being greater than the side width W5 at the base and greater than the side width W6 at the upper end. The side width in particular gradually increases from the base to the waist section and gradually decreases from the waist section to the upper end.

The front wall 201 and the rear wall 204 meet at the upper end 207. In front view, the upper end is wider than the base but obviously this may be varied. The right wall 202 and the left wall 203 do not meet at the upper end. It is noted that the very upper part 240 of the front wall 201 and the rear wall 204 may be concave or straight instead of convex, but the overall shape of the front wall 201 and the rear wall 204 is convex.

A triangular fold section 350 is visible at the bottom of the right side wall 202 in FIG. 18. The triangular fold sections 350 is composed of two smaller triangles on either side of the side wall fold line 15 in the right side wall 202. The triangular fold section 350 results from the diamond shaped folding section 7.

Figure 19C:
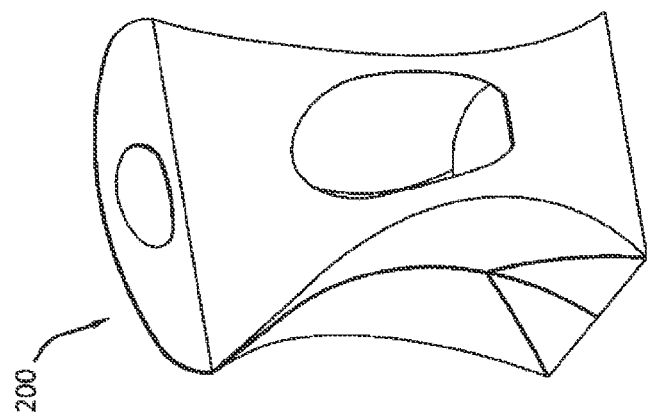
FIGS. 19A to 19C show perspective views of a container of a preferred embodiment configured for use by a female patient.
Figure 19B:
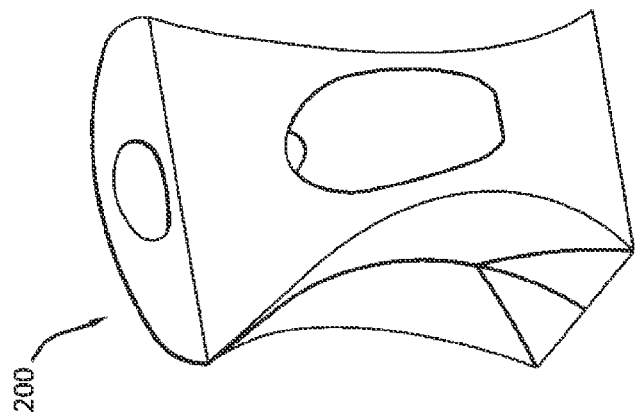
Figure 19A:
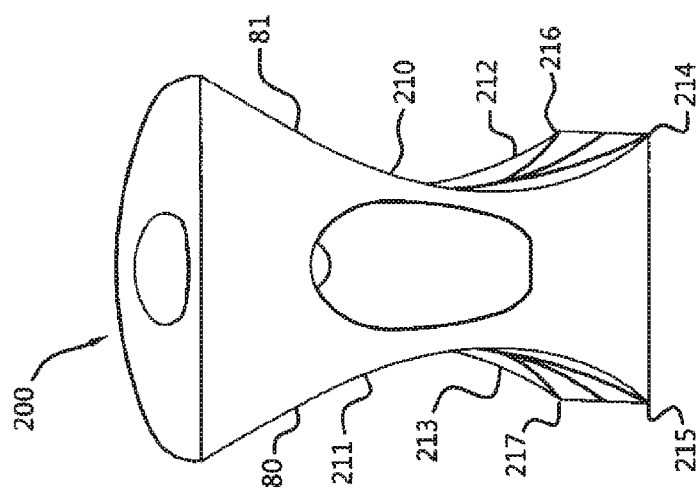
Figure 21:
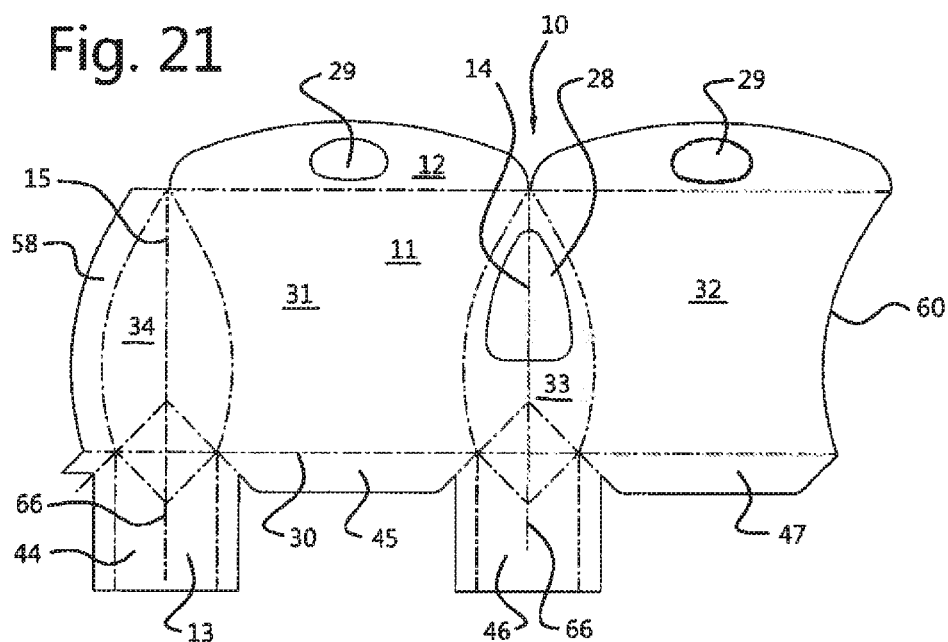
Figure 22:
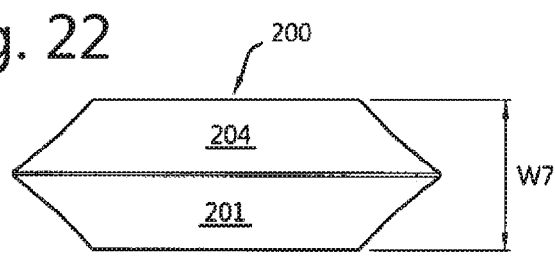
Figure 23:
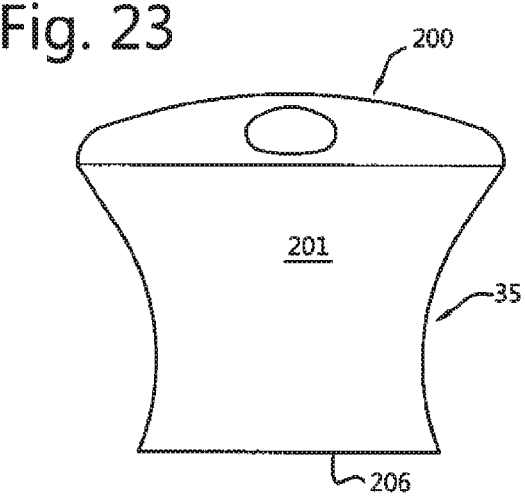
Figure 24:
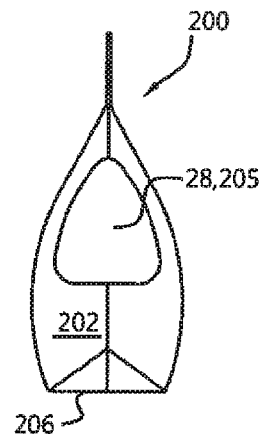
Figure 25:
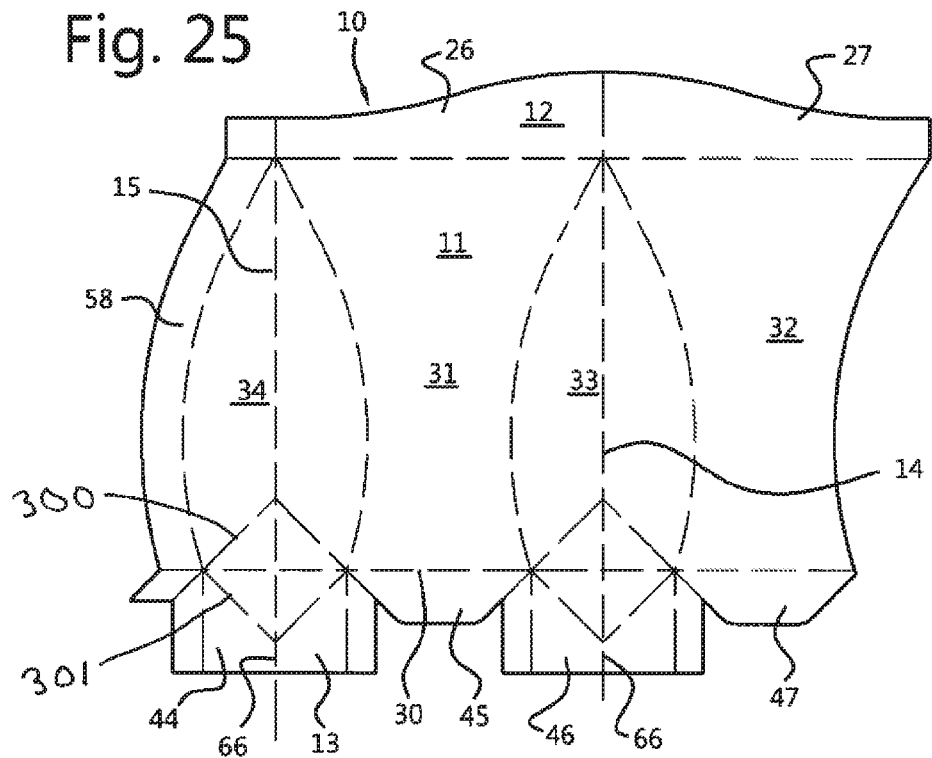
Figure 26:
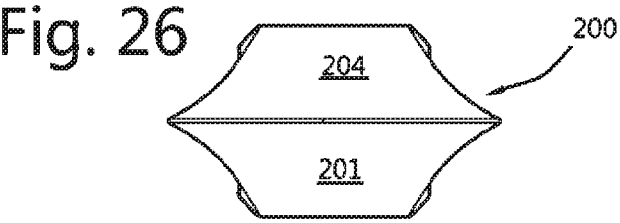
Figure 27:
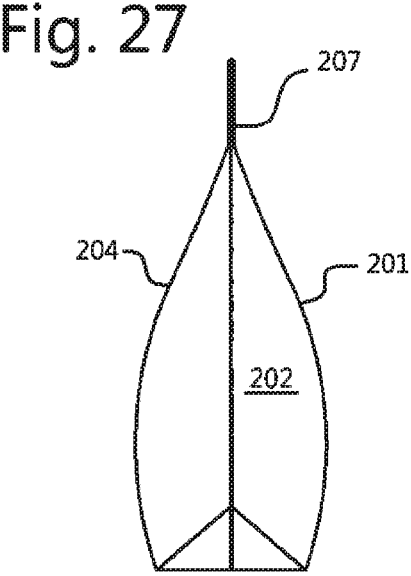
Figure 28:
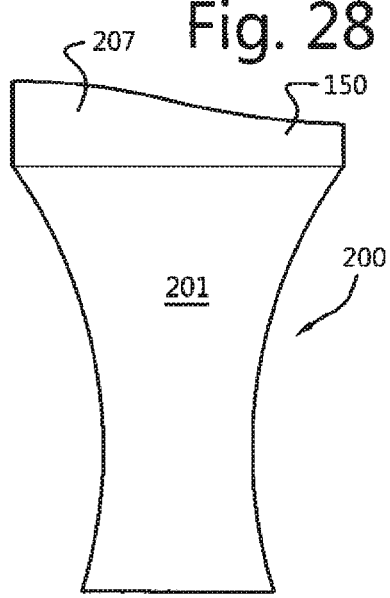

Turning to FIGS. 19A, 19B, 19C, the single-use container 200 comprises a curved front right edge 210 which extends upward from a front right corner 214 of the base, a curved front left edge 211 which extends upward from a front left corner 215 of the base, a curved right rear edge 212 which extends upward from a rear right corner 216 of the base and a curved left rear edge 213 which extends upward from a rear left corner 217 of the base, wherein the curved right front edge 210 and the curved right rear edge 212 meet at the upper end and wherein the curved left front edge 211 and the curved left rear edge 213 meet at the upper end.

The curved edges 210, 211, 212, 213 are formed from the fold lines 80, 81, 181, 182 from the blank and from the collapsed container. The side wall fold lines 14,15 remain visible in the single use container and extend over the right and left wall.

The front wall 201, the right wall 202, the left wall 203 and the rear wall 204 are integrally connected to one another via three fold lines 80, 81,181 which form three upstanding edges 210, 211, 212 which extend upwardly from three corners 214, 215, 216 of the base. The adhesive connection is formed at the fourth fold line 182.

The curved front right edge 210 and the curved right rear edge 212 define a right plane. The right wall 202 lies either on the right plane, or outside of the right plane. Likewise, the curved front left edge 211 and the curved left rear edge 213 define a left plane. The left wall 203 lies either on this left plane or outside of this left plane. The shape of the right wall and left wall of the container according to the present invention is quite different from the shape of the right and left wall of the container of D1, wherein a significant part of the right wall and left wall live within (on the inner side) of the right plane respectively the left plane which are defined by the corresponding edges of the front wall and rear wall. The technical effect of these different shape is a better economical shape. When the container is positioned between the legs of a user, the legs engaged the right wall and the left wall, and not so much the rather sharp edges of the front wall and rear wall. This results in more comfort to the user.

Furthermore, the right wall 202 and the left wall 203 as shown in FIG. 19a and in the various other figures, are substantially curved in a single plane of curvature. This is also quite different from the right wall and left wall of the container of D1. The right wall 202 and the left wall 203 are substantially curved in a single plane of curvature, but it is noted that the upper portion may have a tendency to bulge slightly outwards. However this is quite different from the right wall and left wall of the container of D1, which bulge inwards at the upper portion.

Furthermore, the right wall and left wall of the container of D1 are convex over a significant portion of their surface, in particular at the bottom half, see FIG. 1 of D1. This is also quite different from the right wall and the left wall of the present invention, which do not have a convex part.

Two walls 201,204 are connected to one another via an adhesive connection at a fourth upstanding edge 213 which extends upwardly from a fourth corner 217 of the base. The skilled person will understand that the adhesive connection may be formed at any of the four upstanding edges.

Turning to FIGS. 20A, 20B, 20C a male version is shown, which has a pee opening area 28 which is located slightly higher up, resulting in large volume below the lower rim of the pee opening.

Turning to FIGS. 21, 22, 23 and 24 another embodiment of the invention is shown. The embodiment is narrower in the sense that the base 206 is rectangular having a length L1 which is significantly greater than a width W7, The pee opening area 28 or pee opening is located in a right or left wall 202, 203. The base perimeter fold line 30 is straight. This embodiment is specifically useful for female users who are in bed in a supine position. The relatively narrow shape of the single-use container allows easy positioning between the legs.

Turning to FIGS. 25, 26, 27, 28 a single-use container 200 is shown which is configured as a sick bag. The flaps 26, 27 are not connected to one another, but stay loose.

The vertical flap 150 has a wave shape, resulting in a higher portion (left) and a lower portion (right). The higher portion is intended to be positioned at the nose and the lower portion is intended to be positioned at the mouth or chin.

Turning to FIGS. 29, 30 and 31 the upper end can be opened by the user by pushing the left and right corners 221, 222 inward. This creates an upper opening 220 and also changes the shape of the single-use container as is shown in FIG. 30. The user can then vomit into the sick bag. The single-use container 200 does not have a pee opening or pee opening area. This embodiment may also be used as a urinal, for instance in a car. In this case the higher portion of the flap 150 is intended to form is the forward portion and the lower portion is intended to be placed under the bumb.

Use

The method of forming the single-use container from the collapsed container comprises pushing a left edge and a right edge of the collapsed single-use container inward, and forming the concave right and left wall and the convex front and rear wall.

Turning to FIGS. 32A-E, a male or female user 228 can lie on a bed with the back somewhat upright. The legs 230 are separated and the knees slightly lifted. The single-use container 200 can be positioned between the legs 230. The upper end 207 projects upward from between the legs and the user can hold the upper end 207 with his or her hand. The legs may squeeze together, thereby clamping the single-use container as shown in FIG. 32D. The user may then pee. When finished, the legs are spread again and the single-use container 200 may be removed and disposed of.

Turning to FIGS. 33, 34 and 35, it is shown that the pee opening 209 is automatically positioned directly in front of the pee hole 225 of the female user. The tongue fold is approximately 50 mm above the mattress and at the lower end of the vagina. The pee hole 225 is about 90-100 mm above the mattress. The flap 205 is folded inward or outward. When folded outward, the flap, optionally including an adhesive sanitary towel, will be between the buttock cheeks of the user.

The inner face of the rear wall 204 deflects the urine downward.

The user will generally create a slight inclination of the mattress at the location where the single-use container is to be positioned. This will automatically result in a slight inclination of the single-use container of about 10 degrees, so that the pee opening 209 is positioned and oriented in the correct way. The bladder 234 and the anus 235 are also indicated for further clarity.

Turning to FIG. 36, the single-use container is shown in use by a male. The penis 233 is inserted into the pee opening 209.

Turning to FIG. 37, a further variant is shown. The base section 13 is located centrally in the blank. The base section is delimited from the wall section by a base perimeter fold line 30 which has a square shape or rectangular shape.

The wall section 11 comprises multiple wall zones 31, 32, 33, 34 which are separate from one another. Each of the front wall zone 31, the rear wall zone 32, the right wall zone and the left wall zone 34 is integrally connected to a side of said centrally located base section via a respective base fold line 40, 41, 42, 43 and extends away from the centrally located base section.

At least two of the wall zones 31, 32, 33, 34, in particular the left and right side wall zones 33, 34, comprise adhesive flaps 58 on either side for forming an adhesive connection between the four wall zones.

The base perimeter fold line 30 is square or rectangular and comprises four corner locations 50, 51, 52, 53. The corner locations are at a distance from the outer edge 199 of the blank. An interconnecting fold line 320 extends away from each corner location and corner sheet sections 322 are provided which connect the adhesive flaps 58 with the adjoining wall zone. The corner sheet sections are connected to said adhesive flap via the interconnecting fold line 320 which extends away from a corner. The corner sheet extensions are connected to an adjoining wall via an opposite fold line 323. The corner sheet sections 322 are intended to be folded about the interconnecting fold line 320 and about the opposite fold line 323 and are intended to be connected with an adhesive connection to the adjoining wall on one side and to be connected to the adhesive flap via an adhesive connection on the other side.

Each corner sheet section 322 connects the adhesive flap 58 to which it is attached to another wall zone. The corner sheet sections 322 may be triangular. The interconnecting fold lines 320 and corner sheet sections 322 ensure that at the corners, a liquid tight adhesive connection is formed during the making of the collapsed single use container.

Turning to FIGS. 38, 39, 40 a method of forming the collapsed single use container from the blank of FIG. 37 is shown. The front wall zone 31, the rear wall zone 32, the right wall zone 33 and the left wall zone 34 are folded over the base fold lines 40, 41, 42, 43 via which they are connected to the base. Adhesive connections are formed between the front wall zone 31, the rear wall zone 32, the right wall zone 33 and the left wall zone 34, in particular via the adhesive flaps 58.

Second Invention—Blank

Turning to FIGS. 41, 42A and 42B blanks 310 of a second invention are shown, in which the single-use container has straight walls. Many features are similar to the variant of FIGS. 1-18. For conciseness, many of these features are not discussed again herein below and the focus is put on the differences.

FIG. 41A shows a blank 310 for manufacturing a collapsed single-use container 400, the blank comprising: a base section 13, a wall section 11 and an upper end section 12. The base section is delimited from the wall section by a base perimeter fold line 30. The wall section comprises a front wall zone 31, a rear wall zone 32, a right wall zone 33 and a left wall zone 34.

The side edges 59, 60 of the wall zones 31, 32, 33, 34 are straight and folding lines 80, 81,181 between the front wall zone 31, the rear wall zone 32, the right wall zone 33 and the left wall zone 34 are also straight. The side edges 59, 60 and the folding lines 80, 81,181 are commonly referred to as: sides.

In the embodiment of FIG. 41A, the front wall zone and the rear wall zone have a trapezoid shape but this may also be a square or rectangular shape. The right wall zone and the left wall zone have a triangular shape.

A centre 301 of the pee opening 209 or pee opening area 28 is provided at 40-60 percent of a height of the collapsed container.

The blank of FIG. 41A results in the collapsed single-use container of FIG. 44. The blank results in a container having straight walls.

Turning to FIG. 42A, another embodiment is shown. The blank is mirrored with respect to the blanks of FIGS. 1 and 41. This embodiment comprises roof portions 330 which are attached to the upper ends of the wall zone 31,32,33,34 via roof fold lines 331. Diagonal roof fold lines 335 extend away from corners 336 where the roof fold lines 331 meet the fold lines 80,81,181 between the wall zones.

The blank comprises four roof portions 330. The four roof portions 330 are connected to one another via intermediate roof portions 337, thereby forming a single roof zone extending along the upper end of the wall section 11. The roof fold lines 331 form one interconnected roof fold line extending from a left side of the blank to a right side of the blank.

The intermediate roof portions 337 have the positive effect that the roof of the container to be formed will become liquid tight, because at the corners 336 no gaps will occur.

In the right wall zone 33, two diamond shaped folding sections 7, 7A are provided, one for the base and one for the roof. In the left wall zone 34, two diamond shaped folding portions 8, 8A are provided, one for the base and one for the roof. The diamond shaped sections are defined by folding lines.

The blank of FIG. 42A results in the collapsed single-use container of FIG. 50.

Turning to FIG. 42B, the base section 13 is not formed from four distinct portions, but extends as a band across the blank from left to right. Each base portion 44,45,46,47 has a same length L2 measured form the base perimeter fold line 30. The overlap portions 48 are triangular.

The roof portions 330 can be divided in two groups. Short roof portions 330 are connected to the front wall zone 31 and the rear wall zone 33 and longer roof portions 330 are connected to the right wall zone 33 and the left wall zone 34.

The blank of FIG. 42B results in the collapsed single-use container of FIG. 48, with a difference that FIG. 48 shows a vertical flap 150 at the upper end and this vertical flap would not be present when the blank of FIG. 42B is formed into a collapsed container.

Turning to FIGS. 53, 54, 55, in another embodiment, the blank 310 has a central base section 13. This version of the blank of the second invention is similar to the embodiment of FIG. 37 for the first invention. The base section 13 is delimited from the wall section by a base perimeter fold line 30 which has a square shape or rectangular shape and comprises four base fold lines 40, 41, 42, 43. The wall section comprises four separate parts, i.e. the front wall zone 31, the rear wall zone 32, the right wall zone 33 and the left wall zone 34 which are separate from one another. Each of the front wall zone 31, the rear wall zone 32, the right wall zone 33 and the left wall zone 34 is integrally connected to said centrally located base section via a respective base fold line 40, 41, 42, 43 and extends away from the centrally located base section 13.

Each of the wall zones 31,32, 33, 34 comprises side edges 325. The side edges 325 are straight. The side edges 325 are also referred to as sides.

At the outer ends of the wall zones 31,32,33,34 roof portions 330 are provided which are connected to the wall zones 31,32,33,34 via roof fold lines 331.

In the right wall zone 33, two diamond shaped folding sections 7, 7A are provided, one for the base and one for the roof. In the left wall zone 34, two diamond shaped folding portions 8, 8A are provided, one for the base and one for the roof. The diamond shaped sections are defined by folding lines.

A cut-out 333 is provided in the roof portion 330 of front wall zone and the rear wall zone.

At least two of the wall zones 31, 32, 33, 34, in particular the left and right side wall zones 33, 34, comprise adhesive flaps 58 for forming an adhesive connection between the four wall zones.

The pee opening 28 is provided in the right side wall 33.

The base perimeter fold line 30 comprises four corners 50, 51, 52, 53. Similar to the embodiment of FIG. 37, an interconnecting fold line 320 extends away from each corner and corner sheet sections 322 connect the adhesive flaps 58 with the adjoining wall zone, see FIG. 53. The corner sheet section 322 which is indicated connects the adhesive flap 58 of the right wall zone 33 with the front wall zone. The corner sheet sections 322 may be triangular. The interconnecting fold lines 320 and corner sheet sections 322 ensure that at the corners, a liquid tight adhesive connection is formed during the making of the collapsed single use container.

The embodiment of FIG. 53 has square or rectangular front and rear wall zones 31,33 and trapezoid right and left wall zones 33,34. The trapezoid right and left wall zones have a wide base and narrow top. The embodiment of FIG. 54 has square or rectangular front and rear wall zones 31,33 and trapezoid right and left wall zones 33,34. The trapezoid right and left wall zones have a narrow base and wide top. The embodiment of FIG. 55 has square or rectangular front and rear wall zones 31,33 and triangular right and left wall zones 33, 34.

Second Invention—Collapsed Container

Turning to FIGS. 43, 44, 45, a collapsed single-use container 400 configured to be expanded into a single-use container is shown. The collapsed single-use container 400 is manufactured from sheet material comprises a base section 13 folded onto itself along a central base fold line 66. The collapsed single-use container 400 comprises a front part 72 comprising a central front part 73 which defines the front wall 201 of the single-use container which is to be formed, a left front part 74 which defines a forward part of the left wall 203 of the single-use container which is to be formed, a right front part 75 which defines a forward part of the right wall 202 of the single-use container which is to be formed.

The collapsed container further comprises a rear part comprising a central rear part which defines the rear wall 204 of the single-use container which is to be formed, a left rear section which defines a rearward part of the left wall 203 of the single-use container which is to be formed, a right rear section which defines a rearward part of the right wall 202 of the single-use container which is to be formed, an upper end where the front part and rear part meet.

The left front part 74 is delimited from the central front part 73 by a left front folding line 80, and the right front part 75 is delimited from the central front part 73 by a right front folding line 81. The left and right front folding lines 80,81 are straight. The same applies to the rear side of the collapsed container.

In the same way as with the previous embodiment, the collapsed single-use container 400 can be expanded into an expanded state by pushing a right edge 82 and a left edge 83 of the collapsed single-use container inward, thereby forming the right and left wall and unfolding the base section into a base.

The collapsed single-use container 400 comprises an upper right edge 84 and a lower right edge 85, and an upper left edge 86 and a lower left edge 87. As indicated in FIG. 43. the upper right edge 84, the front lower right edge part and the rear lower right edge part form folding lines which can be pushed inwards, thereby forming the straight right wall during the expanding of the collapsible container, and the upper left edge, the front lower left edge part and the rear lower left edge part form folding lines which can be pushed inwards, thereby forming the straight left wall during the expanding of the collapsible container.

The upper right edge 84 and the lower right edge 85 extend at an angle α of 90-150 degrees relative to one another and define a right side corner 91. The upper left edge 86 and the lower left edge 87 extend at an angle α of 90-150 degrees relative to one another and define a left side corner 92. In front view the lower right edge 85 and the lower left edge 87 extend at an angle β of 120-160 degrees relative to a lower base edge 89 of the collapsed single-use container.

The embodiment of FIG. 43 has a rectangular central front part 73. The embodiment of FIG. 44 has a trapezoid central front part 73, the base being narrower than the top. The embodiment of FIG. 44 has a trapezoid central front part 73, the top being narrower than the base.

Similar to the embodiment of FIGS. 1-18, the base is formed by a plurality of base portions folded over one another and connected to one another via an adhesive connection, each base portion being integrally connected via a respective base fold line to one of the walls extending upwardly from the base of the container which is to be formed.

The collapsed single-use container 400 may form a single-use urinal, wherein the central front part 73 may comprise a pee opening, or a pee opening area having a perimeter which is at least partially weakened and is configured to be broken to remove the pee opening area or to fold the pee opening area inward or outward in order to form the pee opening.

The central front part 73 and the central rear part may not be attached to one another at the upper end of the collapsed single-use container. In such an embodiment in the expanded form the upper end of the single-use container can be opened by the user by pushing the left and right corners inward, thereby creating an upper opening.

As indicated in FIGS. 46 and 47 at least one side wall may comprise a pee opening 209, or a pee opening area 28 having a perimeter 208 which is at least partially weakened and is configured to be broken to remove the pee opening area or to fold the pee opening area inward or outward in order to form the pee opening 209. Generally in this variant the pee opening will be in a side wall. A centre of the pee opening or pee opening area is provided at 40-60 percent of a height of the collapsed container.

Multiple pee openings or pee opening areas may be provided, similar to the embodiment of FIGS. 1-18.

In the variant of FIGS. 48, 49, 50, the right and left side wall parts 74,75 comprise an extra corner 360, 381. The right edge 82 now comprises three sections, from bottom to top 85, 84 and 362. The left edge 83 also comprise three sections 87, 86 and 363. This shape results in a roof part 312 being formed during expansion of the collapsed container, see FIG. 52.

Collapsed single-use container according to any of the preceding claims 122-135 except claims 127-129, wherein the front wall (201), the right wall (202), the left wall (203) and the rear wall (204) are connected to one another via adhesive connections and wherein each of the front wall (201), the right wall (202), the left wall (203) and the rear wall (204) is integrally connected to the base via a fold line.

Second Invention—Container

Turning to FIGS. 41B, 41C, 41D the single use container 500 formed from the blank of FIG. 41A is shown. The blanks 310 are first formed into a collapsed single use container and are subsequently expanded. This is similar to the embodiment of FIGS. 1-18.

Because of the shape of the blank 310 of FIG. 41A, the front wall 201, the right wall 202, the left wall 203 and the rear wall 204 are integrally connected to one another via three fold lines 80, 81,181 which form three upstanding edges 210, 211, 212 which extend upwardly from three corners 214, 215, 216 of the base, wherein in particular two walls 201,204 are connected to one another via an adhesive connection at a fourth upstanding edge 213 which extends upwardly from a fourth corner 217 of the base.

The base is formed by a plurality of base portions 44, 45, 46, 47 folded over one another and connected to one another via an adhesive connection, each base portion being integrally connected via a respective base fold line 40, 41, 42, 43 to one of the walls 201, 202, 203, 204 extending upwardly from the base.

The base comprises:
- a left base portion 44 connected to the left wall via a left base fold line 40,
- a front base portion 45 connected to the front wall via a front base fold line 41,
- a right base portion 46 connected to the right wall via a right base fold line 42,
- a rear base portion (47) connected to the rear wall via a rear base fold line 43, wherein the base has four corners 214, 215, 216, 217, wherein a diagonal base fold line 54, 55, 56, 57 extends from each corner, wherein the diagonal base fold lines interconnect the left base portion, the front base portion, the right base portion and the rear base portion, wherein the left base portion, the front base portion, the right base portion and the rear base portion are folded onto one another.

The left base portion and the right base portion comprise overlap portions 48 which are glued against an inner side 64 of the front and rear base portion, and wherein the front and rear base portion 45,47 including the overlap portions and the diagonal base fold lines are folded over and glued against an outer side 65 of the left and right base portion to form liquid tight seals.

Turning to FIGS. 42A1, 42A2, 42A3, the single use container resulting from the blanks of FIG. 42A is shown. The collapsed single use-container is shown in FIG. 48. The side walls 201,202,203,204 are straight. The right and left side walls 202,203 are trapezoid. The front and rear side walls 201,204 are rectangular but may also be square. A triangular fold section 350 is visible at the bottom of the right side wall 202 and a triangular fold section 351 is visible at the top of the right side wall. The triangular fold sections 350, 351 are composed of two smaller triangles. The triangular fold sections 350,351 result from the diamond shaped folding sections 7, 7A. The roof part 312 has a rectangular shape.

Turning to FIGS. 42B1, 42B2, 42B3, the single use container resulting from the blanks of FIG. 42B is shown. The collapsed single use-container is shown in FIG. 44. The four walls 201, 202, 203, 204 have a trapezoid shape with a wide base and narrow top.

Turning to FIGS. 53A, 54A, 55A, another embodiment of the single-use container 500 is manufactured from sheet material and has several similarities with the container 200 shown in previous figures such as FIGS. 14-19C. The containers of 53A, 54A, 55A are respectively formed from the blanks of FIGS. 53, 54, 55.

The container 500 has been formed from a collapsed single-use container 400 by pushing a left edge 83 and a right edge 82 of the collapsed single-use container inward, thereby expanding the collapsed single-use container into an expanded state.

The single-use container comprises a base 206 on which the single-use container can stand, a front wall 201, a right wall 202, a left wall 203 and a rear wall 204 which extend upward from the base. Unlike the embodiment of FIGS. 14-19C, the front wall 201, the right wall 202, the left wall 203 and the rear wall 204 are straight. The container 500 can be made from the blanks shown in respectively FIGS. 53, 54, 55.

The single-use container 500 comprises a straight front right edge 210 which extends upward from a front right corner 214 of the base, a straight front left edge 211 which extends upward from a front left corner 215 of the base, a straight right rear edge 212 which extends upward from a rear right corner 216 of the base and a straight left rear edge 213 which extends upward from a rear left corner 217 of the base.

If the single use container is made from the blanks of FIGS. 53,54,55 respectively, each of the front wall 201, the right wall 202, the left wall 203 and the rear wall 204 is integrally connected to the base via a base folding line and the front wall 201, the right wall 202, the left wall 203 and the rear wall 204 are connected to one another via adhesive connections, in particular via the adhesive flaps 58.

In FIG. 53A, in side view the container 500 has a trapezoid shape with a narrow base. The container 500 also has a roof part. In front view the container has a square or rectangular shape.

In FIG. 54A, in side view the container 500 has a trapezoid shape with a wide base and a narrow top. The container 500 also has a roof part. In front view the container has a square or rectangular shape.

In FIG. 55A, in side view the container 500 has a triangular shape with a wide base and a narrow top. In side view the front wall and rear wall meet at the upper end. The right front edge and the right rear edge meet at the upper end and wherein the left front edge and the left rear edge meet at the upper end.

In front view the container 500 may also have a trapezoid shape.

The base of the container 500 has a square or rectangular shape. The base may be flat and form a surface on which the container can stand.

The single-use container 500 may form a single-use urinal, wherein at least one side wall 202, 203 comprises a pee opening 209, or a pee opening area 28 having a perimeter 208 which is at least partially weakened and is configured to be broken to remove the pee opening area or to fold the pee opening area inward or outward in order to form the pee opening 209.

In another embodiment the single-use container 500 may form a single-use urinal, wherein the front wall 201 comprises:
- a pee opening 209, or
- a pee opening area 28 having a perimeter 208 which is at least partially weakened and is configured to be broken to remove the pee opening area or to fold the pee opening area inward or outward in order to form the pee opening 209.

A centre of the pee opening 209 or pee opening area 28 is provided at 40-60 percent of a height of the collapsed container.

Typically the pee opening or pee opening area will be provided in a side wall, because the side walls will generally be more narrow than the front and rear walls.

In the embodiment of FIG. 53A, the roof part 312 comprises a roof opening 313. The roof opening is formed by the cut-outs 333 in the blanks. The roof part 312 is formed by folding the roof portions 330 onto one another.

The roof opening allows a body liquid or other liquid to be inserted via the top. In this embodiment, there is no opening in a side wall, but an additional opening in the side wall is also possible. This embodiment may also serve as a single-use waste basket capable of holding liquids of beverages and the likes.

In another embodiment, the upper end can be opened by the user by pushing the left and right corners inward, thereby creating an upper opening, allowing the single-use container 500 to be squeezed open and used as a sick bag.

Second Invention—Further Embodiment

Turning to FIG. 56, a further embodiment of the second invention is shown. The blank 310 has roof portions 330.

The roof portions 330 have an upper opening 313 which has a rounded shape having a first wide curve 340 and a second opposite smaller curve 341 and a rounded constricted section 342 between the first and second curve. The upper opening is provided in the roof portions which are attached via roof fold lines 331 to the front wall zone and the rear wall zone.

Each roof portion 330 which comprises an opening 313 comprises two segments 344,345 connected via segment fold line 346.

Cut out portions 33 are provided in the roof portions 330 which are attached to the right and left wall zones 33,34. The cut out portions 333 take away a part of the diamond sections 7A, 8A.

In this embodiment all four wall zones 31, 32, 33, 34 have a trapezoid shape.

Figure 58:
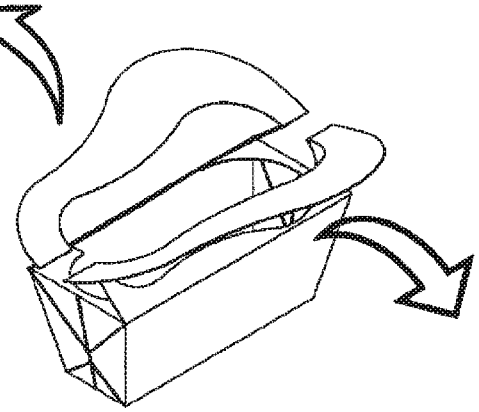

Turning to FIGS. 57, 58, 59 and 60, the blank 310 of figure can be folded into a collapsed container 400. The wall zones 31,32,33,34 are folded upward and connected via the adhesive flaps 58. The roof portions 330 having the openings 313 are folded onto themselves by folding the roof segments 344 inward and folding the roof segments 345 outward as shown in FIG. 58.

Figure 59:
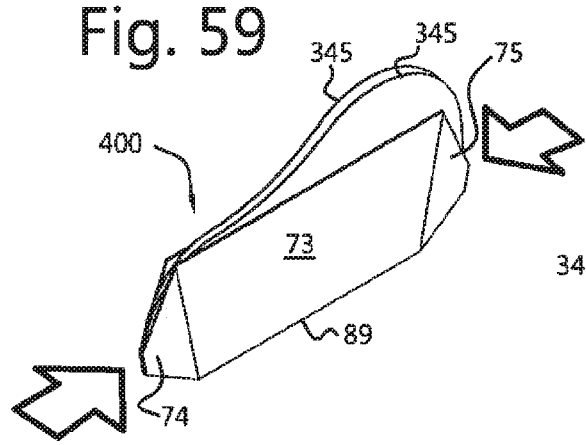

Turning to FIG. 59, next the collapsed container 400 is formed by folding the base section 13 over the central base fold line 66, wherein the diamond sections 7, 7A, 8, 8A are folded inward and the rest of the right and left wall zones 33, 34 are folded outward. The right and left wall zones 33,34 are folded over the side wall fold lines 14,15. FIG. 59 has a strong resemblance with FIG. 12 with the difference of the roof segments 345 extending upward.

Figure 60:
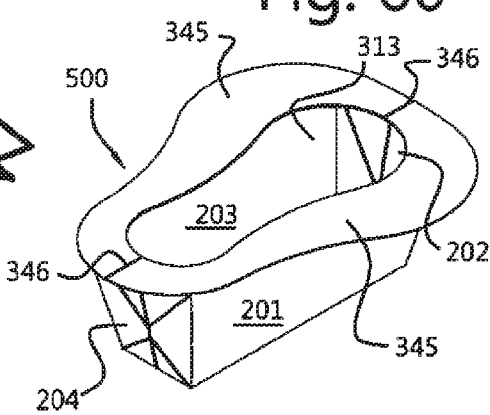

Turning to FIG. 60, when the collapsed container is to be expanded, the base section 13 is unfolded. The right and left wall zones 33, 34 are unfolded over the side wall fold lines 14, 15.

Turning to FIG. 61, a blank 10 according to the invention is shown. The blank 10 is very similar to the blank of FIG. 1, but with a few differences. In the base section 13 there are no fold lines 301. The diamond-shaped sections 7, 8 of FIG. 1 has become triangular shaped sections 7', 8'. For the rest, the blanks of FIG. 61 and FIG. 1 are quite similar.

A further feature shown in this embodiment is that the orientation of the blank, and in particular of the side wall fold lines 14, 15 relative to the dominant fiber orientation of the fibers in that paper or cardboard from which the blank is made, is relevant. The dominant fiber orientation is shown with arrow 310. Preferably, that side wall fold lines 14, 15 are oriented at right angles to the dominant fiber orientation. This improves the pop up effect when the collapsed container is expanded to a container by pushing the side wall fold lines 14, 15 inward.

Turning to FIG. 62, a blank 10 is shown. This blank is also quite similar to the blank of FIG. 1 and FIG. 61, with a few differences. The base perimeter fold line 30 is straight. An advantage of this straight base perimeter fold line 30 is that it is better suitable for a mechanical device which folds a large number of blanks into collapsed containers in a manufacturing line. The blanks of FIGS. 1 and 61 are more difficult to manufacture an automatic fashion.

Further, the base section edge 302 is also straight. This further improves the manufacturability of the collapsed containers which are made from the blanks 10.

Turning to FIG. 63, this blank also has a straight base perimeter fold line 30 and a straight base section edge 302. However, the edges 60, 59 of the wall section are cut differently and extend over the side wall fold line 14. 34. The edges 59,60 are straight, just like the base section edge 302.

The right wall zone 33 is thereby cut in two separate left wall zone parts 33A, 33B. In this way, the blank 10 has a shape which is substantially (but not entirely) rectangular. This further improves the possibility to manufacture collapsed containers in an automatic manner with a suitable folding device from the blank 10.

Turning to FIG. 64, and embodiment of the blank 10 is shown in which three side wall zones 31, 33, 32 are connected to one side of the base section 13, and in which one of the four side wall zones, namely side wall zone 34, is connected to an opposite side of the base section 13.

This embodiment has adhesive flaps 58 attached to either side of the side wall zone 34. This embodiment has an advantage in that it is symmetrical about the side wall fold lines 14, 15 and also about the central base fold line 66. The side wall fold lines 14, 15 are aligned with one another. The central base fold line 66 is also aligned with the side wall fold lines 14, 15.

Turning to FIG. 65, this embodiment is quite similar to the embodiment of FIG. 63 in that one of the side wall zones (the left wall 34) is divided into separate parts 34A, 34B, due to the position of the due to the position of the edge 199 of the blank relative to the side wall zones 31, 32, 33 and 34. However, contrary to FIG. 63, that base perimeter fold line 30 and the base section edge 302 are not straight but have a single corner 450. The base section edge 302 is continuous in the sense that the base portions 44, 45, 46 and 47 are fully attached to one another. The first base portion 44 is divided into separate base portion sections 44A, 44B.

Turning to FIG. 66, this embodiment is similar to the embodiment shown in FIG. 37. One difference is that the base portion 13 of the embodiment of FIG. 66 has a rectangular shape instead of the square shape of the embodiment shown in FIG. 37.

In the embodiment of FIG. 66, that side wall fold lines 14, 15 are oriented at right angles to the dominant direction of the fibers.

Turning to FIG. 67, in this embodiment both side wall zones 33 and 34 has been cut in two separate portions, 33A, 33B, 34A, 34B. This blank is symmetrical about the base fold line 66 which divides the front wall zone 31 and the rear wall zone 32 into identical portions. The blank 10 has base flaps 312, 313, which are interconnected by the interconnecting fold lines 320 which extend away from the corner locations 50, 51, 52 and 53. The base flaps 312, 313 have straight edges 314.

The embodiment of FIG. 68 is similar to the embodiment of FIG. 67, with a difference that base flaps 312, 313 are somewhat larger and have curved edges 314.

Turning to FIG. 69, an embodiment of a blank 10 is shown which by itself is not liquid tight. The corner locations 50, 51, 52, 53 are located along an edge 302 of the blank 10. In other words, this blank 10 does not have corner locations which are located at a distance from the edge of the blank and does not have the diagonal fold lines 54, 55, 56, 57 or the interconnecting fold lines 320 of the previous blanks. This blank therefore is prone to leakage at the corner locations, if no other provision is made.

This blank 10 can for instance be used to store non-fluid items, or can be provided with an inner liner bag to provide fluid tightness. An inner liner bag may be connected to the opening 28.

The base section 13 is simpler than for previously disclosed embodiments. The base section 13 comprises a front half 315A and a rear half 315B. The rear half is connected to the rear wall 32 by an adhesive strip 316.

This blank does have the capability to be expanded from a collapsed state to an expanded state by pushing the fold lines 14, 15 inward, thereby unfolding the left side wall and the right side wall.

Turning to FIG. 70, an embodiment of blank 700 for an inner liner bag 600 according to the invention is shown. The blank 100 has parts which are quite similar to the parts of the blank 10 for the container 200 and for this reason these parts are denoted with the same reference numerals. However it is to be kept in mind that the blank 700 is formed into a liner bag 600, not into a container 200. The blank 700 for the inner liner bag 600 has a rectangular shape. Each of the side walls 31, 32, 33 and 34 have a rectangular shape. The base section 13 also has a rectangular shape. The base perimeter fold line 30 is straight, and extends along the full width of the blank 10. The left front fold line 80, the right front fold line 81, the right rear fold line 181 and the left rear fold line 182 are also straight. The container which is formed from this blank has vertical sidewalls.

The blank 700 is not made from cardboard, but from plastic sheet or from laminated paper sheet. Other fluid tight materials may also be possible.

FIGS. 71 and 72 show the container 200 which is formed from the blank 10 of FIG. 69 and a liner bag 600 which is formed from the blank 700 shown in FIG. 70. The container 200 has a shape which is very similar to the shape shown in for instance FIG. 15. However, the bottom is not fully closed, and a triangular gap 602 exists near the bottom which would result in leakage if the bag 600 would not be provided.

The bag 600 is shown on the right side of FIG. 71 and has a front wall section 31 which is attached to the inner side of the front wall 201 of the container 200. The rear wall section of the bag 600 is connected to the rear wall 204 of the container 200. The opening 28 in the bag 600 is aligned with the opening 28 in the container 200. Because the bag 600 is fluid tight, the container 200 including the bag hundred will also be fluid tight.

The container 200 is generally stored in a collapsed state, just like the previous embodiments. In the collapsed state, the bag 600 extended will also be collapsed. The container is expanded to the expanded state in the same way as the previous embodiments, namely by pushing the fold lines 14, 15 inward with the hands of a user. Both the container and the bag 600 inside the container will then expand to the expanded state, and the container is ready for use.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The invention claimed is:

1. Single-use container manufactured from sheet material, the single-use container comprising:
    a base on which the single-use container can stand,
    a front wall, a right wall, a left wall and a rear wall which extend upward from the base,
    an upper end,
    wherein the right wall and left wall are connected to the front wall and rear wall via fold lines which extend upwardly from the base and wherein side wall fold lines extend over the right and left wall upwardly from the base,
    wherein a central base fold line extends along the base,
    wherein the single-use container is configured to be transformed from a collapsed state to an expanded state by unfolding the side wall fold lines and folding the fold lines, and unfolding the base about the central base fold line, thereby forming the right and left wall and expanding the collapsed single-use container into an expanded state,
    wherein the front wall and the rear wall are convex, and wherein the right wall and left wall are concave,
    wherein in front view the single-use container has a waist section, wherein the waist section has a front width which is smaller than a front width at the base and wherein the waist section front width is smaller than a front width at the upper end, wherein the front width gradually decreases from the base to the waist section and gradually increases from the waist section to the upper end,
    wherein the right wall and left wall are curved in a single plane of curvature;
    wherein corners of the base are located at a distance inward from an outer edge of the sheet material from which the single-use container is made.

2. Single-use container according to claim 1, forming a single-use urinal, wherein the front wall comprises:
    a pee opening, or
    a pee opening area having a perimeter which is at least partially weakened and is configured to be broken to remove the pee opening area or to fold the pee opening area inward or outward in order to form the pee opening;
    or wherein at least one side wall comprises:
    a pee opening, or
    a pee opening area having a perimeter which is at least partially weakened and is configured to be broken to remove the pee opening area or to fold the pee opening area inward or outward in order to form the pee opening.

3. Single-use container according to claim 1, wherein the upper end can be opened by the user by pushing left and right corners inward, thereby creating an upper opening.

4. Single-use container according to claim 1, comprising an inner liner bag which is attached to the inside of a front wall, the inner liner bag comprising an opening which is aligned with opening in the front wall.

5. Collapsed single-use container configured to be expanded into the single-use container according to claim 1, the collapsed single-use container being manufactured from sheet material and comprising:
    a base section folded onto itself along the central base fold line,
    a front part comprising:

a central front part which defines the front wall of the single-use container which is to be formed, a left front part, which defines a forward part of the left wall of the single-use container which is to be formed, a right front part, which defines a forward part of the right wall of the single- use container which is to be formed, a rear part comprising:

a central rear part which defines the rear wall of the single-use container which is to be formed, a left rear part which defines a rearward part of the left wall of the single-use container which is to be formed, a right rear part which defines a rearward part of the right wall of the single-use container which is to be formed, an upper end, wherein the central front part is connected to the left front part and right front part via fold lines, and wherein the central rear part is connected to the left rear part and right rear part via fold lines, wherein side wall fold lines extend over the right and left wall and form a right edge and a left edge of the collapsed single-use container, wherein the central base fold line extends along the base section, wherein the collapsed single-use container is configured to be transformed from the collapsed state to an expanded state by pushing the right edge and the left edge of the collapsed single-use container inward, thereby unfolding the side wall fold lines, forming the right and left wall and unfolding the base section into a base, wherein in the expanded state of the collapsed single-use container:

the front wall and the rear wall are convex, and the right wall and left wall are concave, and wherein in front view the single-use container has a waist section, the waist section having a front width which is smaller than a front width at the base and wherein the waist section front width is smaller than a front width at the upper end, wherein in particular the front width gradually decreases from the base to the waist section and gradually increases from the waist section to the upper end, and wherein the right wall and left wall are curved in a single plane of curvature, wherein corners of the base are located at a distance inward from an outer edge of the sheet material from which the single-use container is made.

6. Collapsed single-use container according to claim 5, wherein in front view the right edge comprises an upper right edge and a lower right edge, and the left edge comprises an upper left edge and a lower left edge, wherein due to the fact that the base section is folded onto itself:

the lower right edge comprises a front lower right edge part and a rear lower right edge part and the lower left edge comprises a front lower left edge part and a rear lower left edge part, wherein the upper right edge, the front lower right edge part and the rear lower right edge part form folding lines which can be pushed inwards, thereby forming the right wall during the expanding of the collapsible container, and wherein the upper left edge, the front lower left edge part and the rear lower left edge part form folding lines which can be pushed inwards, thereby forming the left wall during the expanding of the collapsible container.

7. Collapsed single-use container according to claim 5, forming a single-use urinal, wherein the front wall comprises:

a pee opening, or a pee opening area having a perimeter which is at least partially weakened and is configured to be broken to remove the pee opening area or to fold the pee opening area inward or outward in order to form the pee opening, or wherein at least one side wall comprises:

a pee opening, or a pee opening area having a perimeter which is at least partially weakened and is configured to be broken to remove the pee opening area or to fold the pee opening area inward or outward in order to form the pee opening.

8. Blank for manufacturing a collapsed single-use container according to claim 5, the blank comprising:

a base section, a wall section, and an upper end section, wherein the base section is delimited from the wall section by a base perimeter fold line, wherein the wall section comprises a front wall zone, a rear wall zone, a right wall zone and a left wall zone, wherein side wall fold lines extend over the right and left wall zone, wherein the front wall zone and the rear wall zone have a waist section having a width which is smaller than a width at a bottom of the front wall zone and the rear wall zone and smaller than a width at a top of the front wall zone and the rear wall zone, wherein the right wall zone and the left wall zone have a belly section having a width which is greater than a width at a bottom of the right wall zone and left wall zone and greater than a width at the top of the right wall zone and the left wall zone, wherein the front wall and the rear wall of the container which is to be formed from the collapsed single-use container are convex, and wherein the right wall and left wall of a container which is to be formed from the collapsed single-use container are concave, wherein the right wall and left wall of the container which is to be formed from the collapsed single-use container are curved in a single plane of curvature.

9. Blank according to claim 8, wherein the front wall zone comprises:

a pee opening, or a pee opening area having a perimeter which is at least partially weakened and is configured to be broken to remove the pee opening area or to fold the pee opening area inward or outward in order to form the pee opening;

wherein the base section has a square or rectangular shape, wherein the base is flat when unfolded and forms a surface on which the container can stand, wherein the corners of the base section are located at a distance inward from an outer edge of the blank.

10. Blank according to claim 8, wherein corner locations of the blank which are configured to form corners of base section of the collapsed single-use container and corners of base of the single-use container are located at a distance inward from an outer edge of the blank.

11. Blank according to claim 8, wherein the front wall zone comprises:
- a pee opening, or
- a pee opening area having a perimeter which is at least partially weakened and is configured to be broken to remove the pee opening area or to fold the pee opening area inward or outward in order to form the pee opening.

12. Method of manufacturing the collapsed single-use container according to claims 5 from the blank according to claim 8, the method comprising interconnecting the front wall zone, the rear wall zone, the right wall zone and the left wall zone into a circumferential wall by an adhesive connection.

13. Method according to claim 12, comprising providing an inner liner bag in the collapsed container and attaching a front wall of the inner liner bag to a front wall of the collapsed container, wherein the inner liner bag comprises an opening in the front wall, wherein said opening is aligned with the opening of the collapsed container.

14. Method of forming the single-use container of claim 1 from the collapsed container of claim 5, the method providing the collapsed container of claim 5, pushing a left edge and a right edge of the collapsed single-use container inward, and forming the concave right and left wall and the convex front and rear wall, wherein the right wall and left wall are curved in a single plane of curvature.

* * * * *